(12) United States Patent
Bernick et al.

(10) Patent No.: US 10,052,386 B2
(45) Date of Patent: *Aug. 21, 2018

(54) PROGESTERONE FORMULATIONS

(71) Applicant: TherapeuticsMD, Inc., Boca Raton, FL (US)

(72) Inventors: Brian A. Bernick, Boca Raton, FL (US); Julia M. Amadio, Boca Raton, FL (US); Peter H. R. Persicaner, Boca Raton, FL (US); Janice Louise Cacace, Miami, FL (US); Thorsteinn Thorsteinsson, West Palm Beach, FL (US); Frederick D. Sancilio, Palm Beach Gardens, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/125,547

(22) PCT Filed: Jun. 18, 2013

(86) PCT No.: PCT/US2013/046442
§ 371 (c)(1),
(2) Date: Dec. 11, 2013

(87) PCT Pub. No.: WO2013/192248
PCT Pub. Date: Dec. 27, 2013

(65) Prior Publication Data

US 2015/0148323 A1   May 28, 2015

Related U.S. Application Data

(63) Continuation of application No. 13/684,002, filed on Nov. 21, 2012, now Pat. No. 8,633,178, and a continuation-in-part of application No. 13/843,428, filed on Mar. 15, 2013, now Pat. No. 9,301,920, and a continuation of application No. PCT/US2013/023309, filed on Jan. 25, 2013, and a continuation of application No. 13/843,362, filed on Mar. 15, 2013.

(60) Provisional application No. 61/661,302, filed on Jun. 18, 2012, provisional application No. 61/662,265, filed on Jun. 20, 2012.

(51) Int. Cl.
| | | |
|---|---|---|
| A61K 31/57 | (2006.01) |
| A61K 31/56 | (2006.01) |
| A61K 47/44 | (2017.01) |
| A61K 47/10 | (2017.01) |
| A61K 47/14 | (2017.01) |
| A61K 31/573 | (2006.01) |
| A61K 31/566 | (2006.01) |
| A61K 9/00 | (2006.01) |
| A61K 31/565 | (2006.01) |
| A61K 9/48 | (2006.01) |
| A61K 45/06 | (2006.01) |
| A61K 9/107 | (2006.01) |

(52) U.S. Cl.
CPC ............ *A61K 47/14* (2013.01); *A61K 9/0014* (2013.01); *A61K 9/1075* (2013.01); *A61K 9/48* (2013.01); *A61K 9/4825* (2013.01); *A61K 31/565* (2013.01); *A61K 31/566* (2013.01); *A61K 31/57* (2013.01); *A61K 31/573* (2013.01); *A61K 45/06* (2013.01); *A61K 47/10* (2013.01)

(58) Field of Classification Search
CPC ......... A61K 31/57; A61K 47/44; A61K 47/10
See application file for complete search history.

(56) References Cited

U.S. PATENT DOCUMENTS

| | | |
|---|---|---|
| 1,967,351 A | 7/1934 | Dolay |
| 2,232,438 A | 2/1941 | Butenandt |
| 2,379,832 A | 7/1945 | Serini et al. |
| 2,649,399 A | 8/1953 | Beall et al. |
| 3,198,707 A | 8/1965 | Nomine et al. |
| 3,478,070 A | 11/1969 | Stein et al. |
| 3,526,648 A | 9/1970 | Bertin et al. |
| 3,710,795 A | 1/1973 | Higuchi et al. |
| 3,729,560 A | 4/1973 | Hagerman |
| 3,729,566 A | 4/1973 | Ericsson et al. |
| 3,755,573 A | 8/1973 | Berman |
| 3,755,575 A | 8/1973 | Lerner |
| 3,903,880 A | 9/1975 | Higuchi et al. |
| 3,916,898 A | 11/1975 | Robinson |
| 3,916,899 A | 11/1975 | Theeuwes et al. |
| 3,921,636 A | 11/1975 | Zaffaroni |
| 3,923,997 A | 12/1975 | Meuly |
| 3,948,254 A | 4/1976 | Zaffaroni |
| 3,971,367 A | 7/1976 | Zaffaroni |
| 3,977,404 A | 8/1976 | Theeuwes |
| 3,993,072 A | 11/1976 | Zaffaroni |

(Continued)

FOREIGN PATENT DOCUMENTS

| | | |
|---|---|---|
| BR | PI 1001367-9 A2 | 7/2012 |
| CA | 2548281 A1 | 6/2005 |

(Continued)

OTHER PUBLICATIONS

US 6,214,374, 04/2001, Schmirler et al. (withdrawn)
Abbas, M.A., et al., "Regression of Endometrial Implants Treated with Vitamin D3 in a Rat Model of Endometriosis," European Journal of Pharmacology 715(1-3):72-75, Elsevier Science, Netherlands (2013).
Abitec Corporation Excipients for the Pharmaceutical Industry—Regulatory and Product Information, 2 pages (2013).
Advisory Action dated Jan. 29, 2007 for U.S. Appl. No. 12/561,515, filed Sep. 17, 2009.
Alvarez, P., et al., "Ectopic Uterine Tissue as a Chronic Pain Generator," Neuroscience 225:269-282, Elsevier Science, United States (2012).

(Continued)

*Primary Examiner* — Samira Jean-Louis
(74) *Attorney, Agent, or Firm* — Sterne Kessler Goldstein & Fox; Matthew Bodenstein

(57) ABSTRACT

Various pharmaceutical formulations are disclosed herein. For example, a pharmaceutical formulation is disclosed comprising ultra-micronized progesterone.

40 Claims, 6 Drawing Sheets

(56) References Cited

U.S. PATENT DOCUMENTS

| | | |
|---|---|---|
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,987 A | 3/1977 | Heller et al. |
| 4,016,251 A | 4/1977 | Higuchi et al. |
| 4,071,623 A | 1/1978 | van der Vies |
| 4,093,709 A | 6/1978 | Choi et al. |
| 4,154,820 A | 5/1979 | Simoons |
| 4,155,991 A | 5/1979 | Schopflin et al. |
| 4,196,188 A | 4/1980 | Besins |
| 4,215,691 A | 8/1980 | Wong |
| 4,237,885 A | 12/1980 | Wong et al. |
| 4,310,510 A | 1/1982 | Sherman et al. |
| 4,327,725 A | 5/1982 | Cortese et al. |
| 4,372,951 A | 2/1983 | Vorys |
| 4,384,096 A | 5/1983 | Sonnabend |
| 4,393,871 A | 7/1983 | Vorhauer et al. |
| 4,402,695 A | 9/1983 | Wong |
| 4,423,151 A | 12/1983 | Baranczuk |
| 4,449,980 A | 5/1984 | Millar et al. |
| 4,610,687 A | 9/1986 | Fogwell |
| 4,629,449 A | 12/1986 | Wong |
| 4,732,763 A | 3/1988 | Beck et al. |
| 4,738,957 A | 4/1988 | Laurent et al. |
| 4,756,907 A | 7/1988 | Beck et al. |
| 4,762,717 A | 8/1988 | Crowley, Jr. |
| 4,788,062 A | 11/1988 | Gale et al. |
| 4,816,257 A | 3/1989 | Buster et al. |
| 4,822,616 A | 4/1989 | Zimmermann et al. |
| 4,865,848 A | 9/1989 | Cheng et al. |
| 4,900,734 A | 2/1990 | Maxson et al. |
| 4,906,475 A | 3/1990 | Kim |
| 4,942,158 A | 7/1990 | Sarpotdar et al. |
| 4,961,931 A | 10/1990 | Wong |
| 5,030,629 A | 7/1991 | Rajadhyaksha |
| 5,064,654 A | 11/1991 | Berner et al. |
| 5,108,995 A | 4/1992 | Casper |
| 5,128,138 A | 7/1992 | Blank |
| 5,130,137 A | 7/1992 | Crowley, Jr. |
| 5,140,021 A | 8/1992 | Maxson et al. |
| 5,211,952 A | 5/1993 | Spicer et al. |
| 5,252,334 A | 10/1993 | Chiang et al. |
| 5,280,023 A | 1/1994 | Ehrlich et al. |
| 5,288,496 A | 2/1994 | Lewis |
| 5,340,584 A | 8/1994 | Spicer et al. |
| 5,340,585 A | 8/1994 | Pike et al. |
| 5,340,586 A | 8/1994 | Pike et al. |
| 5,362,497 A | 11/1994 | Yamada et al. |
| 5,382,573 A | 1/1995 | Casper |
| 5,393,528 A | 2/1995 | Staab |
| 5,393,529 A | 2/1995 | Hoffmann et al. |
| 5,419,910 A | 5/1995 | Lewis |
| 5,468,736 A | 11/1995 | Hodgen |
| 5,474,783 A | 12/1995 | Miranda et al. |
| 5,480,776 A | 1/1996 | Dullien |
| 5,514,673 A | 5/1996 | Heckenmueller et al. |
| 5,516,528 A | 5/1996 | Hughes et al. |
| 5,527,534 A | 6/1996 | Myhling |
| 5,529,782 A | 6/1996 | Staab |
| 5,538,736 A | 7/1996 | Hoffmann et al. |
| 5,543,150 A | 8/1996 | Bologna et al. |
| 5,547,948 A | 8/1996 | Barcomb |
| 5,556,635 A | 9/1996 | Istin et al. |
| 5,565,199 A | 10/1996 | Page et al. |
| 5,567,831 A | 10/1996 | Li |
| 5,569,652 A | 10/1996 | Beier et al. |
| 5,580,572 A | 12/1996 | Mikler et al. |
| 5,582,592 A | 12/1996 | Kendrick |
| 5,585,370 A | 12/1996 | Casper |
| 5,595,759 A | 1/1997 | Wright et al. |
| 5,595,970 A | 1/1997 | Garfield et al. |
| 5,605,702 A | 2/1997 | Teillaud et al. |
| 5,607,691 A | 3/1997 | Hale et al. |
| 5,607,693 A | 3/1997 | Bonte et al. |
| 5,609,617 A | 3/1997 | Shealy et al. |
| 5,620,705 A | 4/1997 | Dong et al. |
| 5,626,866 A | 5/1997 | Ebert et al. |
| 5,629,021 A | 5/1997 | Wright |
| 5,633,011 A | 5/1997 | Dong et al. |
| 5,633,242 A | 5/1997 | Oettel et al. |
| 5,639,743 A | 6/1997 | Kaswan et al. |
| 5,653,983 A | 8/1997 | Meybeck et al. |
| 5,656,286 A | 8/1997 | Miranda et al. |
| 5,660,839 A | 8/1997 | Allec et al. |
| 5,662,927 A | 9/1997 | Ehrlich et al. |
| 5,663,160 A | 9/1997 | Meybeck et al. |
| 5,676,968 A | 10/1997 | Lipp et al. |
| 5,677,292 A | 10/1997 | Li et al. |
| 5,686,097 A | 11/1997 | Taskovich et al. |
| 5,693,335 A | 12/1997 | Xia et al. |
| 5,694,947 A | 12/1997 | Lehtinen et al. |
| 5,700,480 A | 12/1997 | Hille et al. |
| 5,709,844 A | 1/1998 | Arbeit et al. |
| 5,719,197 A | 2/1998 | Kanios et al. |
| 5,735,801 A | 4/1998 | Caillouette |
| 5,739,176 A | 4/1998 | Dunn et al. |
| 5,744,463 A | 4/1998 | Bar |
| 5,747,058 A | 5/1998 | Tipton et al. |
| 5,762,614 A | 6/1998 | Caillouette |
| 5,770,176 A | 6/1998 | Nargessi |
| 5,770,219 A | 6/1998 | Chiang et al. |
| 5,770,220 A | 6/1998 | Meconi et al. |
| 5,770,227 A | 6/1998 | Dong et al. |
| 5,776,495 A | 7/1998 | Duclos et al. |
| 5,780,044 A | 7/1998 | Yewey et al. |
| 5,780,050 A | 7/1998 | Jain et al. |
| 5,788,980 A | 8/1998 | Nabahi |
| 5,788,984 A | 8/1998 | Guenther et al. |
| 5,789,442 A | 8/1998 | Garfield et al. |
| 5,811,416 A | 9/1998 | Chwalisz et al. |
| 5,811,547 A | 9/1998 | Nakamichi et al. |
| 5,814,329 A | 9/1998 | Shah |
| 5,820,878 A | 10/1998 | Hirano et al. |
| 5,827,200 A | 10/1998 | Caillouette |
| 5,840,327 A | 11/1998 | Gale et al. |
| 5,843,468 A | 12/1998 | Burkoth et al. |
| 5,843,979 A | 12/1998 | Wille et al. |
| 5,858,394 A | 1/1999 | Lipp et al. |
| 5,863,552 A | 1/1999 | Yue |
| 5,866,603 A | 2/1999 | Li et al. |
| 5,882,676 A | 3/1999 | Lee et al. |
| 5,885,612 A | 3/1999 | Meconi et al. |
| 5,888,533 A | 3/1999 | Dunn |
| 5,891,462 A | 4/1999 | Carrara |
| 5,891,868 A | 4/1999 | Cummings et al. |
| 5,898,038 A | 4/1999 | Yallampalli et al. |
| 5,902,603 A | 5/1999 | Chen et al. |
| 5,904,931 A | 5/1999 | Lipp et al. |
| 5,906,830 A | 5/1999 | Farinas et al. |
| 5,912,010 A | 6/1999 | Wille et al. |
| 5,916,176 A | 6/1999 | Caillouette |
| RE36,247 E | 7/1999 | Plunkett et al. |
| 5,919,477 A | 7/1999 | Bevan et al. |
| 5,922,349 A | 7/1999 | Elliesen et al. |
| 5,928,666 A | 7/1999 | Farinas et al. |
| 5,942,243 A | 8/1999 | Shah |
| 5,952,000 A | 9/1999 | Venkateshwaran et al. |
| 5,958,446 A | 9/1999 | Miranda et al. |
| 5,962,445 A | 10/1999 | Stewart |
| 5,968,919 A | 10/1999 | Samour et al. |
| 5,972,372 A | 10/1999 | Saleh et al. |
| 5,985,311 A | 11/1999 | Cordes et al. |
| 5,985,850 A | 11/1999 | Falk et al. |
| 5,985,861 A | 11/1999 | Levine et al. |
| 5,989,568 A | 11/1999 | Breton et al. |
| 5,993,856 A | 11/1999 | Ragavan et al. |
| 6,001,846 A | 12/1999 | Edwards et al. |
| 6,007,835 A | 12/1999 | Bon-Lapillonne et al. |
| 6,010,715 A | 1/2000 | Wick et al. |
| 6,013,276 A | 1/2000 | Math et al. |
| 6,022,562 A | 2/2000 | Autant et al. |
| 6,024,974 A | 2/2000 | Li |
| 6,024,976 A | 2/2000 | Miranda et al. |
| 6,028,057 A | 2/2000 | Burns |

(56) References Cited

U.S. PATENT DOCUMENTS

| | | |
|---|---|---|
| 6,030,948 A | 2/2000 | Mann |
| 6,039,968 A | 3/2000 | Nabahi |
| 6,040,340 A | 3/2000 | Chwalisz et al. |
| 6,056,972 A | 5/2000 | Hermsmeyer |
| 6,060,077 A | 5/2000 | Meignant |
| 6,068,853 A | 5/2000 | Giannos et al. |
| 6,074,625 A | 6/2000 | Hawthorne et al. |
| 6,077,531 A | 6/2000 | Salin-Drouin |
| 6,080,118 A | 6/2000 | Blythe |
| 6,083,178 A | 7/2000 | Caillouette |
| 6,086,916 A | 7/2000 | Agnus et al. |
| 6,087,352 A | 7/2000 | Trout |
| 6,090,404 A | 7/2000 | Meconi et al. |
| 6,096,338 A | 8/2000 | Lacy et al. |
| 6,106,848 A | 8/2000 | Preuilh et al. |
| 6,117,446 A | 9/2000 | Place |
| 6,117,450 A | 9/2000 | Dittgen et al. |
| 6,124,362 A | 9/2000 | Bradbury et al. |
| 6,133,251 A | 10/2000 | Dittgen et al. |
| 6,133,320 A | 10/2000 | Yallampalli et al. |
| 6,139,868 A | 10/2000 | Hoffmann |
| 6,139,873 A | 10/2000 | Hughes, Jr. et al. |
| 6,149,935 A | 11/2000 | Chiang et al. |
| 6,153,216 A | 11/2000 | Cordes et al. |
| 6,165,491 A | 12/2000 | Grasset et al. |
| 6,165,975 A | 12/2000 | Adams et al. |
| 6,187,323 B1 | 2/2001 | Aiache et al. |
| 6,187,339 B1 | 2/2001 | de Haan et al. |
| 6,190,331 B1 | 2/2001 | Caillouette |
| 6,201,072 B1 | 3/2001 | Rathi et al. |
| 6,217,886 B1 | 4/2001 | Önyüksel et al. |
| 6,225,297 B1 | 5/2001 | Stockemann et al. |
| 6,227,202 B1 | 5/2001 | Matapurkar |
| 6,228,383 B1 | 5/2001 | Hansen et al. |
| 6,228,852 B1 | 5/2001 | Shaak |
| 6,242,509 B1 | 6/2001 | Berger et al. |
| 6,245,811 B1 | 6/2001 | Horrobin et al. |
| 6,262,115 B1 | 7/2001 | Guittard et al. |
| 6,264,980 B1 | 7/2001 | Hille |
| 6,267,984 B1 | 7/2001 | Beste et al. |
| 6,274,165 B1 | 8/2001 | Meconi et al. |
| 6,277,418 B1 | 8/2001 | Marakverich et al. |
| 6,283,927 B1 | 9/2001 | Caillouette |
| 6,287,588 B1 | 9/2001 | Shih et al. |
| 6,287,693 B1 | 9/2001 | Savoir et al. |
| 6,294,188 B1 | 9/2001 | Ragavan et al. |
| 6,294,192 B1 | 9/2001 | Patel et al. |
| 6,294,550 B1 | 9/2001 | Place et al. |
| 6,299,900 B1 | 10/2001 | Reed et al. |
| 6,303,132 B1 | 10/2001 | Nelson |
| 6,303,588 B1 | 10/2001 | Danielov |
| 6,306,841 B1 | 10/2001 | Place et al. |
| 6,306,914 B1 | 10/2001 | de Ziegler et al. |
| 6,309,669 B1 | 10/2001 | Setterstrom et al. |
| 6,309,848 B1 | 10/2001 | Howett et al. |
| 6,312,703 B1 | 11/2001 | Orthoefer |
| 6,328,987 B1 | 12/2001 | Marini |
| 6,342,491 B1 | 1/2002 | Dey et al. |
| 6,344,211 B1 | 2/2002 | Hille |
| 6,372,209 B1 | 4/2002 | Chrisope |
| 6,372,245 B1 | 4/2002 | Bowman et al. |
| 6,372,246 B1 | 4/2002 | Wei et al. |
| 6,387,390 B1 | 5/2002 | Deaver et al. |
| 6,402,705 B1 | 6/2002 | Caillouette |
| 6,416,778 B1 | 7/2002 | Ragavan et al. |
| 6,420,352 B1 | 7/2002 | Knowles |
| 6,423,039 B1 | 7/2002 | Rathbone et al. |
| 6,423,683 B1 | 7/2002 | Heaton et al. |
| 6,432,438 B1 | 8/2002 | Shukla |
| 6,436,633 B1 | 8/2002 | Kreider et al. |
| 6,440,454 B1 | 8/2002 | Santoro et al. |
| 6,444,224 B1 | 9/2002 | Rathbone et al. |
| 6,444,234 B1 | 9/2002 | Kirby et al. |
| 6,451,300 B1 | 9/2002 | Dunlop et al. |
| 6,451,339 B2 | 9/2002 | Patel et al. |
| 6,451,779 B1 | 9/2002 | Hesch |
| 6,455,246 B1 | 9/2002 | Howett et al. |
| 6,455,517 B1 | 9/2002 | Tanabe et al. |
| 6,465,004 B1 | 10/2002 | Rossi-Montero et al. |
| 6,465,005 B1 | 10/2002 | Biali et al. |
| 6,465,006 B1 | 10/2002 | Zhang et al. |
| 6,468,526 B2 | 10/2002 | Chrisope |
| 6,469,016 B1 | 10/2002 | Place et al. |
| 6,472,434 B1 | 10/2002 | Place et al. |
| 6,479,232 B1 | 11/2002 | Howett et al. |
| 6,495,160 B2 | 12/2002 | Esposito et al. |
| 6,500,814 B1 | 12/2002 | Hesch |
| 6,503,896 B1 | 1/2003 | Tanabe et al. |
| 6,511,969 B1 | 1/2003 | Hermsmeyer |
| 6,521,250 B2 | 2/2003 | Meconi et al. |
| 6,526,980 B1 | 3/2003 | Tracy et al. |
| 6,528,094 B1 | 3/2003 | Savoir et al. |
| 6,531,149 B1 | 3/2003 | Kirstgen et al. |
| 6,537,580 B1 | 3/2003 | Savoir et al. |
| 6,538,039 B2 | 3/2003 | Laurent |
| 6,544,196 B2 | 4/2003 | Caillouette |
| 6,544,553 B1 | 4/2003 | Hsia et al. |
| 6,548,053 B1 | 4/2003 | Stewart et al. |
| 6,548,491 B2 | 4/2003 | Tanabe et al. |
| 6,551,611 B2 | 4/2003 | Elliesen et al. |
| 6,555,131 B1 | 4/2003 | Wolff et al. |
| 6,562,367 B1 | 5/2003 | Wolff et al. |
| 6,562,370 B2 | 5/2003 | Luo et al. |
| 6,562,790 B2 | 5/2003 | Chein et al. |
| 6,569,463 B2 | 5/2003 | Patel et al. |
| 6,583,129 B1 | 6/2003 | Mazer et al. |
| 6,586,006 B2 | 7/2003 | Roser et al. |
| 6,589,549 B2 | 7/2003 | Shin et al. |
| 6,593,317 B1 | 7/2003 | de Ziegler et al. |
| 6,599,519 B1 | 7/2003 | Seo et al. |
| 6,610,652 B2 | 8/2003 | Adams et al. |
| 6,610,670 B2 | 8/2003 | Backensfeld et al. |
| 6,610,674 B1 | 8/2003 | Schreiber |
| 6,635,274 B1 | 10/2003 | Masiz et al. |
| 6,638,528 B1 | 10/2003 | Kanios |
| 6,638,536 B2 | 10/2003 | Savoir et al. |
| 6,645,528 B1 | 11/2003 | Straub et al. |
| 6,649,155 B1 | 11/2003 | Dunlop et al. |
| 6,653,298 B1 | 11/2003 | Potter et al. |
| 6,656,929 B1 | 12/2003 | Agnus et al. |
| 6,660,726 B2 | 12/2003 | Hill et al. |
| 6,663,608 B2 | 12/2003 | Rathbone et al. |
| 6,663,895 B2 | 12/2003 | Savoir et al. |
| 6,682,757 B1 | 1/2004 | Wright |
| 6,692,763 B1 | 2/2004 | Cummings et al. |
| 6,708,822 B1 | 3/2004 | Muni |
| 6,720,001 B2 | 4/2004 | Chen et al. |
| 6,737,081 B2 | 5/2004 | Savoir et al. |
| 6,740,333 B2 | 5/2004 | Beckett et al. |
| 6,743,448 B2 | 6/2004 | Kryger |
| 6,743,815 B2 | 6/2004 | Huebner et al. |
| 6,747,018 B2 | 6/2004 | Tanabe et al. |
| 6,750,291 B2 | 6/2004 | Kim et al. |
| 6,756,208 B2 | 6/2004 | Griffin et al. |
| 6,776,164 B2 | 8/2004 | Bunt et al. |
| 6,787,152 B2 | 9/2004 | Kirby et al. |
| 6,805,877 B2 | 10/2004 | Massara et al. |
| 6,809,085 B1 | 10/2004 | Elson et al. |
| 6,818,226 B2 | 11/2004 | Reed et al. |
| 6,821,524 B2 | 11/2004 | Marini |
| 6,841,716 B1 | 1/2005 | Tsutsumi |
| 6,844,334 B2 | 1/2005 | Hill et al. |
| 6,855,703 B1 | 2/2005 | Hill et al. |
| 6,860,859 B2 | 3/2005 | Mehrotra et al. |
| 6,866,865 B2 | 3/2005 | Hsia et al. |
| 6,869,969 B2 | 3/2005 | Heubner et al. |
| 6,878,518 B2 | 4/2005 | Whitehead |
| 6,901,278 B1 | 5/2005 | Notelovitz |
| 6,905,705 B2 | 6/2005 | Palm et al. |
| 6,911,211 B2 | 6/2005 | Eini et al. |
| 6,911,438 B2 | 6/2005 | Wright |
| 6,923,988 B2 | 8/2005 | Patel et al. |
| 6,924,274 B2 | 8/2005 | Lardy et al. |
| 6,932,983 B1 | 8/2005 | Straub et al. |

(56) References Cited

U.S. PATENT DOCUMENTS

| | | |
|---|---|---|
| 6,939,558 B2 | 9/2005 | Massara et al. |
| 6,943,021 B2 | 9/2005 | Klausner et al. |
| 6,958,327 B1 | 10/2005 | Hillisch et al. |
| 6,960,337 B2 | 11/2005 | Daniels et al. |
| 6,962,691 B1 | 11/2005 | Lulla et al. |
| 6,962,908 B2 | 11/2005 | Aloba et al. |
| 6,967,194 B1 | 11/2005 | Matsuo et al. |
| 6,974,569 B2 | 12/2005 | Dunlop et al. |
| 6,977,250 B2 | 12/2005 | Rodriguez |
| 6,978,945 B2 | 12/2005 | Wong et al. |
| 6,995,149 B1 | 2/2006 | Endrikat et al. |
| 7,004,321 B1 | 2/2006 | Palm et al. |
| 7,005,429 B2 | 2/2006 | Dey et al. |
| 7,011,846 B2 | 3/2006 | Shojaei et al. |
| 7,018,992 B2 | 3/2006 | Koch et al. |
| 7,030,104 B2 | 4/2006 | Gray et al. |
| 7,030,157 B2 | 4/2006 | Ke et al. |
| RE39,104 E | 5/2006 | Duclos et al. |
| 7,074,779 B2 | 7/2006 | Sui et al. |
| 7,083,590 B1 | 8/2006 | Bunt et al. |
| 7,091,213 B2 | 8/2006 | Metcalf, III et al. |
| 7,094,228 B2 | 8/2006 | Zhang et al. |
| 7,097,853 B1 | 8/2006 | Garbe et al. |
| 7,101,342 B1 | 9/2006 | Caillouette |
| 7,105,573 B2 | 9/2006 | Krajcik et al. |
| 7,135,190 B2 | 11/2006 | Piao et al. |
| 7,153,522 B1 | 12/2006 | Ikeura et al. |
| 7,163,681 B2 | 1/2007 | Giles-Komar et al. |
| 7,163,699 B2 | 1/2007 | Besse |
| 7,175,850 B2 | 2/2007 | Cevc |
| 7,179,799 B2 | 2/2007 | Hill et al. |
| 7,196,074 B2 | 3/2007 | Blye et al. |
| 7,198,800 B1 | 4/2007 | Ko |
| 7,198,801 B2 | 4/2007 | Carrara et al. |
| 7,226,910 B2 | 6/2007 | Wilson et al. |
| 7,247,625 B2 | 7/2007 | Zhang et al. |
| 7,250,446 B2 | 7/2007 | Sangita et al. |
| 7,267,829 B2 | 9/2007 | Kirby et al. |
| 7,300,926 B2 | 11/2007 | Prokai et al. |
| 7,303,763 B2 | 12/2007 | Ho |
| 7,317,037 B2 | 1/2008 | Fensome et al. |
| 7,329,654 B2 | 2/2008 | Kanojia et al. |
| 7,335,650 B2 | 2/2008 | Potter et al. |
| 7,374,779 B2 | 5/2008 | Chen et al. |
| 7,378,404 B2 | 5/2008 | Peters et al. |
| 7,381,427 B2 | 6/2008 | Ancira et al. |
| 7,388,006 B2 | 6/2008 | Schmees et al. |
| 7,387,789 B2 | 7/2008 | Klose et al. |
| 7,414,043 B2 | 8/2008 | Kosemund et al. |
| 7,427,413 B2 | 9/2008 | Savoir et al. |
| 7,427,609 B2 | 9/2008 | Leonard |
| 7,429,576 B2 | 9/2008 | Labrie |
| 7,431,941 B2 | 10/2008 | Besins et al. |
| 7,456,159 B2 | 11/2008 | Houze et al. |
| 7,459,445 B2 | 12/2008 | Hill et al. |
| 7,465,587 B2 | 12/2008 | Imrich |
| 7,470,433 B2 | 12/2008 | Carrara et al. |
| 7,485,666 B2 | 2/2009 | Villanueva et al. |
| 7,497,855 B2 | 3/2009 | Ausiello et al. |
| 7,498,303 B2 | 3/2009 | Arnold et al. |
| 7,534,765 B2 | 5/2009 | Gregg et al. |
| 7,534,780 B2 | 5/2009 | Wyrwa et al. |
| 7,550,142 B2 | 6/2009 | Giles-Komar et al. |
| 7,563,565 B1 | 7/2009 | Matsuo et al. |
| 7,569,274 B2 | 8/2009 | Besse et al. |
| 7,572,779 B2 | 8/2009 | Aloba et al. |
| 7,572,780 B2 | 8/2009 | Hermsmeyer |
| 7,589,082 B2 | 9/2009 | Savoir et al. |
| 7,671,027 B2 | 3/2010 | Loumaye |
| 7,674,783 B2 | 3/2010 | Hermsmeyer |
| 7,687,281 B2 | 3/2010 | Roth et al. |
| 7,687,485 B2 | 3/2010 | Levinson et al. |
| 7,694,683 B2 | 4/2010 | Callister et al. |
| 7,704,983 B1 | 4/2010 | Hodgen et al. |
| 7,727,720 B2 | 6/2010 | Dhallan |
| 7,732,408 B2 | 6/2010 | Josephson et al. |
| 7,749,989 B2 | 7/2010 | Hill et al. |
| 7,767,656 B2 | 8/2010 | Shoichet et al. |
| 7,799,769 B2 | 9/2010 | White et al. |
| 7,815,936 B2 | 10/2010 | Hasenzahl et al. |
| 7,815,949 B2 | 10/2010 | Cohen |
| 7,829,115 B2 | 11/2010 | Besins et al. |
| 7,829,116 B2 | 11/2010 | Griswold et al. |
| RE42,012 E | 12/2010 | Deaver et al. |
| 7,850,992 B2 | 12/2010 | Kim et al. |
| 7,854,753 B2 | 12/2010 | Kraft et al. |
| 7,858,607 B2 | 12/2010 | Mamchur |
| RE42,072 E | 1/2011 | Deaver et al. |
| 7,862,552 B2 | 1/2011 | McIntyre et al. |
| 7,867,990 B2 | 1/2011 | Schultz et al. |
| 7,871,643 B2 | 1/2011 | Lizio et al. |
| 7,879,830 B2 | 2/2011 | Wiley |
| 7,884,093 B2 | 2/2011 | Creasy et al. |
| 7,925,519 B2 | 4/2011 | Greene |
| 7,939,104 B2 | 5/2011 | Barbera et al. |
| 7,943,602 B2 | 5/2011 | Bunschoten et al. |
| 7,943,604 B2 | 5/2011 | Coelingh Bennink et al. |
| 7,945,459 B2 | 5/2011 | Grace et al. |
| 7,960,368 B2 | 6/2011 | Nickisch et al. |
| 7,989,436 B2 | 8/2011 | Hill et al. |
| 7,989,487 B2 | 8/2011 | Welsh et al. |
| 8,022,053 B2 | 9/2011 | Mueller et al. |
| 8,048,017 B2 | 11/2011 | Xu |
| 8,048,869 B2 | 11/2011 | Bunschoten et al. |
| 8,063,030 B2 | 11/2011 | Ellman |
| 8,071,576 B2 | 12/2011 | Coelingh Bennink et al. |
| 8,071,729 B2 | 12/2011 | Giles-Komar et al. |
| 8,075,916 B2 | 12/2011 | Song et al. |
| 8,075,917 B2 | 12/2011 | Chung et al. |
| 8,076,317 B2 | 12/2011 | Kulmann |
| 8,076,319 B2 | 12/2011 | Leonard |
| 8,080,553 B2 | 12/2011 | Keith et al. |
| 8,088,605 B2 | 1/2012 | Beaudet et al. |
| 8,096,940 B2 | 1/2012 | Josephson et al. |
| 8,101,209 B2 | 1/2012 | Legrand et al. |
| 8,101,773 B2 | 1/2012 | Smith et al. |
| 8,114,152 B2 | 2/2012 | Furst |
| 8,114,434 B2 | 2/2012 | Sasaki et al. |
| 8,114,442 B2 | 2/2012 | Tucker et al. |
| 8,119,741 B2 | 2/2012 | Pavlin |
| 8,121,886 B2 | 2/2012 | Azar |
| 8,124,118 B2 | 2/2012 | Lennernas et al. |
| 8,124,595 B2 | 2/2012 | Boissonneault |
| 8,147,561 B2 | 4/2012 | Binmoeller |
| 8,148,546 B2 | 4/2012 | Schuster et al. |
| 8,158,613 B2 | 4/2012 | Staniforth et al. |
| 8,158,614 B2 | 4/2012 | Lambert et al. |
| 8,163,722 B2 | 4/2012 | Savoir et al. |
| 8,177,449 B2 | 5/2012 | Bayly et al. |
| 8,182,833 B2 | 5/2012 | Hermsmeyer |
| 8,187,615 B2 | 5/2012 | Friedman |
| 8,195,403 B2 | 6/2012 | Ishikawa et al. |
| 8,202,736 B2 | 6/2012 | Mousa et al. |
| 8,217,024 B2 | 7/2012 | Ahmed et al. |
| 8,221,785 B2 | 7/2012 | Chien |
| 8,222,008 B2 | 7/2012 | Thoene |
| 8,222,237 B2 | 7/2012 | Nickisch et al. |
| 8,227,454 B2 | 7/2012 | Hill et al. |
| 8,227,509 B2 | 7/2012 | Castro et al. |
| 8,241,664 B2 | 8/2012 | Dudley et al. |
| 8,247,393 B2 | 8/2012 | Ahmed et al. |
| 8,257,724 B2 | 9/2012 | Cromack et al. |
| 8,257,725 B2 | 9/2012 | Cromack et al. |
| 8,268,352 B2 | 9/2012 | Vaya et al. |
| 8,268,806 B2 | 9/2012 | Labrie |
| 8,268,878 B2 | 9/2012 | Armer et al. |
| 8,273,730 B2 | 9/2012 | Fernandez et al. |
| 8,287,888 B2 | 10/2012 | Song et al. |
| 8,288,366 B2 | 10/2012 | Chochinov et al. |
| 8,318,898 B2 | 11/2012 | Fasel et al. |
| 8,324,193 B2 | 12/2012 | Lee-Sepsick et al. |
| 8,329,680 B2 | 12/2012 | Evans et al. |
| 8,337,814 B2 | 12/2012 | Osbakken et al. |
| 8,344,007 B2 | 1/2013 | Tang et al. |

(56) References Cited

U.S. PATENT DOCUMENTS

| | | |
|---|---|---|
| 8,349,820 B2 | 1/2013 | Zeun et al. |
| 8,353,863 B2 | 1/2013 | Imran |
| 8,357,723 B2 | 1/2013 | Satyam |
| 8,361,995 B2 | 1/2013 | Schramm |
| 8,362,091 B2 | 1/2013 | Tamarkin et al. |
| 8,372,424 B2 | 2/2013 | Berry et al. |
| 8,372,806 B2 | 2/2013 | Bohler et al. |
| 8,377,482 B2 | 2/2013 | Laurie et al. |
| 8,377,994 B2 | 2/2013 | Gray et al. |
| 8,394,759 B2 | 3/2013 | Barathur et al. |
| 8,435,561 B2 | 3/2013 | Besins et al. |
| 8,415,332 B2 | 4/2013 | Diliberti et al. |
| 8,420,111 B2 | 4/2013 | Hermsmeyer |
| 8,435,972 B2 | 5/2013 | Stein et al. |
| 8,449,879 B2 | 5/2013 | Laurent-Applegate et al. |
| 8,450,108 B2 | 5/2013 | Boyce |
| 8,454,945 B2 | 6/2013 | McCook et al. |
| 8,455,468 B2 | 6/2013 | Hoffman et al. |
| 8,461,138 B2 | 6/2013 | Boissonneault |
| 8,476,252 B2 | 7/2013 | Achleitner et al. |
| 8,481,488 B2 | 7/2013 | Carter |
| 8,486,374 B2 | 7/2013 | Tamarkin et al. |
| 8,486,442 B2 | 7/2013 | Matsushita et al. |
| 8,492,368 B2 | 7/2013 | Vanlandingham et al. |
| 8,507,467 B2 | 8/2013 | Matsui et al. |
| 8,512,693 B2 | 8/2013 | Capito et al. |
| 8,512,754 B2 | 8/2013 | Needham |
| 8,518,376 B2 | 8/2013 | Tamarkin et al. |
| 8,536,159 B2 | 9/2013 | Li et al. |
| 8,540,967 B2 | 9/2013 | Barrett et al. |
| 8,541,400 B2 | 9/2013 | Johnsson et al. |
| 8,551,462 B2 | 10/2013 | Goldstein et al. |
| 8,557,281 B2 | 10/2013 | Halliday et al. |
| 8,568,374 B2 | 10/2013 | De Graaff et al. |
| 8,591,951 B2 | 11/2013 | Kohn et al. |
| 8,613,951 B2 | 12/2013 | Zale et al. |
| 8,633,178 B2 | 1/2014 | Bernick et al. |
| 8,633,180 B2 | 1/2014 | Li et al. |
| 8,636,787 B2 | 1/2014 | Sabaria |
| 8,636,982 B2 | 1/2014 | Tamarkin et al. |
| 8,653,129 B2 | 2/2014 | Fein et al. |
| 8,658,627 B2 | 2/2014 | Voskuhl |
| 8,658,628 B2 | 2/2014 | Baucom |
| 8,663,681 B2 | 3/2014 | Nakamichi et al. |
| 8,663,692 B1 | 3/2014 | Mueller et al. |
| 8,663,703 B2 | 3/2014 | Lerner et al. |
| 8,664,207 B2 | 3/2014 | Li et al. |
| 8,669,293 B2 | 3/2014 | Levy et al. |
| 8,679,552 B2 | 3/2014 | Guthery |
| 8,694,358 B2 | 4/2014 | Tryfon |
| 8,697,127 B2 | 4/2014 | Sah |
| 8,697,710 B2 | 4/2014 | Li et al. |
| 8,703,105 B2 | 4/2014 | Tamarkin et al. |
| 8,709,385 B2 | 4/2014 | Tamarkin et al. |
| 8,709,451 B2 | 4/2014 | Rapoport et al. |
| 8,715,735 B2 | 5/2014 | Funke et al. |
| 8,721,331 B2 | 5/2014 | Raghuprasad |
| 8,722,021 B2 | 5/2014 | Friedman et al. |
| 8,734,846 B2 | 5/2014 | Ali et al. |
| 8,735,381 B2 | 5/2014 | Podolski |
| 8,741,336 B2 | 6/2014 | Dipierro et al. |
| 8,741,373 B2 | 6/2014 | Bromley et al. |
| 8,753,661 B2 | 6/2014 | Steinmuller-Nethl et al. |
| 8,784,882 B2 | 7/2014 | Mattern |
| 8,815,261 B2 | 8/2014 | Hanma |
| 8,846,648 B2 | 9/2014 | Bernick et al. |
| 8,846,649 B2 | 9/2014 | Bernick et al. |
| 8,933,059 B2 | 1/2015 | Bernick et al. |
| 8,987,237 B2 | 3/2015 | Bernick et al. |
| 8,987,238 B2 | 3/2015 | Bernick et al. |
| 8,993,548 B2 | 3/2015 | Bernick et al. |
| 8,993,549 B2 | 3/2015 | Bernick et al. |
| 9,006,222 B2 | 4/2015 | Bernick et al. |
| 9,012,434 B2 | 4/2015 | Bernick et al. |
| 9,289,382 B2 | 3/2016 | Bernick et al. |
| 2001/0005728 A1 | 6/2001 | Guittard et al. |
| 2001/0009673 A1 | 7/2001 | Lipp et al. |
| 2001/0021816 A1 | 9/2001 | Caillouette |
| 2001/0023261 A1 | 9/2001 | Ryoo et al. |
| 2001/0027189 A1 | 10/2001 | Bennink et al. |
| 2001/0029357 A1 | 10/2001 | Bunt et al. |
| 2001/0031747 A1 | 10/2001 | deZiegler et al. |
| 2001/0032125 A1 | 10/2001 | Bhan et al. |
| 2001/0034340 A1 | 10/2001 | Pickar |
| 2001/0053383 A1 | 12/2001 | Miranda et al. |
| 2001/0056068 A1 | 12/2001 | Chwalisz et al. |
| 2002/0012710 A1 | 1/2002 | Lansky |
| 2002/0026158 A1 | 2/2002 | Rathbone et al. |
| 2002/0028788 A1 | 3/2002 | Bunt et al. |
| 2002/0035070 A1 | 3/2002 | Gardlik et al. |
| 2002/0058648 A1 | 5/2002 | Hammerly |
| 2002/0058926 A1 | 5/2002 | Rathbone et al. |
| 2002/0064541 A1 | 5/2002 | Lapidot et al. |
| 2002/0076441 A1 | 6/2002 | Shin et al. |
| 2002/0102308 A1 | 8/2002 | Wei et al. |
| 2002/0107230 A1 | 8/2002 | Waldon et al. |
| 2002/0114803 A1 | 8/2002 | Deaver et al. |
| 2002/0119174 A1 | 8/2002 | Gardlik et al. |
| 2002/0119198 A1 | 8/2002 | Gao et al. |
| 2002/0132801 A1 | 9/2002 | Heil et al. |
| 2002/0137749 A1 | 9/2002 | Levinson et al. |
| 2002/0142017 A1 | 10/2002 | Simonnet |
| 2002/0151530 A1 | 10/2002 | Leonard et al. |
| 2002/0156394 A1 | 10/2002 | Mehrotra et al. |
| 2002/0169150 A1 | 11/2002 | Pickar |
| 2002/0169205 A1 | 11/2002 | Chwalisz et al. |
| 2002/0173510 A1 | 11/2002 | Levinson et al. |
| 2002/0193356 A1 | 12/2002 | Van Beek et al. |
| 2002/0193758 A1 | 12/2002 | Sandberg |
| 2002/0197286 A1 | 12/2002 | Brandman et al. |
| 2003/0003139 A1 | 1/2003 | Lipp et al. |
| 2003/0004145 A1 | 1/2003 | Leonard |
| 2003/0007994 A1 | 1/2003 | Bunt et al. |
| 2003/0027772 A1 | 2/2003 | Breton |
| 2003/0044453 A1 | 3/2003 | Dittgen et al. |
| 2003/0049307 A1 | 3/2003 | Gyurik |
| 2003/0064097 A1 | 4/2003 | Patel et al. |
| 2003/0064975 A1 | 4/2003 | Koch et al. |
| 2003/0072760 A1 | 4/2003 | Sirbasku |
| 2003/0073248 A1 | 4/2003 | Roth et al. |
| 2003/0073673 A1 | 4/2003 | Hesch |
| 2003/0077297 A1 | 4/2003 | Chen et al. |
| 2003/0078245 A1 | 4/2003 | Bennink et al. |
| 2003/0091620 A1 | 5/2003 | Fikstad et al. |
| 2003/0091640 A1 | 5/2003 | Ramanathan et al. |
| 2003/0092691 A1 | 5/2003 | Besse et al. |
| 2003/0096012 A1 | 5/2003 | Besse et al. |
| 2003/0104048 A1 | 6/2003 | Patel et al. |
| 2003/0109507 A1 | 6/2003 | Franke et al. |
| 2003/0113268 A1 | 6/2003 | Buenafae et al. |
| 2003/0114420 A1 | 6/2003 | Salvati et al. |
| 2003/0114430 A1 | 6/2003 | MacLeod et al. |
| 2003/0124182 A1 | 7/2003 | Shojaei et al. |
| 2003/0124191 A1 | 7/2003 | Besse et al. |
| 2003/0130558 A1 | 7/2003 | Massara et al. |
| 2003/0144258 A1 | 7/2003 | Heil et al. |
| 2003/0157157 A1 | 8/2003 | Luo et al. |
| 2003/0166509 A1 | 9/2003 | Edwards et al. |
| 2003/0170295 A1 | 9/2003 | Kim et al. |
| 2003/0175329 A1 | 9/2003 | Azarnoff et al. |
| 2003/0175333 A1 | 9/2003 | Shefer et al. |
| 2003/0180352 A1 | 9/2003 | Patel et al. |
| 2003/0181353 A1 | 9/2003 | Nyce |
| 2003/0181728 A1 | 9/2003 | Salvati et al. |
| 2003/0191096 A1 | 10/2003 | Leonard et al. |
| 2003/0195177 A1 | 10/2003 | Leonard et al. |
| 2003/0215496 A1 | 11/2003 | Patel et al. |
| 2003/0219402 A1 | 11/2003 | Rutter |
| 2003/0220297 A1 | 11/2003 | Berstein et al. |
| 2003/0224057 A1 | 12/2003 | Martin-Letellier et al. |
| 2003/0224059 A1 | 12/2003 | Lerner et al. |
| 2003/0225047 A1 | 12/2003 | Caubel et al. |
| 2003/0225048 A1 | 12/2003 | Caubel et al. |
| 2003/0225050 A1 | 12/2003 | Eichardt et al. |

(56) References Cited

U.S. PATENT DOCUMENTS

| | | |
|---|---|---|
| 2003/0228686 A1 | 12/2003 | Klausner et al. |
| 2003/0229057 A1 | 12/2003 | Caubel et al. |
| 2003/0235596 A1 | 12/2003 | Gao et al. |
| 2003/0236236 A1 | 12/2003 | Chen et al. |
| 2004/0009960 A1 | 1/2004 | Heil et al. |
| 2004/0022820 A1 | 2/2004 | Anderson |
| 2004/0034001 A1 | 2/2004 | Karara |
| 2004/0037881 A1 | 2/2004 | Guittard et al. |
| 2004/0039356 A1 | 2/2004 | Maki et al. |
| 2004/0043043 A1 | 3/2004 | Schlyter et al. |
| 2004/0043943 A1 | 3/2004 | Guittard et al. |
| 2004/0044080 A1 | 3/2004 | Place et al. |
| 2004/0048900 A1 | 3/2004 | Flood |
| 2004/0052824 A1 | 3/2004 | Abou Chacra-Vernet et al. |
| 2004/0073024 A1 | 4/2004 | Metcalf, III et al. |
| 2004/0077605 A1 | 4/2004 | Salvati et al. |
| 2004/0077606 A1 | 4/2004 | Salvati et al. |
| 2004/0087548 A1 | 5/2004 | Salvati et al. |
| 2004/0087564 A1 | 5/2004 | Wright et al. |
| 2004/0089308 A1 | 5/2004 | Welch |
| 2004/0092494 A9 | 5/2004 | Dudley |
| 2004/0092583 A1 | 5/2004 | Shanahan-Prendergast |
| 2004/0093261 A1 | 5/2004 | Jain et al. |
| 2004/0097468 A1 | 5/2004 | Wimalawansa |
| 2004/0101557 A1 | 5/2004 | Gibson et al. |
| 2004/0106542 A1 | 6/2004 | Deaver et al. |
| 2004/0110732 A1 | 6/2004 | Masini-Eteve et al. |
| 2004/0131670 A1 | 7/2004 | Gao |
| 2004/0138103 A1 | 7/2004 | Patt |
| 2004/0142012 A1 | 7/2004 | Bunt et al. |
| 2004/0146539 A1 | 7/2004 | Gupta |
| 2004/0146894 A1 | 7/2004 | Warrington et al. |
| 2004/0161435 A1 | 8/2004 | Gupta |
| 2004/0176324 A1 | 9/2004 | Salvati et al. |
| 2004/0176336 A1 | 9/2004 | Rodriguez |
| 2004/0185104 A1 | 9/2004 | Piao et al. |
| 2004/0191207 A1 | 9/2004 | Lipari et al. |
| 2004/0191276 A1 | 9/2004 | Muni |
| 2004/0198706 A1 | 10/2004 | Carrara et al. |
| 2004/0210280 A1 | 10/2004 | Liedtke |
| 2004/0213744 A1 | 10/2004 | Lulla et al. |
| 2004/0219124 A1 | 11/2004 | Gupta |
| 2004/0225140 A1 | 11/2004 | Fernandez et al. |
| 2004/0234606 A1 | 11/2004 | Levine et al. |
| 2004/0241219 A1 | 12/2004 | Hille et al. |
| 2004/0243437 A1 | 12/2004 | Grace et al. |
| 2004/0253319 A1 | 12/2004 | Netke et al. |
| 2004/0259817 A1 | 12/2004 | Waldon et al. |
| 2004/0266745 A1 | 12/2004 | Schwanitz et al. |
| 2005/0003003 A1 | 1/2005 | Basu et al. |
| 2005/0004088 A1 | 1/2005 | Hesch |
| 2005/0009800 A1 | 1/2005 | Thumbeck et al. |
| 2005/0014729 A1 | 1/2005 | Pulaski |
| 2005/0020550 A1 | 1/2005 | Morris et al. |
| 2005/0020552 A1 | 1/2005 | Aschkenasay et al. |
| 2005/0021009 A1 | 1/2005 | Massara et al. |
| 2005/0025833 A1 | 2/2005 | Aschkenasay et al. |
| 2005/0031651 A1 | 2/2005 | Gervais et al. |
| 2005/0042173 A1 | 2/2005 | Besse et al. |
| 2005/0042268 A1 | 2/2005 | Aschkenasay et al. |
| 2005/0048116 A1 | 3/2005 | Straub et al. |
| 2005/0054991 A1 | 3/2005 | Tobyn et al. |
| 2005/0079138 A1 | 4/2005 | Chickering, III et al. |
| 2005/0085453 A1 | 4/2005 | Govindarajan |
| 2005/0101579 A1 | 5/2005 | Shippen |
| 2005/0113350 A1 | 5/2005 | Duesterberg et al. |
| 2005/0118244 A1 | 6/2005 | Theobald et al. |
| 2005/0118272 A1 | 6/2005 | Besse et al. |
| 2005/0129756 A1 | 6/2005 | Podhaisky et al. |
| 2005/0152956 A1 | 7/2005 | Dudley |
| 2005/0153946 A1 | 7/2005 | Hirsh et al. |
| 2005/0164977 A1 | 7/2005 | Coelingh Bennink |
| 2005/0182105 A1 | 8/2005 | Nirschl et al. |
| 2005/0186141 A1 | 8/2005 | Gonda et al. |
| 2005/0187267 A1 | 8/2005 | Hamann et al. |
| 2005/0192253 A1 | 9/2005 | Salvati et al. |
| 2005/0192310 A1 | 9/2005 | Gavai et al. |
| 2005/0196434 A1 | 9/2005 | Brierre |
| 2005/0207990 A1 | 9/2005 | Funke et al. |
| 2005/0209209 A1 | 9/2005 | Koch et al. |
| 2005/0214384 A1 | 9/2005 | Juturu et al. |
| 2005/0220825 A1 | 10/2005 | Funke et al. |
| 2005/0220900 A1 | 10/2005 | Popp et al. |
| 2005/0222106 A1 | 10/2005 | Bracht |
| 2005/0228692 A1 | 10/2005 | Hodgdon |
| 2005/0228718 A1 | 10/2005 | Austin |
| 2005/0239747 A1 | 10/2005 | Yang et al. |
| 2005/0239758 A1 | 10/2005 | Roby |
| 2005/0244360 A1 | 11/2005 | Billoni |
| 2005/0244522 A1 | 11/2005 | Carrara et al. |
| 2005/0245902 A1 | 11/2005 | Cornish et al. |
| 2005/0250746 A1 | 11/2005 | Iammatteo |
| 2005/0250750 A1 | 11/2005 | Cummings et al. |
| 2005/0250753 A1 | 11/2005 | Fink et al. |
| 2005/0256028 A1 | 11/2005 | Yun et al. |
| 2005/0266078 A1 | 12/2005 | Jorda et al. |
| 2005/0266088 A1 | 12/2005 | Hinrichs et al. |
| 2005/0271597 A1 | 12/2005 | Keith |
| 2005/0271598 A1 | 12/2005 | Friedman et al. |
| 2005/0272685 A1 | 12/2005 | Hung |
| 2005/0272712 A1 | 12/2005 | Grubb et al. |
| 2006/0009428 A1 | 1/2006 | Grubb et al. |
| 2006/0014728 A1 | 1/2006 | Chwalisz et al. |
| 2006/0018937 A1 | 1/2006 | Friedman et al. |
| 2006/0019978 A1 | 1/2006 | Balog |
| 2006/0020002 A1 | 1/2006 | Salvati et al. |
| 2006/0030615 A1 | 2/2006 | Fensome et al. |
| 2006/0034889 A1 | 2/2006 | Jo et al. |
| 2006/0034904 A1 | 2/2006 | Weimann |
| 2006/0051391 A1 | 3/2006 | Dvoskin et al. |
| 2006/0052341 A1 | 3/2006 | Cornish et al. |
| 2006/0069031 A1 | 3/2006 | Loumaye |
| 2006/0078618 A1 | 4/2006 | Constantinides et al. |
| 2006/0083778 A1 | 4/2006 | Allison et al. |
| 2006/0084704 A1 | 4/2006 | Shih et al. |
| 2006/0088580 A1 | 4/2006 | Meconi et al. |
| 2006/0089337 A1 | 4/2006 | Casper et al. |
| 2006/0093678 A1 | 5/2006 | Chickering, III et al. |
| 2006/0100180 A1 | 5/2006 | Nubbemeyer et al. |
| 2006/0106004 A1 | 5/2006 | Brody et al. |
| 2006/0110415 A1 | 5/2006 | Gupta |
| 2006/0111424 A1 | 5/2006 | Salvati et al. |
| 2006/0121102 A1 | 6/2006 | Chiang |
| 2006/0121626 A1 | 6/2006 | Imrich |
| 2006/0134188 A1 | 6/2006 | Podhaisky et al. |
| 2006/0135619 A1 | 6/2006 | Kick et al. |
| 2006/0165744 A1 | 7/2006 | Jamil et al. |
| 2006/0193789 A1 | 8/2006 | Tamarkin et al. |
| 2006/0194775 A1 | 8/2006 | Tofovic et al. |
| 2006/0204557 A1 | 9/2006 | Gupta et al. |
| 2006/0233743 A1 | 10/2006 | Kelly |
| 2006/0233841 A1 | 10/2006 | Brodbeck et al. |
| 2006/0235037 A1 | 10/2006 | Purandare et al. |
| 2006/0240111 A1 | 10/2006 | Fernandez et al. |
| 2006/0246122 A1 | 11/2006 | Langguth et al. |
| 2006/0247216 A1 | 11/2006 | Haj-Yehia |
| 2006/0247221 A1 | 11/2006 | Coelingh Bennink et al. |
| 2006/0251581 A1 | 11/2006 | McIntyre et al. |
| 2006/0252049 A1 | 11/2006 | Shuler et al. |
| 2006/0257472 A1 | 11/2006 | Neilsen |
| 2006/0275218 A1 | 12/2006 | Tamarkin et al. |
| 2006/0275360 A1 | 12/2006 | Ahmed et al. |
| 2006/0276414 A1 | 12/2006 | Coelingh Bennink et al. |
| 2006/0280771 A1 | 12/2006 | Groenewegen et al. |
| 2006/0280797 A1 | 12/2006 | Shoichet et al. |
| 2006/0280800 A1 | 12/2006 | Nagi et al. |
| 2006/0292223 A1 | 12/2006 | Woolfson et al. |
| 2007/0004693 A1 | 1/2007 | Woolfson et al. |
| 2007/0004694 A1 | 1/2007 | Woolfson et al. |
| 2007/0009559 A1 | 1/2007 | Li et al. |
| 2007/0009594 A1 | 1/2007 | Grubb et al. |
| 2007/0010550 A1 | 1/2007 | McKenzie |
| 2007/0014839 A1 | 1/2007 | Bracht |
| 2007/0015698 A1 | 1/2007 | Kleinman et al. |

(56) References Cited

U.S. PATENT DOCUMENTS

| | | |
|---|---|---|
| 2007/0021360 A1 | 1/2007 | Nyce et al. |
| 2007/0027201 A1 | 2/2007 | McComas et al. |
| 2007/0031491 A1 | 2/2007 | Levine et al. |
| 2007/0037780 A1 | 2/2007 | Ebert et al. |
| 2007/0037782 A1 | 2/2007 | Hibino et al. |
| 2007/0042038 A1 | 2/2007 | Besse |
| 2007/0060589 A1 | 3/2007 | Purandare et al. |
| 2007/0066628 A1 | 3/2007 | Zhang et al. |
| 2007/0066637 A1 | 3/2007 | Zhang et al. |
| 2007/0066675 A1 | 3/2007 | Zhang et al. |
| 2007/0078091 A1 | 4/2007 | Hubler et al. |
| 2007/0088029 A1 | 4/2007 | Balog et al. |
| 2007/0093548 A1 | 4/2007 | Diffendal et al. |
| 2007/0116729 A1 | 5/2007 | Palepu |
| 2007/0116829 A1 | 5/2007 | Prakash et al. |
| 2007/0128263 A1 | 6/2007 | Gargiulo et al. |
| 2007/0154533 A1 | 7/2007 | Dudley |
| 2007/0167418 A1 | 7/2007 | Ferguson |
| 2007/0178166 A1 | 8/2007 | Bernstein et al. |
| 2007/0184558 A1 | 8/2007 | Roth et al. |
| 2007/0185068 A1 | 8/2007 | Ferguson et al. |
| 2007/0190022 A1 | 8/2007 | Bacopoulos et al. |
| 2007/0191319 A1 | 8/2007 | Ke et al. |
| 2007/0196415 A1 | 8/2007 | Chen et al. |
| 2007/0196433 A1 | 8/2007 | Ron et al. |
| 2007/0207225 A1 | 9/2007 | Squadrito |
| 2007/0225281 A1 | 9/2007 | Zhang et al. |
| 2007/0232574 A1 | 10/2007 | Galey et al. |
| 2007/0238713 A1 | 10/2007 | Gast et al. |
| 2007/0243229 A1 | 10/2007 | Smith et al. |
| 2007/0248658 A1 | 10/2007 | Zurdo Schroeder et al. |
| 2007/0254858 A1 | 11/2007 | Cronk |
| 2007/0255197 A1 | 11/2007 | Humberstone et al. |
| 2007/0264309 A1 | 11/2007 | Chollet et al. |
| 2007/0264345 A1 | 11/2007 | Eros et al. |
| 2007/0264349 A1 | 11/2007 | Lee et al. |
| 2007/0286819 A1 | 12/2007 | DeVries et al. |
| 2007/0287688 A1 | 12/2007 | Chan et al. |
| 2007/0287789 A1 | 12/2007 | Jones et al. |
| 2007/0292359 A1 | 12/2007 | Friedman et al. |
| 2007/0292387 A1 | 12/2007 | Jon et al. |
| 2007/0292461 A1 | 12/2007 | Tamarkin et al. |
| 2007/0292493 A1 | 12/2007 | Brierre |
| 2007/0298089 A1 | 12/2007 | Saeki et al. |
| 2008/0026035 A1 | 1/2008 | Chollet et al. |
| 2008/0026040 A1 | 1/2008 | Farr et al. |
| 2008/0026062 A1 | 1/2008 | Farr et al. |
| 2008/0038219 A1 | 2/2008 | Mosbaugh et al. |
| 2008/0038350 A1 | 2/2008 | Gerecke et al. |
| 2008/0039405 A1 | 2/2008 | Langley et al. |
| 2008/0050317 A1 | 2/2008 | Tamarkin et al. |
| 2008/0051351 A1 | 2/2008 | Ghisalberti |
| 2008/0063607 A1 | 3/2008 | Tamarkin et al. |
| 2008/0069779 A1 | 3/2008 | Tamarkin et al. |
| 2008/0069791 A1 | 3/2008 | Beissert |
| 2008/0085877 A1 | 4/2008 | Bortz |
| 2008/0095831 A1 | 4/2008 | McGraw |
| 2008/0095838 A1 | 4/2008 | Abou Chacra-Vernet |
| 2008/0113953 A1 | 5/2008 | De Vries et al. |
| 2008/0114050 A1 | 5/2008 | Fensome et al. |
| 2008/0119537 A1 | 5/2008 | Zhang et al. |
| 2008/0125402 A1 | 5/2008 | Dilberti |
| 2008/0138379 A1 | 6/2008 | Jennings-Spring |
| 2008/0138390 A1 | 6/2008 | Hsu et al. |
| 2008/0139392 A1 | 6/2008 | Acosta-Zara et al. |
| 2008/0145423 A1 | 6/2008 | Khan et al. |
| 2008/0153789 A1 | 6/2008 | Dmowski et al. |
| 2008/0175814 A1 | 7/2008 | Phiasivongsa et al. |
| 2008/0175905 A1 | 7/2008 | Liu et al. |
| 2008/0175908 A1 | 7/2008 | Liu et al. |
| 2008/0188829 A1 | 8/2008 | Creasy |
| 2008/0206156 A1 | 8/2008 | Cronk |
| 2008/0206159 A1 | 8/2008 | Tamarkin et al. |
| 2008/0206161 A1 | 8/2008 | Tamarkin et al. |
| 2008/0214512 A1 | 9/2008 | Seitz et al. |
| 2008/0220069 A1 | 9/2008 | Allison |
| 2008/0226698 A1 | 9/2008 | Tang et al. |
| 2008/0227763 A1 | 9/2008 | Lanquetin et al. |
| 2008/0234199 A1 | 9/2008 | Katamreddy |
| 2008/0234240 A1 | 9/2008 | Duesterberg et al. |
| 2008/0255078 A1 | 10/2008 | Katamreddy |
| 2008/0255089 A1 | 10/2008 | Katamreddy |
| 2008/0261931 A1 | 10/2008 | Hedner et al. |
| 2008/0299220 A1 | 12/2008 | Tamarkin et al. |
| 2008/0306036 A1 | 12/2008 | Katamreddy |
| 2008/0312197 A1 | 12/2008 | Rodriguez |
| 2008/0312198 A1 | 12/2008 | Rodriguez |
| 2008/0319078 A1 | 12/2008 | Katamreddy |
| 2009/0004246 A1 | 1/2009 | Woolfson et al. |
| 2009/0010968 A1 | 1/2009 | Allart et al. |
| 2009/0011041 A1 | 1/2009 | Musaeva et al. |
| 2009/0017120 A1 | 1/2009 | Trimble et al. |
| 2009/0022683 A1 | 1/2009 | Song et al. |
| 2009/0047357 A1 | 2/2009 | Tomohira et al. |
| 2009/0053294 A1 | 2/2009 | Prendergast |
| 2009/0060982 A1 | 3/2009 | Ron et al. |
| 2009/0060997 A1 | 3/2009 | Seitz et al. |
| 2009/0068118 A1 | 3/2009 | Eini et al. |
| 2009/0074859 A1 | 3/2009 | Patel |
| 2009/0081206 A1 | 3/2009 | Leibovitz |
| 2009/0081278 A1 | 3/2009 | De Graaff et al. |
| 2009/0081303 A1 | 3/2009 | Savoir et al. |
| 2009/0092656 A1 | 4/2009 | Klamerus et al. |
| 2009/0093440 A1 | 4/2009 | Murad |
| 2009/0098069 A1 | 4/2009 | Vacca |
| 2009/0099106 A1 | 4/2009 | Phiasivongsa et al. |
| 2009/0099149 A1 | 4/2009 | Liu et al. |
| 2009/0130029 A1 | 5/2009 | Tamarkin et al. |
| 2009/0131385 A1 | 5/2009 | Voskuhl |
| 2009/0137478 A1 | 5/2009 | Bernstein et al. |
| 2009/0137538 A1 | 5/2009 | Klamerus et al. |
| 2009/0143344 A1 | 6/2009 | Chang |
| 2009/0164341 A1 | 6/2009 | Sunvold et al. |
| 2009/0175799 A1 | 7/2009 | Tamarkin et al. |
| 2009/0181088 A1 | 7/2009 | Song et al. |
| 2009/0186081 A1 | 7/2009 | Holm et al. |
| 2009/0197843 A1 | 8/2009 | Notelovitz et al. |
| 2009/0203658 A1 | 8/2009 | Marx et al. |
| 2009/0214474 A1 | 8/2009 | Jennings |
| 2009/0227025 A1 | 9/2009 | Nichols et al. |
| 2009/0227550 A1 | 9/2009 | Mattern |
| 2009/0232897 A1 | 9/2009 | Sahoo et al. |
| 2009/0258096 A1 | 10/2009 | Cohen |
| 2009/0264395 A1 | 10/2009 | Creasy |
| 2009/0269403 A1 | 10/2009 | Shaked et al. |
| 2009/0285772 A1 | 11/2009 | Phiasivongsa et al. |
| 2009/0285869 A1 | 11/2009 | Trimble |
| 2009/0318558 A1 | 12/2009 | Kim et al. |
| 2009/0324714 A1 | 12/2009 | Liu et al. |
| 2009/0325916 A1 | 12/2009 | Zhang et al. |
| 2010/0008985 A1 | 1/2010 | Pellikaan et al. |
| 2010/0028360 A1 | 2/2010 | Atwood |
| 2010/0034838 A1 | 2/2010 | Staniforth et al. |
| 2010/0034880 A1 | 2/2010 | Sintov et al. |
| 2010/0040671 A1 | 2/2010 | Ahmed et al. |
| 2010/0048523 A1 | 2/2010 | Bachman et al. |
| 2010/0055138 A1 | 3/2010 | Margulies et al. |
| 2010/0074959 A1 | 3/2010 | Hansom et al. |
| 2010/0086501 A1 | 4/2010 | Chang et al. |
| 2010/0086599 A1 | 4/2010 | Huempel et al. |
| 2010/0092568 A1 | 4/2010 | Lerner et al. |
| 2010/0105071 A1 | 4/2010 | Laufer et al. |
| 2010/0119585 A1 | 5/2010 | Hille et al. |
| 2010/0129320 A1 | 5/2010 | Phiasivongsa et al. |
| 2010/0136105 A1 | 6/2010 | Chen et al. |
| 2010/0137265 A1 | 6/2010 | Leonard |
| 2010/0137271 A1 | 6/2010 | Chen et al. |
| 2010/0143420 A1 | 6/2010 | Shenoy et al. |
| 2010/0143481 A1 | 6/2010 | Shenoy et al. |
| 2010/0150993 A1 | 6/2010 | Theobald et al. |
| 2010/0152144 A1 | 6/2010 | Hermsmeyer |
| 2010/0168228 A1 | 7/2010 | Bose et al. |
| 2010/0183723 A1 | 7/2010 | Laurent-Applegate et al. |
| 2010/0184736 A1 | 7/2010 | Coelingh Bennink et al. |

(56) References Cited

U.S. PATENT DOCUMENTS

| | | |
|---|---|---|
| 2010/0190758 A1 | 7/2010 | Fauser et al. |
| 2010/0204326 A1 | 8/2010 | D'Souza |
| 2010/0210994 A1 | 8/2010 | Zarif |
| 2010/0221195 A1 | 9/2010 | Tamarkin et al. |
| 2010/0227797 A1 | 9/2010 | Axelson et al. |
| 2010/0240626 A1 | 9/2010 | Kulkarni et al. |
| 2010/0247482 A1 | 9/2010 | Cui et al. |
| 2010/0247632 A1 | 9/2010 | Dong et al. |
| 2010/0247635 A1 | 9/2010 | Rosenberg et al. |
| 2010/0255085 A1 | 10/2010 | Liu et al. |
| 2010/0273730 A1 | 10/2010 | Hsu et al. |
| 2010/0278759 A1 | 11/2010 | Murad |
| 2010/0279988 A1 | 11/2010 | Setiawan et al. |
| 2010/0291191 A1 | 11/2010 | Shoichet et al. |
| 2010/0292199 A1 | 11/2010 | Leverd et al. |
| 2010/0303825 A9 | 12/2010 | Sirbasku |
| 2010/0312137 A1 | 12/2010 | Gilmour et al. |
| 2010/0316724 A1 | 12/2010 | Whitfield et al. |
| 2010/0322884 A1 | 12/2010 | Dipietro et al. |
| 2010/0330168 A1 | 12/2010 | Gicquel et al. |
| 2011/0028439 A1 | 2/2011 | Witt-Enderby et al. |
| 2011/0039814 A1 | 2/2011 | Huatan et al. |
| 2011/0053845 A1 | 3/2011 | Levine et al. |
| 2011/0066473 A1 | 3/2011 | Bernick et al. |
| 2011/0076775 A1 | 3/2011 | Stewart et al. |
| 2011/0076776 A1 | 3/2011 | Stewart et al. |
| 2011/0086825 A1 | 4/2011 | Chatroux |
| 2011/0087192 A1 | 4/2011 | Uhland et al. |
| 2011/0091555 A1 | 4/2011 | De Luigi Bruschi et al. |
| 2011/0098258 A1 | 4/2011 | Masini-Eteve et al. |
| 2011/0098631 A1 | 4/2011 | McIntyre et al. |
| 2011/0104268 A1 | 5/2011 | Pachot et al. |
| 2011/0104289 A1 | 5/2011 | Savoir Vilboeuf et al. |
| 2011/0130372 A1 | 6/2011 | Agostinacchio et al. |
| 2011/0135719 A1 | 6/2011 | Besins et al. |
| 2011/0142945 A1 | 6/2011 | Chen et al. |
| 2011/0152840 A1 | 6/2011 | Lee et al. |
| 2011/0158920 A1 | 6/2011 | Morley et al. |
| 2011/0171140 A1 | 7/2011 | Illum et al. |
| 2011/0182997 A1 | 7/2011 | Lewis et al. |
| 2011/0190201 A1 | 8/2011 | Hyde et al. |
| 2011/0195031 A1 | 8/2011 | Du |
| 2011/0195114 A1 | 8/2011 | Carrara et al. |
| 2011/0195944 A1 | 8/2011 | Mura et al. |
| 2011/0217341 A1 | 9/2011 | Sah |
| 2011/0238003 A1 | 9/2011 | Bruno-Raimondi et al. |
| 2011/0244043 A1 | 10/2011 | Xu et al. |
| 2011/0250256 A1 | 10/2011 | Hyun-Oh et al. |
| 2011/0250259 A1 | 10/2011 | Buckman |
| 2011/0250274 A1 | 10/2011 | Shaked et al. |
| 2011/0256092 A1 | 10/2011 | Phiasivongsa et al. |
| 2011/0262373 A1 | 10/2011 | Umbert Millet |
| 2011/0262494 A1 | 10/2011 | Achleitner et al. |
| 2011/0268665 A1 | 11/2011 | Tamarkin et al. |
| 2011/0275584 A1 | 11/2011 | Wilckens et al. |
| 2011/0281832 A1 | 11/2011 | Li et al. |
| 2011/0287094 A1 | 11/2011 | Penhasi et al. |
| 2011/0293720 A1 | 12/2011 | General et al. |
| 2011/0294738 A1 | 12/2011 | Ren et al. |
| 2011/0300167 A1 | 12/2011 | McMurry et al. |
| 2011/0301087 A1 | 12/2011 | McBride et al. |
| 2011/0306579 A1 | 12/2011 | Stein |
| 2011/0311592 A1 | 12/2011 | Birbara |
| 2011/0312927 A1 | 12/2011 | Nachaegari et al. |
| 2011/0312928 A1 | 12/2011 | Nachaegari et al. |
| 2011/0318405 A1 | 12/2011 | Erwin |
| 2011/0318431 A1 | 12/2011 | Gulati |
| 2012/0009276 A1 | 1/2012 | De Groote |
| 2012/0015350 A1 | 1/2012 | Nabatiyan et al. |
| 2012/0021041 A1 | 1/2012 | Rossi et al. |
| 2012/0028888 A1 | 2/2012 | Janz et al. |
| 2012/0028910 A1 | 2/2012 | Combal et al. |
| 2012/0028936 A1 | 2/2012 | Gloger et al. |
| 2012/0045532 A1 | 2/2012 | Cohen |
| 2012/0046264 A1 | 2/2012 | Simes et al. |
| 2012/0046518 A1 | 2/2012 | Yoakum et al. |
| 2012/0052077 A1 | 3/2012 | Truitt, III et al. |
| 2012/0058171 A1 | 3/2012 | De Graaff et al. |
| 2012/0058962 A1 | 3/2012 | Cumming et al. |
| 2012/0058979 A1 | 3/2012 | Keith et al. |
| 2012/0064135 A1 | 3/2012 | Levin et al. |
| 2012/0065179 A1 | 3/2012 | Andersson |
| 2012/0065221 A1 | 3/2012 | Babul |
| 2012/0087872 A1 | 4/2012 | Tamarkin et al. |
| 2012/0101073 A1 | 4/2012 | Mannion et al. |
| 2012/0121517 A1 | 5/2012 | Song et al. |
| 2012/0121692 A1 | 5/2012 | Xu et al. |
| 2012/0122829 A1 | 5/2012 | Taravella et al. |
| 2012/0128625 A1 | 5/2012 | Shalwitz et al. |
| 2012/0128654 A1 | 5/2012 | Terpstra et al. |
| 2012/0128683 A1 | 5/2012 | Shantha |
| 2012/0128733 A1 | 5/2012 | Perrin et al. |
| 2012/0128777 A1 | 5/2012 | Keck et al. |
| 2012/0129773 A1 | 5/2012 | Geier et al. |
| 2012/0129819 A1 | 5/2012 | Vancaillie et al. |
| 2012/0136013 A1 | 5/2012 | Li et al. |
| 2012/0142645 A1 | 6/2012 | Marx |
| 2012/0148670 A1 | 6/2012 | Kim et al. |
| 2012/0149748 A1 | 6/2012 | Shanler et al. |
| 2012/0172343 A1 | 7/2012 | Lindenthal et al. |
| 2012/0184515 A1 | 7/2012 | Klar et al. |
| 2012/0231052 A1 | 9/2012 | Sitruk-Ware et al. |
| 2012/0232011 A1 | 9/2012 | Kneissel et al. |
| 2012/0232042 A1 | 9/2012 | Klar et al. |
| 2012/0263679 A1 | 10/2012 | Marlow et al. |
| 2012/0269721 A1 | 10/2012 | Weng et al. |
| 2012/0269878 A2 | 10/2012 | Cantor et al. |
| 2012/0277249 A1 | 11/2012 | Andersson et al. |
| 2012/0277727 A1 | 11/2012 | Doshi et al. |
| 2012/0283671 A1 | 11/2012 | Shibata et al. |
| 2012/0295911 A1 | 11/2012 | Mannion et al. |
| 2012/0301517 A1 | 11/2012 | Zhang et al. |
| 2012/0301538 A1 | 11/2012 | Gordon-Beresford et al. |
| 2012/0302535 A1 | 11/2012 | Caufriez et al. |
| 2012/0316130 A1 | 12/2012 | Hendrix |
| 2012/0316496 A1 | 12/2012 | Hoffmann et al. |
| 2012/0321579 A1 | 12/2012 | Edelson et al. |
| 2012/0322779 A9 | 12/2012 | Voskuhl |
| 2012/0328549 A1 | 12/2012 | Edelson et al. |
| 2012/0329738 A1 | 12/2012 | Liu |
| 2013/0004619 A1 | 1/2013 | Chow et al. |
| 2013/0011342 A1 | 1/2013 | Tamarkin et al. |
| 2013/0017239 A1 | 1/2013 | Viladot Petit et al. |
| 2013/0022674 A1 | 1/2013 | Dudley et al. |
| 2013/0023505 A1 | 1/2013 | Garfield et al. |
| 2013/0023823 A1 | 1/2013 | Simpson et al. |
| 2013/0028850 A1 | 1/2013 | Tamarkin et al. |
| 2013/0029947 A1 | 1/2013 | Nachaegari et al. |
| 2013/0029957 A1 | 1/2013 | Giliyar et al. |
| 2013/0045266 A1 | 2/2013 | Choi et al. |
| 2013/0045953 A1 | 2/2013 | Sitruk-Ware et al. |
| 2013/0059795 A1 | 3/2013 | Lo et al. |
| 2013/0064897 A1 | 3/2013 | Binay |
| 2013/0072466 A1 | 3/2013 | Choi et al. |
| 2013/0084257 A1 | 4/2013 | Ishida et al. |
| 2013/0085123 A1 | 4/2013 | Li et al. |
| 2013/0089574 A1 | 4/2013 | Schmidt-Gollwitzer et al. |
| 2013/0090318 A1 | 4/2013 | Ulmann et al. |
| 2013/0102781 A1 | 4/2013 | Bevill et al. |
| 2013/0108551 A1 | 5/2013 | Langereis et al. |
| 2013/0116215 A1 | 5/2013 | Coma et al. |
| 2013/0116222 A1 | 5/2013 | Arnold et al. |
| 2013/0122051 A1 | 5/2013 | Abidi et al. |
| 2013/0123175 A1 | 5/2013 | Hill et al. |
| 2013/0123220 A1 | 5/2013 | Queiroz |
| 2013/0123351 A1 | 5/2013 | Dewitt |
| 2013/0129818 A1 | 5/2013 | Bernick et al. |
| 2013/0131027 A1 | 5/2013 | Pakkalin et al. |
| 2013/0131028 A1 | 5/2013 | Snyder et al. |
| 2013/0131029 A1 | 5/2013 | Bakker et al. |
| 2013/0149314 A1 | 6/2013 | Bullerdiek et al. |
| 2013/0164225 A1 | 6/2013 | Tamarkin et al. |
| 2013/0164346 A1 | 6/2013 | Lee et al. |
| 2013/0165744 A1 | 6/2013 | Carson et al. |

(56) References Cited

U.S. PATENT DOCUMENTS

| | | |
|---|---|---|
| 2013/0178452 A1 | 7/2013 | King |
| 2013/0183254 A1 | 7/2013 | Zhou et al. |
| 2013/0183325 A1 | 7/2013 | Bottoni et al. |
| 2013/0189193 A1 | 7/2013 | Tamarkin et al. |
| 2013/0189196 A1 | 7/2013 | Tamarkin et al. |
| 2013/0189230 A1 | 7/2013 | Shoichet et al. |
| 2013/0189368 A1 | 7/2013 | Mosqueira et al. |
| 2013/0210709 A1 | 8/2013 | McMurry et al. |
| 2013/0216550 A1 | 8/2013 | Penninger et al. |
| 2013/0216596 A1 | 8/2013 | Viladot Petit et al. |
| 2013/0224177 A1 | 8/2013 | Kim et al. |
| 2013/0224257 A1 | 8/2013 | Sah et al. |
| 2013/0224268 A1 | 8/2013 | Alam et al. |
| 2013/0224300 A1 | 8/2013 | Maggio |
| 2013/0225412 A1 | 8/2013 | Sardari Lodriche et al. |
| 2013/0225542 A1 | 8/2013 | Poegh et al. |
| 2013/0226113 A1 | 8/2013 | Schumacher et al. |
| 2013/0243696 A1 | 9/2013 | Wang et al. |
| 2013/0245253 A1 | 9/2013 | Marx et al. |
| 2013/0245570 A1 | 9/2013 | Jackson |
| 2013/0261096 A1 | 10/2013 | Merian et al. |
| 2013/0266645 A1 | 10/2013 | Becker et al. |
| 2013/0267485 A1 | 10/2013 | Da Silva Maia Filho |
| 2013/0273167 A1 | 10/2013 | Lee et al. |
| 2013/0274211 A1 | 10/2013 | Burman et al. |
| 2013/0280213 A1 | 10/2013 | Voskuhl |
| 2013/0316374 A1 | 11/2013 | Penninger et al. |
| 2013/0317065 A1 | 11/2013 | Tatani et al. |
| 2013/0317315 A1 | 11/2013 | Lu et al. |
| 2013/0324565 A1 | 12/2013 | Li et al. |
| 2013/0331363 A1 | 12/2013 | Li et al. |
| 2013/0338122 A1 | 12/2013 | Bernick et al. |
| 2013/0338123 A1 | 12/2013 | Bernick et al. |
| 2013/0338124 A1 | 12/2013 | Li et al. |
| 2013/0345187 A1 | 12/2013 | Rodriguez Oquendo |
| 2014/0018335 A1 | 1/2014 | Tatani et al. |
| 2014/0024590 A1 | 1/2014 | Weidhaas et al. |
| 2014/0031289 A1 | 1/2014 | Song et al. |
| 2014/0031323 A1 | 1/2014 | Perez |
| 2014/0066416 A1 | 3/2014 | Leunis et al. |
| 2014/0072531 A1 | 3/2014 | Kim et al. |
| 2014/0079686 A1 | 3/2014 | Barman et al. |
| 2014/0088051 A1 | 3/2014 | Bernick et al. |
| 2014/0088058 A1 | 3/2014 | Maurizio |
| 2014/0088059 A1 | 3/2014 | Perumal et al. |
| 2014/0094426 A1 | 4/2014 | Drummond et al. |
| 2014/0094440 A1 | 4/2014 | Bernick et al. |
| 2014/0094441 A1 | 4/2014 | Bernick et al. |
| 2014/0099362 A1 | 4/2014 | Bernick et al. |
| 2014/0100159 A1 | 4/2014 | Conrad |
| 2014/0100204 A1 | 4/2014 | Bernick et al. |
| 2014/0100205 A1 | 4/2014 | Bernick et al. |
| 2014/0100206 A1 | 4/2014 | Bernick et al. |
| 2014/0113889 A1 | 4/2014 | Connor et al. |
| 2014/0127185 A1 | 5/2014 | Stein et al. |
| 2014/0127280 A1 | 5/2014 | Duesterberg et al. |
| 2014/0127308 A1 | 5/2014 | Opara et al. |
| 2014/0128798 A1 | 5/2014 | Janson et al. |
| 2014/0148491 A1 | 5/2014 | Valia et al. |
| 2014/0186332 A1 | 7/2014 | Ezrin et al. |
| 2014/0187487 A1 | 7/2014 | Shoichet et al. |
| 2014/0193523 A1 | 7/2014 | Henry |
| 2014/0194396 A1 | 7/2014 | Li et al. |
| 2014/0206616 A1 | 7/2014 | Ko et al. |
| 2014/0213565 A1 | 7/2014 | Bernick et al. |
| 2014/0288035 A1 | 9/2014 | Hubner et al. |
| 2014/0329783 A1 | 11/2014 | Bernick et al. |
| 2014/0335193 A1 | 11/2014 | Rintoul et al. |
| 2014/0370084 A1 | 12/2014 | Bernick et al. |
| 2014/0371182 A1 | 12/2014 | Bernick et al. |
| 2014/0371183 A1 | 12/2014 | Bernick et al. |
| 2014/0371184 A1 | 12/2014 | Bernick et al. |
| 2014/0371185 A1 | 12/2014 | Bernick et al. |
| 2015/0031654 A1 | 1/2015 | Amadio |
| 2015/0045335 A1 | 2/2015 | Bernick et al. |
| 2015/0133421 A1 | 5/2015 | Bernick et al. |
| 2015/0196640 A1 | 7/2015 | Cacase et al. |
| 2015/0202211 A1 | 7/2015 | Amadio et al. |
| 2017/0340739 A1 | 11/2017 | Cacace et al. |

FOREIGN PATENT DOCUMENTS

| | | |
|---|---|---|
| CA | 2856520 A1 | 5/2013 |
| CN | 102258455 | 11/2011 |
| CN | 102258455 A | 11/2011 |
| EP | 0275716 A1 | 7/1988 |
| EP | 0622075 A1 | 11/1994 |
| EP | 0785211 A1 | 1/1996 |
| EP | 0785212 A1 | 1/1996 |
| EP | 0811381 A1 | 6/1997 |
| EP | 0785211 A1 | 7/1997 |
| EP | 0785212 A1 | 7/1997 |
| EP | 0811381 B1 | 5/2003 |
| EP | 1094781 B1 | 7/2006 |
| EP | 2191833 A1 | 6/2010 |
| EP | 2191833 B1 | 2/2013 |
| GB | 452238 A | 8/1936 |
| GB | 720561 | 12/1954 |
| GB | 720561 A | 12/1954 |
| GB | 848881 A | 9/1960 |
| GB | 874368 | 8/1961 |
| GB | 874368 A | 8/1961 |
| GB | 1589946 A | 5/1981 |
| IN | 216026 | 3/2008 |
| IN | 2005KO00053 | 9/2009 |
| IN | 244217 | 11/2010 |
| JP | 2007-516259 A | 6/2007 |
| JP | 2009-510127 A | 3/2009 |
| MX | 2014/006256 A | 10/2014 |
| WO | 1990011064 A1 | 10/1990 |
| WO | 1993017686 A1 | 9/1993 |
| WO | 1994022426 A1 | 3/1994 |
| WO | 1995030409 A1 | 11/1995 |
| WO | 1996009826 A2 | 4/1996 |
| WO | WO-9619975 A1 | 7/1996 |
| WO | 1996030000 A1 | 10/1996 |
| WO | 9705491 | 2/1997 |
| WO | 1997043989 A1 | 11/1997 |
| WO | 1998010293 A1 | 3/1998 |
| WO | 1998032465 A1 | 7/1998 |
| WO | 1998051280 A1 | 11/1998 |
| WO | 1999039700 A1 | 2/1999 |
| WO | 1999032072 A1 | 7/1999 |
| WO | 1999039700 A1 | 8/1999 |
| WO | 1999042109 A1 | 8/1999 |
| WO | 9943304 | 9/1999 |
| WO | 1999048477 A1 | 9/1999 |
| WO | 1999053910 A2 | 10/1999 |
| WO | 2000038659 A1 | 11/1999 |
| WO | 1999063974 A2 | 12/1999 |
| WO | 2000001351 A1 | 1/2000 |
| WO | 2000006175 A1 | 2/2000 |
| WO | 2000045795 A2 | 8/2000 |
| WO | 2000050007 A1 | 8/2000 |
| WO | 2000059577 A1 | 10/2000 |
| WO | 2001037808 A1 | 11/2000 |
| WO | 2000076522 A1 | 12/2000 |
| WO | 2002007700 A2 | 7/2001 |
| WO | 2001054699 A1 | 8/2001 |
| WO | 2001060325 A1 | 8/2001 |
| WO | 2002011768 A1 | 2/2002 |
| WO | 2002022132 A2 | 3/2002 |
| WO | 2002040008 A2 | 5/2002 |
| WO | WO-0241878 A2 | 5/2002 |
| WO | 2002053131 A1 | 7/2002 |
| WO | 2002078602 A3 | 2/2003 |
| WO | WO-03028667 A2 | 4/2003 |
| WO | 2003041718 A1 | 5/2003 |
| WO | 2003041741 A1 | 5/2003 |
| WO | 2003068186 A1 | 8/2003 |
| WO | 2003077923 A1 | 9/2003 |
| WO | 2003082254 A1 | 10/2003 |
| WO | 2002078604 A3 | 11/2003 |
| WO | 2003092588 A2 | 11/2003 |

(56) References Cited

FOREIGN PATENT DOCUMENTS

| | | |
|---|---|---|
| WO | WO-2004014397 A1 | 2/2004 |
| WO | WO-2004014432 A1 | 2/2004 |
| WO | 2004017983 A1 | 3/2004 |
| WO | 2005027911 A1 | 3/2004 |
| WO | 2004032897 A2 | 4/2004 |
| WO | 2004052336 A2 | 6/2004 |
| WO | 2005120517 A1 | 6/2004 |
| WO | 2004054540 A2 | 7/2004 |
| WO | 2004080413 A2 | 9/2004 |
| WO | 2005030175 A1 | 4/2005 |
| WO | 2005087194 A1 | 9/2005 |
| WO | 2005087199 A2 | 9/2005 |
| WO | WO-2005081825 A2 | 9/2005 |
| WO | 2005105059 A1 | 11/2005 |
| WO | 2005115335 A1 | 12/2005 |
| WO | 2005120470 A1 | 12/2005 |
| WO | 2005120517 A1 | 12/2005 |
| WO | 2006013369 A2 | 2/2006 |
| WO | 2006034090 A1 | 3/2006 |
| WO | 2006036899 A2 | 4/2006 |
| WO | 2006053172 A2 | 5/2006 |
| WO | 2006105615 A1 | 10/2006 |
| WO | 2006113505 A2 | 10/2006 |
| WO | 2006138686 A1 | 12/2006 |
| WO | 2006138735 A2 | 12/2006 |
| WO | 2007045027 A1 | 4/2007 |
| WO | WO 2007/038796 A1 | 4/2007 |
| WO | 2007103294 A2 | 9/2007 |
| WO | 2006138735 A3 | 10/2007 |
| WO | WO-2007120868 A2 | 10/2007 |
| WO | 2007123790 A1 | 11/2007 |
| WO | 2007124250 A2 | 11/2007 |
| WO | 2007124250 A3 | 12/2007 |
| WO | 2007144151 A1 | 12/2007 |
| WO | 2007103294 A3 | 4/2008 |
| WO | 2008049516 A3 | 5/2008 |
| WO | 2008049516 A3 | 6/2008 |
| WO | 2008152444 A2 | 12/2008 |
| WO | 2009002542 A1 | 12/2008 |
| WO | 2009036311 A1 | 3/2009 |
| WO | 2009040818 | 4/2009 |
| WO | 2008152444 A3 | 6/2009 |
| WO | 2009069006 A2 | 6/2009 |
| WO | 2009098072 A2 | 8/2009 |
| WO | 2009098072 A3 | 10/2009 |
| WO | 2009133352 A2 | 11/2009 |
| WO | 2009069006 A3 | 12/2009 |
| WO | 2010033188 A2 | 3/2010 |
| WO | 2009133352 A3 | 10/2010 |
| WO | WO-2010146872 A1 | 12/2010 |
| WO | 2011000210 A1 | 1/2011 |
| WO | 2011073995 A2 | 6/2011 |
| WO | 2011073995 A3 | 8/2011 |
| WO | 2011120084 A1 | 10/2011 |
| WO | 2011128336 A1 | 10/2011 |
| WO | 2010033188 A3 | 11/2011 |
| WO | 2012009778 A2 | 1/2012 |
| WO | 2012024361 A1 | 2/2012 |
| WO | WO-2012055814 A1 | 5/2012 |
| WO | WO-2012055840 A1 | 5/2012 |
| WO | WO-2012065740 A1 | 5/2012 |
| WO | WO-2012098090 A1 | 7/2012 |
| WO | WO-2012116277 A1 | 8/2012 |
| WO | WO-2012118563 A2 | 9/2012 |
| WO | WO-2012120365 A1 | 9/2012 |
| WO | WO-2012127501 A2 | 9/2012 |
| WO | WO-2012156561 A1 | 11/2012 |
| WO | WO-2012156822 A1 | 11/2012 |
| WO | WO-2012158483 A2 | 11/2012 |
| WO | WO-2012166909 A1 | 12/2012 |
| WO | WO-2012170578 A1 | 12/2012 |
| WO | WO-2013011501 A1 | 1/2013 |
| WO | 2012009778 A3 | 2/2013 |
| WO | WO-2013025449 A1 | 2/2013 |
| WO | WO-2013028639 A1 | 2/2013 |
| WO | WO-2013035101 A1 | 3/2013 |
| WO | WO-2013044067 A1 | 3/2013 |
| WO | WO-2013045404 A2 | 4/2013 |
| WO | WO-2013059285 A1 | 4/2013 |
| WO | WO 2013/078422 A2 | 5/2013 |
| WO | WO-2013063279 A1 | 5/2013 |
| WO | WO-2013064620 A1 | 5/2013 |
| WO | WO-2013071281 A1 | 5/2013 |
| WO | WO-2013088254 A1 | 6/2013 |
| WO | WO-2013102665 A1 | 7/2013 |
| WO | WO-2013106437 A1 | 7/2013 |
| WO | WO-2013113690 A1 | 8/2013 |
| WO | WO-2013124415 A1 | 8/2013 |
| WO | WO-2013127727 A1 | 9/2013 |
| WO | WO-2013127728 A1 | 9/2013 |
| WO | WO-2013144356 A1 | 10/2013 |
| WO | WO-2013149258 A2 | 10/2013 |
| WO | WO-2013158454 A2 | 10/2013 |
| WO | WO-2013170052 A1 | 11/2013 |
| WO | 2013192248 A1 | 12/2013 |
| WO | 2013192249 A1 | 12/2013 |
| WO | 2013192250 A1 | 12/2013 |
| WO | 2013192251 A1 | 12/2013 |
| WO | WO-2013178587 A1 | 12/2013 |
| WO | WO-2013181449 A1 | 12/2013 |
| WO | WO-2014001904 A1 | 1/2014 |
| WO | WO-2014004424 A1 | 1/2014 |
| WO | WO-2014009434 A1 | 1/2014 |
| WO | WO-2014018569 A1 | 1/2014 |
| WO | WO-2014018570 A1 | 1/2014 |
| WO | WO-2014018571 A2 | 1/2014 |
| WO | WO-2014018856 A1 | 1/2014 |
| WO | WO-2014018932 A2 | 1/2014 |
| WO | WO-2014031958 A1 | 2/2014 |
| WO | WO-2014041120 A1 | 3/2014 |
| WO | WO-2014052792 A1 | 4/2014 |
| WO | WO-2014056897 A1 | 4/2014 |
| WO | WO-2014066442 A2 | 5/2014 |
| WO | WO-2014074846 A1 | 5/2014 |
| WO | WO-2014076231 A1 | 5/2014 |
| WO | WO-2014076569 A2 | 5/2014 |
| WO | WO-2014081598 A1 | 5/2014 |
| WO | WO-2014086739 A1 | 6/2014 |
| WO | WO-2014093114 A1 | 6/2014 |
| WO | WO-2014104784 A1 | 7/2014 |

OTHER PUBLICATIONS

Application Note JASCO CD Spectra of Pharmaceuticals Substances Steroids, 2 pages.
Archer, D.F., et al., "Effects of Ospemifene on the Female Reproductive and Urinary Tracts : Translation From Preclinical Models into Clinical Evidence," Menopause, Lippincott-Raven Publishers, United States (2014).
Archer, F., et al., "Estrace® vs Premarin® for Treatment of Menopausal Symptoms: Dosage Comparison Study 9(1):21-31, (1992).
Ashburn, A.D., et al., "Cardiovascular , Hepatic and Renal Lesions in Mice Receiving Cortisone , Estrone and Progesterone," The Yale Journal of Biology and Medicine 35:329-340, Yale Journal of Biology and Medicine, United States (1963).
Bartosova, L. and Bajgar, J., "Transdermal Drug Delivery in Vitro Using Diffusion Cells," Current Medicinal Chemistry 19(27):4671-4677, Bentham Science Publishers, Netherlands (2012).
Benbow, A.L. and Waddell, B.J., "Distribution and Metabolism of Maternal Progesterone in the Uterus, Placenta, and Fetus During Rat Pregnancy," Biology of Reproduction 52(6):1327-1333, Society for the Study of Reproduction, United States (1995).
Blake, E.J., et al., "Single and Multidose Pharmacokinetic Study of a Vaginal Micronized Progesterone insert (Endometrin ) Compared with Vaginal Gel in Healthy Reproductive-Aged Female Subjects," Fertility and Sterility 94(4):1296-1301, Elsevier for the American Society for Reproductive Medicine, United States (2010).
Brared Christensson, J., et al., "Positive Patch Test Reactions to Oxidized Limonene: Exposure and Relevance," Contact Dermatitis 71(5):264-272, Wiley, England (2014).
Christen, R.D., et al., "Phase I/Pharmacokinetic Study of High-Dose Progesterone and Doxorubicin," Journal of Clinical Oncology :

(56) References Cited

OTHER PUBLICATIONS

Official Journal of the American Society of Clinical Oncology 11(12):2417-2426, American Society of Clinical Oncology, United States (1993).
Christensson, J.B., et al., "Limonene Hydroperoxide Analogues Differ in Allergenic Activity," Contact Dermatitis 59(6):344-352, Wiley, England (2008).
Christensson, J.B., et al., "Limonene Hydroperoxide Analogues Show Specific Patch Test Reactions," Contact Dermatitis 70(5):291-299, Wiley, England (2014).
Cicinelli, E., et al., "Direct Transport of Progesterone From Vagina to Uterus," Obstetrics and Gynecology 95(3):403-406, Lippincott Williams & Wilkins, United States (2000).
Corbett, S.H., et al., "Trends in Pharmacy Compounding for Women's Health in North Carolina : Focus on Vulvodynia," Southern Medical Journal 107(7):433-436, Southern Medical Association, United States (2014).
Critchley, H.O., et al., "Estrogen Receptor Beta, but Not Estrogen Receptor Alpha, Is Present in the Vascular Endothelium of the Human and Nonhuman Primate Endometrium," The Journal of Clinical Endocrinology and Metabolism 86(3):1370-1378, Endocrine Society, United States (2001).
Diramio, J.A., et al., "Poly(Ethylene Glycol) Methacrylate/Dimethacrylate Hydrogels for Controlled Release of Hydrophobic Drugs," Masters of Science Thesis, University of Georgia, Athens, Georgia, 131 pages (2002).
Engelhardt, H., et al., "Conceptus influences the Distribution of Uterine Leukocytes During Early Porcine Pregnancy," Biology of Reproduction 66(6):1875-1880, Society for the Study of Reproduction, United States (2002).
Ettinger, B., et al., "Comparison of Endometrial Growth Produced by Unopposed Conjugated Estrogens or by Micronized Estradiol in Postmenopausal Women," American Journal of Obstetrics and Gynecology 176(1 Pt1):112-117, Elsevier, United States (1997).
Excipients for Pharmaceuticals, Sasol Olefins & Surfactants GMBH, 28 pages (2010).
Filipsson,F., et al., "Concise International Chemical Assessment Document 5," Limonene, first draft, World Health Organization, Geneva, 36 pages (1998).
Final Office Action dated Oct. 26, 2012for U.S. Appl. No. 12/561,515, filed Sep. 17, 2009.
Flyvholm, M.A. and Menne, T., "Sensitizing Risk of butylated Hydroxytoluene Based on Exposure and Effect Data," Contact Dermatitis 23(5):341-345, Wiley, England (1990).
Franklin, R.D. and Kutteh, W.H., "Characterization of Immunoglobulins and Cytokines in Human Cervical Mucus : influence of Exogenous and Endogenous Hormones," Journal of Reproductive Immunology 42(2):93-106, Elsevier/North-Holland Biomedical Press, Ireland (1999).
Franz, T.J., et al., "Use of Excised Human Skin to Assess the Bioequivalence of Topical Products," Skin Pharmacology and Physiology 22(5):276-286, Karger, Switzerland (2009).
Fuchs, K.O., et al., "The Effects of an Estrogen and Glycolic Acid Cream on the Facial Skin of Postmenopausal Women: A Randomized Histologic Study," Cutis 71(6):481-488, Frontline Medical Communications, United States (2003).
Furness, S., et al., "Hormone therapy in Postmenopausal Women and Risk of Endometrial Hyperplasia," The Cochrane Database of Systematic Reviews 8:1-204, Wiley, England (2012).
Gafvert, E., et al., "Free Radicals in Antigen formation: Reduction of Contact Allergic Response to Hydroperoxides by Epidermal Treatment with Antioxidants," The British Journal of Dermatology 146(4):649-656, Blackwell Scientific Publications, England (2002).
Gattefossé SAS, Regulatory Data Sheet, Gelot 64, 6 pages (2012).
Gattefossé SAS, Regulatory Data Sheet, Lauroglycol 90, 5 pages (2012).
Gattefosse, "Excipients for Safe and Effective Topical Delivery," http://drug-dev.com/Main/Back-Issues/Transdermal-Topical-Subcutaneous-NonInvasive-Deliv-5.aspx# (2012).

Gattefosse SAS, Material Safety Data Sheet, Gelot 64, 8 pages 2012.
Gillet, J.Y., et al., "induction of Amenorrhea During Hormone Replacement therapy : Optimal Micronized Progesterone Dose a Multicenter Study," Maturitas 19(2):103-115, Elsevier/North Holland Biomedical Press, Ireland (1994).
Glaser, R.L., et al., "Pilot Study : Absorption and Efficacy of Multiple Hormones Delivered in a Single Cream Applied to the Mucous Membranes of the Labia and Vagina," Gynecologic and Obstetric Investigation 66(2):111-118,Basel, New York, Karger., Switzerland (2008).
Golatowski, C., et al., "Comparative Evaluation of Saliva Collection Methods for Proteome Analysis," International Journal of Clinical Chemistry 419:42-46,Elsevier., Netherlands (2013).
Graham, J.D. and Clarke, C.L., "Physiological Action of Progesterone in Target Tissues," Endocrine Reviews 18(4):502-519, Endocrine Society, United States (1997).
Groothuis, P.G., et al., "Estrogen and the Endometrium : Lessons Learned From Gene Expression Profiling in Rodents and Human," Human Reproduction Update 13(4):405-417, Published for the European Society of Human Reproduction and Embryology by Oxford University Press, England (2007).
Hamid, K.A., et al., "The Effects of Common Solubilizing Agents on the intestinal Membrane Barrier Functions and Membrane Toxicity in Rats," International Journal of Pharmaceutics 379(1):100-108,Amsterdam, Elsevier/North-Holland Biomedical Press., Netherlands (2009).
Hatton, J., et al., "Safety and Efficacy of a Lipid Emulsion Containing Medium-Chain Triglycerides," Clinical Pharmacy 9(5):366-371, American Society of Hospital Pharmacists, United States (1990).
He, F., et al., "Apoptotic Signaling Pathways in Uteri of Rats with Endometrial Hyperplasia induced by Ovariectomy Combined with Estrogen," Gynecologic and Obstetric Investigation 76(1):51-56,Karger., Switzerland (2013).
Helmy, A., et al, "Estrogenic Effect of Soy Phytoestrogens on the Uterus of Ovariectomized Female Rats," Clinical Pharmacology & Biopharmaceutics, S2, 7 pages (2014).
Hostynek, J., et al., "Predictinga bsorptiono f fragrancec hemicalst hrough human skin," Journal of the Society of Cosmetic Chemists 46:221-229, (1995).
Hurn, P.D. and Macrae, I.M., "Estrogen as a Neuroprotectant in Stroke," Journal of Cerebral Blood Flow and Metabolism : Official Journal of the International Society of Cerebral Blood Flow and Metabolism 20(4):631-652, Nature Publishing Group, United States (2000).
Hyder, S.M., et al., "Synthetic Estrogen 17Alpha-Ethinyl Estradiol induces Pattern of Uterine Gene Expression Similar to Endogenous Estrogen 17Beta-Estradiol," The Journal of Pharmacology and Experimental Therapeutics 290(2):740-747, American Society for Pharmacology and Experimental Therapeutics, United States (1999).
Josh, S.G., et al., "Detection and Synthesis of a Progestagen-Dependent Protein in Human Endometrium," Journal of Reproduction and Fertility 59(2):273-285, Portland Press, England (1980).
Kanno J., et al., "The Oecd Program to Validate the Rat Uterotrophic Bioassay to Screen Compounds for in Vivo Estrogenic Responses : Phase 1," Environmental Health Perspectives 109(8):785-794,N. C. National Institute of Environmental Health Sciences., United States (2001).
Karlberg, A.T., et al., "Air Oxidation of D-Limonene (the Citrus Solvent) Creates Potent Allergens," Contact Dermatitis 26(5):332-340, Wiley, England (1992).
Karlberg, A.T., et al., "Influence of an Anti-Oxidant on the formation of Allergenic Compounds During Auto-Oxidation of D-Limonene," The Annals of Occupational Hygiene 38(2):199-207, Oxford University Press, England (1994).
Kaunitz, A.M. "Extended Duration Use of Menopausal Hormone therapy," Menopause 21(6):679-681, Lippincott-Raven Publishers, United States (2014).
Kharode, Y., et al., "The Pairing of a Selective Estrogen Receptor Modulator, Bazedoxifene, with Conjugated Estrogens as a New

(56) References Cited

OTHER PUBLICATIONS

Paradigm for the Treatment of Menopausal Symptoms and Osteoporosis Prevention," Endocrinology 149(12):6084-6091, Endocrine Society, United States (2008).
Kim, Y.W., et al., "Safety Evaluation and Risk Assessment of D-Limonene," Journal of Toxicology and Environmental Health. Part B, Critical Reviews 16(1):17-38, Informa Healthcare, England (2013).
Kola, K., et al., "Enhancing Mechanism of Labrasol on intestinal Membrane Permeability of the Hydrophilic Drug Gentamicin Sulfate," European Journal of Pharmaceutics and Biopharmaceutics : Official Journal of Arbeitsgemeinschaft Fur Pharmazeutische Verfahrenstechnik E.V 64(1):82-91, Elsevier Science, Netherlands (2006).
Komm, B.S., et al., "Bazedoxifene Acetate : A Selective Estrogen Receptor Modulator with Improved Selectivity," Endocrinology 146(9):3999-4008, Endocrine Society, United States (2005).
Kumasaka, T., et al., "Effects of Various forms of Progestin on the Endometrium of the Estrogen-Primed , Ovariectomized Rat," Endocrine Journal 41(2):161-169, Japan Endocrine Society, Japan (1994).
Kuon, R.J. and Garfield, R.E., "Actions of Progestins for the inhibition of Cervical Ripening and Uterine Contractions to Prevent Preterm Birth," Facts, Views &Amp; Vision in Obgyn 4(2):110-119,Flemish Society of Obstetrics & Gynaecology, Belgium (2012).
Kuon, R.J., et al., "A Novel Optical Method to Assess Cervical Changes During Pregnancy and Use to Evaluate the Effects of Progestins on Term and Preterm Labor," American Journal of Obstetrics and Gynecology 205(1):82.e15-82.e20, Elsevier, United States (2011).
Kuon, R.J., et al., "Pharmacologic Actions of Progestins to inhibit Cervical Ripening and Prevent Delivery Depend on their Properties , the Route of Administration , and the Vehicle," American Journal of Obstetrics and Gynecology 202(5):455.e1-455.e9, Elsevier, United States (2010).
Lanigan, R.S. and Yamarik, T.A., "Final Report on the Safety Assessment of Bht (1)," International Journal of Toxicology 21(2):19-94, Sage Publications, United States (2002).
Lapez-Belmonte, J., et al., "Comparative Uterine Effects on Ovariectomized Rats After Repeated Treatment with Different Vaginal Estrogen formulations," Maturitas 72(4):353-358, Elsevier/North Holland Biomedical Press, Ireland (2012).
Lauer, A.C., et al., "Evaluation of the Hairless Rat as a Model for in Vivo Percutaneous Absorption," Journal of Pharmaceutical Sciences 86(1):13-18, Wiley-Liss, United States (1997).
Leonetti, H.B., et al., "Transdermal Progesterone Cream as an Alternative Progestin in Hormone therapy," Alternative Therapies in Health and Medicine 11(6):36-38, InnoVision Communications, United States (2005).
Madishetti, S.K., et al., "Development of Domperidone Bilayered Matrix Type Transdermal Patches : Physicochemical , in Vitro and Ex Vivo Characterization," Journal of Faculty of Pharmacy 18(3):221-229, BioMed Central, England (2010).
Miles, R.A., et al., "Pharmacokinetics and Endometrial Tissue Levels of Progesterone After Administration by intramuscular and Vaginal Routes : A Comparative Study," Fertility and Sterility 62(3):485-490, Elsevier for the American Society for Reproductive Medicine, United States (1994).
Miller, J.A., et al., "Safety and Feasibility of Topical Application of Limonene as a Massage Oil to the Breast," Journal of Cancer Therapy 3(5A), Scientific Research Publishing, United States (2012).
Nilsson, U., et al., "Analysis of Contact Allergenic Compounds in Oxidized d-Limonene," Chromatographia 42:199-205, (1996).
Non Final Office Action dated Dec. 12, 2011 for U.S. Appl. No. 12/561,515, filed Sep. 17, 2009.
Notice of Allowance dated Sep. 11, 2013 for U.S. Appl. No. 12/561,515, filed Sep. 17, 2009.

Opinion on Diethylene glycol monoethyl ether, Scientific Committee on Consumer Products, The SCCP adopted this opinion at its 10th plenary,27 pages (2006).
Outterson, K. "The Drug Quality and Security Act—Mind the Gaps," The New England Journal of Medicine 370(2):97-99,Massachusetts Medical Society., United States (2014).
Palamakula, A., et al., "Preparation and In Vitro Characterization of Self-Nanoemulsified Drug Delivery Systems of Coenzyme Q10 Using Chiral Essential Oil Components" Pharmaceutical Technology 74-88, (2004).
Panay, N., et al., "The 2013 British Menopause Society & Women's Health Concern recommendations on hormone replacement therapy," Menopause International: The Integrated Journal of Postreproductive Health, published online May 23, 2013, Sage Publications. http://min.sagepub.com/content/early/2013/05/23/1754045313489645.1.
Parasuraman, S., et al., "Blood Sample Collection in Small Laboratory Animals," Journal of Pharmacology Pharmacotherapeutics 1(2):87-93, Medknow Publications and Media, India (2010).
Pfaus, J.G., et al., "Selective Facilitation of Sexual Solicitation in the Female Rat by a Melanocortin Receptor Agonist," Proceedings of The National Academy of Sciences of The United States of America 101(27):10201-10204, National Academy of Sciences, United States (2004).
Pickles, V.R. "Cutaneous Reactions to injection of Progesterone Solutions into the Skin," British Medical Journal 2(4780):373-374, British Medical Association, England (1952).
Pinkerton, J.V. "What are the Concerns About Custom-Compounded "Bioidentical" Hormone therapy?," Menopause 21(12):1298-1300, Lippincott-Raven Publishers, United States (2014).
Prausnitz, M.R. and Langer, R., "Transdermal Drug Delivery," Nature Biotechnology 26(11):1261-1268, Nature America Publishing, United States (2008).
Product Safety Assessment, Diethylene Glycol Monoethyl Ether, The Dow Chemical Company Page, 5 Pages (2007).
Provider Data Sheet, "About Dried Blood Spot Testing," ZRT Laboratory, 3 pages (2014).
Rahn, D.D., et al., "Vaginal Estrogen for Genitourinary Syndrome of Menopause: A Systematic Review," Obstetrics and Gynecology 124(6):1147-1156, Lippincott Williams & Wilkins, United States (2014).
Reisman, S.A., et al., "Topical Application of the Synthetic Triterpenoid Rta 408 Protects Mice From Radiation-induced Dermatitis," Radiation Research 181(5):512-520, Radiation Research Society, United States (2014).
Ross, D., et al., "Randomized , Double-Blind , Dose-Ranging Study of the Endometrial Effects of a Vaginal Progesterone Gel in Estrogen-Treated Postmenopausal Women," American Journal of Obstetrics and Gynecology 177(4):937-941, Elsevier, United States (1997).
Ruan, X. and Mueck, A.O., "Systemic Progesterone therapy—Oral, Vaginal , injections and Even Transdermal ?," Maturitas 79(3):248-255, Elsevier/North Holland Biomedical Press, Ireland (2014).
Salem, H.F. "Sustained-Release Progesterone Nanosuspension Following intramuscular injection in Ovariectomized Rats," International Journal of Nanomedicine 10:943-954,DOVE Medical Press, New Zealand (2010).
Santen, R.J. "Vaginal Administration of Estradiol : Effects of Dose , Preparation and Timing on Plasma Estradiol Levels," The Journal of The International Menopause Society :1-14, Informa Healthcare, England (2014).
Schutte, S.C. and Taylor, R.N., "A Tissue-Engineered Human Endometrial Stroma That Responds to Cues for Secretory Differentiation , Decidualization , and Menstruation," Fertility and Sterility 97(4):997-1003, Elsevier for the American Society for Reproductive Medicine, United States (2012).
Schweikart, K.M., et al., "Comparative Uterotrophic Effects of Endoxifen and Tamoxifen in Ovariectomized Sprague-Dawley Rats," Toxicologic Pathology 42(8):1188-1196, Sage Publications, United States (2014).
Shao, R., et al., "Direct Effects of Metformin in the Endometrium: A Hypothetical Mechanism for the Treatment of Women with Pcos

(56) References Cited

OTHER PUBLICATIONS and Endometrial Carcinoma," Journal of Experimental & Clinical Cancer Research 33:41, BioMed Central, England (2014).
Shrier, L.A., et al., "Mucosal Immunity of the Adolescent Female Genital Tract," The Journal of Adolescent Health 32(3):183-186, Elsevier, United States (2003).
Siew, A, et al.,"Bioavailability Enhancement with Lipid-Based Durg-Delivery Systems" Phamraceutical Technology 28,30-31, (2014).
Simon, J.A. "What If the Women's Health initiative Had Used Transdermal Estradiol and Oral Progesterone instead?," Menopause 21(7):769-783, Lippincott-Raven Publishers, United States (2014).
Smyth, H.F., et al., "A 2-Yr Study of Diethylene Glycol Monoethyl Ether in Rats," Food and Cosmetics Toxicology 2:641-642, Pergamon Press, England (1964).
Stanczyk, F.Z., et al., "Therapeutically Equivalent Pharmacokinetic Profile Across Three Application Sites for Ag200-15 , A Novel Low-Estrogen Dose Contraceptive Patch," Contraception 87(6):744-749, Elsevier, United States (2013).
Sullivan, D.W.Jr., et al., "A review of the nonclinical safety of Transcutol®, a highly purified form of diethylene glycol monoethyl ether (DEGEE) used as a pharmaceutical excipient," Food and Chemical Toxicology 72:40-50, Elsevier Science Ltd, England (2014).
Sun, J. "D-Limonene : Safety and Clinical Applications," Alternative Medicine Review 12(3):259-264, Alternative Medicine Review, United States (2007).
Tang, F.Y., et al., "Effect of Estrogen and Progesterone on the Development of Endometrial Hyperplasia in the Fischer Rat," Biology of Reproduction 31(2):399-413, Society for the Study of Reproduction, United States (1984).
Tas, M., et al., "Comparison of Antiproliferative Effects of Metformine and Progesterone on Estrogen-induced Endometrial Hyperplasia in Rats," Gynecological Endocrinology 29(4):311-314, Informa Healthcare, England (2013).
Thomas, P. "Characteristics of Membrane Progestin Receptor Alpha (Mpralpha) and Progesterone Membrane Receptor Component 1 (Pgmrc1) and their Roles in Mediating Rapid Progestin Actions," Frontiers in Neuroendocrinology 29(2):292-312, Academic Press, United States (2008).
Tuleu, C., et al., "Comparative Bioavailability Study in Dogs of a Self-Emulsifying formulation of Progesterone Presented in a Pellet and Liquid form Compared with an Aqueous Suspension of Progesterone," Journal of Pharmaceutical Sciences 93(6):1495-1502, Wiley-Liss, United States (2004).
Ueda, T., et al., "Topical and Transdermal Drug Products," Pharmacopeial Forum 35(3):750-764, (2009).
Voegtline, K.M. and Granger, D.A., "Dispatches From the interface of Salivary Bioscience and Neonatal Research," Frontiers in Endocrinology 5:25,Frontiers Research Foundation, Switzerland (2014).
Waddell, B.J. and Bruce, N.W., "The Metabolic Clearance of Progesterone in the Pregnant Rat : Absence of a Physiological Role for the Lung," Biology of Reproduction 40(6):1188-1193, Society for the Study of Reproduction, United States (1989).
Walter, L.M., et al., "The Role of Progesterone in Endometrial Angiogenesis in Pregnant and Ovariectomised Mice," Reproduction 129(6):765-777,Reproduction and Fertility by BioScientifica, England (2005).
Wren, B.G., et al., "Effect of Sequential Transdermal Progesterone Cream on Endometrium , Bleeding Pattern , and Plasma Progesterone and Salivary Progesterone Levels in Postmenopausal Women," The Journal of the International Menopause Society 3(3):155-160, Informa Healthcare, England (2000).
Wu, X., et al., "Gene Expression Profiling of the Effects of Castration and Estrogen Treatment in the Rat Uterus," Biology of Reproduction 69(4):1308-1317, Society for the Study of Reproduction, United States (2003).
Zava, D. "Topical Progesterone Delivery and Levels in Serum, Saliva, Capillary Blood, and Tissues" Script:4-5.
Zava, D.T., et al., "Percutaneous absorption of progesterone," Maturitas 77:91-92, Elsevier/North Holland Biomedical Press, Ireland (2014).
Geelen, M.J.H., et al., "Dietary Medium-Chain Fatty Acids Raise and (n-3) Polyunsaturated Fatty Acids Lower Hepatic Triacylglycerol Synthesis in Rats," The Journal of Nutrition 125:2449-2456, American Institute of Nutrition, United States (1995).
Herman, A and Herman, A.P., "Essential oils and their constituents as skin penetration enhancer for transdermal drug delivery: a review," Journal of Pharmacy and Pharmacology 67(4):473-485, Royal Pharmaceutical Society, England (2014).
Manson, J.E., et al., "Menopausal Hormone Therapy and Health Outcomes During the Intervention and Extended Poststopping Phases of the Women's Health Initiative Randomized Trials," The Journal of the American Medical Association 310:1353-1368, American Medical Association, United States (2013).
Notice of Allowance, dated Dec. 10, 2014, in U.S. Appl. No. 14/099,562, Bernick, B.A., filed Dec. 6, 2013, 10 pages.
Notice of Allowance, dated Dec. 10, 2014, in U.S. Appl. No. 14/099,598, Bernick, B.A., filed Dec. 6, 2013, 8 pages.
Notice of Allowance, dated Dec. 15, 2014, in U.S. Appl. No. 14/099,623, Bernick, B.A., filed Dec. 6, 2013, 9 pages.
Notice of Allowance, dated Feb. 11, 2015, in U.S. Appl. No. 14/475,864, Bernick, B.A., filed Sep. 3, 2014, 9 pages.
Notice of Allowance, dated Feb. 13, 2015, in U.S. Appl. No. 14/475,814, Bernick, B.A., filed Sep. 3, 2014, 6 pages.
Notice of Allowance, dated Jan. 22, 2015, in U.S. Appl. No. 14/099,582, Bernick, B.A., filed Dec. 6, 2013, 5 pages.
Notice of Allowance, dated Jul. 14, 2014, in U.S. Appl. No. 14/099,545, Bernick, B.A., filed Dec. 6, 2013, 9 pages.
Notice of Allowance, dated Jul. 15, 2014, in U.S. Appl. No. 14/099,571, Bernick, B.A., filed Dec. 6, 2013, 11 pages.
Notice of Allowance, dated Nov. 26, 2014, in U.S. Appl. No. 14/099,612, Bernick, B.A., filed Dec. 6, 2013, 12 pages.
Notice of Allowance, dated Nov. 7, 2014, in U.S. Appl. No. 14/099,582, filed Dec. 6, 2013, 14 pages.
Office Action, dated Apr. 14, 2015, in U.S. Appl. No. 14/125,554, Bernick, B.A., filed Dec. 12, 2013, 9 pages.
Office Action, dated Apr. 7, 2015, in U.S. Appl. No. 14/624,051, Bernick B.A., filed Feb. 17, 2015, 10 pages.
Office Action, dated Dec. 8, 2014, in U.S. Appl. No. 14/106,655, Bernick, B.A., filed Dec. 13, 2013, 9 pages.
Office Action, dated Feb. 18, 2015, in U.S. Appl. No. 14/521,230, Bernick, B.A., filed Oct. 22, 2014, 8 pages.
Office Action, dated Jul. 18, 2014, in U.S. Appl. No. 14/099,623, Bernick, B.A., filed Dec. 6, 2013, 12 pages.
Office Action, dated Jul. 2, 2014, in U.S. Appl. No. 14/099,562, Bernick, B.A., filed Dec. 6, 2013, 9 pages.
Office Action, dated Jul. 3, 2014, in U.S. Appl. No. 14/099,598, Bernick, B.A., filed Dec. 6, 2013, 16 pages.
Office Action, dated Jul. 30, 2014, in U.S. Appl. No. 14/099,612, Bernick, B.A., filed Dec. 6, 2013, 12 pages.
Office Action, dated Jun. 17, 2014, in U.S. Appl. No. 14/099,582, Bernick, B.A., filed Dec. 6, 2013, 14 pages.
Office Action, dated Mar. 12, 2015, in U.S. Appl. No. 14/136,048, Bernick, B.A., filed Dec. 20, 2013, 24 pages.
Office Action, dated Mar. 27, 2014, in U.S. Appl. No. 14/099,562, Bernick, B.A., filed Dec. 6, 2013, 8 pages.
Office Action, dated Oct. 2, 2014, in U.S. Appl. No. 14/475,864, Bernick, B.A., filed Sep. 3, 2014, 6 pages.
Office Action, dated Oct. 1, 2014, in U.S. Appl. No. 14/475,814, Bernick, B.A., filed Sep. 3, 2014, 6 pages.
Portman, D., et al., "One-year treatment persistence with local estrogen therapy in postmenopausal women diagnosed as having vaginal atrophy," Menopause 22(11): 7 pages, The North American Menopause Society, United States (2015).
Rao, R. and Rao, S., "Intra Subject Variability of Progesterone 200 mg Soft Capsules in Indian Healthy Adult Postmenopausal Female Subjects under Fasting Conditions," Journal of Bioequivalence & Bioavailability 6(4):139-143, Open Access (2014).
Restriction Requirement, dated Mar. 28, 2014, in U.S. Appl. No. 14/099,571, Bernick, B.A., filed Dec. 6, 2013, 7 pages.

(56) References Cited

OTHER PUBLICATIONS

Restriction Requirement, dated Apr. 14, 2015, in U.S. Appl. No. 13/843,428, Bernick, B.A., filed Mar. 15, 2013, 7 pages.
Restriction Requirement, dated Apr. 29, 2014, in U.S. Appl. No. 14/099,582, Bernick, B.A., filed Dec. 6, 2013, 9 pages.
Restriction Requirement, dated Dec. 5, 2014, in U.S. Appl. No. 14/125,554, Bernick, B.A., filed Dec. 12, 2013, 7 pages.
Restriction Requirement, mailed Dec. 5, 2014, in U.S. Appl. No. 14/521,230, Bernick, B.A., filed Oct. 22, 2014, 9 pages.
Restriction Requirement, dated Jul. 3, 2014, in U.S. Appl. No. 14/106,655, Bernick, B.A., filed Dec. 13, 2013, 6 pages.
Restriction Requirement, dated Mar. 16, 2015, in U.S. Appl. No. 13/843,362, Bernick, B.A., filed Mar. 15, 2013, 7 pages.
Restriction Requirement, dated Mar. 20, 2014, in U.S. Appl. No. 14/099,612, Bernick, B.A., filed Dec. 6, 2013, 9 pages.
Restriction Requirement, dated Mar. 26, 2015, in U.S. Appl. No. 14/476,040, Bernick, B.A., filed Sep. 3, 2014, 7 pages.
Restriction Requirement, dated May 13, 2014, in U.S. Appl. No. 14/099,598, Bernick, B.A., filed Dec. 6, 2013, 9 pages.
Restriction Requirement, dated Nov. 4, 2014, in U.S. Appl. No. 14/136,048, Bernick, B.A., filed Dec. 20, 2013, 7 pages.
Schindler, A.E., et al., "Classification and pharmacology of progestins," Maturitas 46S1:S7-S16, Elsevier Ireland Ltd., Ireland (2003).
Sitruk-Ware, R., "Pharmacological profile of progestins," Maturitas 47:277-283, Elsevier Ireland Ltd., Ireland (2004).
Stanczyk, F.Z., "All progestins are not created equal," Science 68:879-890, Elsevier Inc., United States (2003).
Stanczyk, F.Z., et al., "Percutaneous administration of progesterone: blood levels and endometrial protection," Menopause 12(2):232-237, The North American Menopause Society, United States (2005).
Stanczyk, F.Z., "Treatment of postmenopausal women with topical progesterone creams and gels: are they effective," Climacteric 17(Suppl 2):8-11, International Menopause Society, United Kingdom (2014).
Stephenson, K., "Transdermal Progesterone: Effects on Menopausal Symptoms and on Thrombotic, Anticoagulant, and Inflammatory Factors in Postmenopausal Women," International Journal of Pharmaceutical Compounding 12(4):295-304, IJPC, United States (2008).
Weintraub, A., "Women Fooled by Untested Hormones From Compounding Pharmacies," Forbes, accessed at http://onforb.es/1LIUm1V, accessed on Feb. 23, 2015, 3 pages.
Co-pending U.S. Appl. No. 14/671,655, Inventors Amadio, J., et al., filed Mar. 27, 2015 (Not Yet Published).
Co-pending U.S. Appl. No. 14/671,651, Inventors Cacase, J., et al., filed Mar. 27, 2015 (Not Yet Published).
Acarturk, Fusun, Mucoadhesive Vaginal Drug Delivery Systems, Recent Patents on Drug Delivery & Formulation, vol. 3, pp. 193-205, 2009, Bentham Science Publishers, Ltd.
Bhavnani, Bhagu R., et al., Misconception and Concerns about Bioidentical Hormones Used for Custom-Compounded Hormone Therapy, J Clin Endocrin Metab., vol. 97(3), Mar. 2012, The Endocrine Society 2011.
Bhavnani, Bhagu R., et al., Structure Activity Relationships and Differential Interactions and Functional Activity of Various Equine Estrogens Mediated via Estrogen Receptors (ER) and ERa and ERB, Endocrinology, Oct. 2008, vol. 149(10), pp. 4857-4870, The Endocrine Society 2008.
Du, Joanna Y., et al., Percutaneous progesterone delivery via cream or gel application in postmenopausal women: a randomized crossover study of progesterone levels in serum, whole blood, saliva, and capillary blood, Menopause: The Journal of The North American Menopause Society, vol. 20(11), pp. 000-000, The North American Menopause Society 2013.
Fotherby, K., Bioavailability of Orally Administered Sex Steroids Used in Oral Contraception and Hormone Replacement Therapy, Contraception, vol. 54, pp. 59-69, Elsevier Science, Inc. 1996.

Fuchs, Katie O., et al., The Effects of an Estrogen and Glycolic Acid Cream on the Facial Skin of Postmenopausal Women: A Randomized Histologic Study, Pharmacology/Cosmetology, vol. 5(1), 2006.
Hargrove, Joel T., et al., Menopausal Hormone Replacement Therapy With Continuous Daily Oral Micronized Estradiol and Progesterone, Estrogen Replacement Therapy, Obstetrics & Gynecology, vol. 73(4), pp. 606-612, Apr. 1989, The American College of Obstetricians and Gynecologists.
ISR and written opinion for PCT/US/13/46442, dated Nov. 1, 2013.
ISR and written opinion for PCT/US/13/46443, dated Oct. 31, 2013.
ISR and written opinion for PCT/US/13/46444, dated Oct. 31, 2013.
ISR and written opinion for PCT/US/13/46445, dated Nov. 1, 2013.
Kincl, Fred A., et al., Short Communication, Increasing Oral Bioavailability of Progesterone by Formulation, Journal of Steroid Biochemistry, vol. 9, pp. 83-84 Pergamon Press 1978, Great Britain.
The Journal of the North American Menopause Society (NAMS), Management of symptomatic vulvovaginal atrophy: 2013 position statement of The North American Menopause Society, Menopause, vol. 20(9), pp. 888-902, The North American Menopause Society 2013.
Panay, Nick, The 2013 British Menopause Society & women's Health Concern recommendations on hormone replacement therapy, Menopause International, The Integrated Journal of Postreproductive Health, vol. 0(0), Sage 2013.
Patel, Dipen, et al., Transdermal Drug Delivery System: A Review, The Pharma Innovation, The Pharma Journal, vol. 1(4), 2012.
Sarrel, Philip M., et al., The Mortality Toll of Estrogen Avoidance: An Analysis of Excess Deaths Among Hysterectomized Women Aged 50 to 59 Years, American Journal of Public Health, Research and Practice, pp. e1-e6, Published online ahead of print Jul. 18, 2013.
Shufelt, Chrisandra L., et al., Hormone therapy dose, formulation, route of delivery, and risk of cardiovascular events in women: findings from the Women's Health Initiative Observational Study, Menopause: The Journal of The North American Menopause Society (NAMS), vol. 21(3), pp. 000-000, The North American Menopause Society 2013.
Simon, James, et al., Effective Treatment of Vaginal Atrophy With an Ultra-Low-Dose Estradiol Vaginal Tablet, Obstetrics & Gynecology, vol. 112(5), pp. 1053-1060, pp. 373-402, Nov. 2008.
Sitruk-Ware, Regine, et al., Oral Micronized Progesterone, Contraception, vol. 36(4), Oct. 1987.
Sitruk-Ware, Regine, Progesterones in hormonal replacement therapy: new molecules, risks, and benefits, Menopause: The Journal of the North American Menopause Society (NAMS), vol. 9(1), pp. 6-15, The North American Menopause Society 2002.
Smith, Nicholas L., et al., Lower Risk of Cardiovascular Events in Postmenopausal Women Taking Oral Estradiol Compared with Oral Conjugated Equine Estrogens, JAMA Intern Med, pp. e1-e7, published online Sep. 30, 2013.
Stanczyk, Frank, et al., Ethinyl estradiol and 17B-estradiol in combined oral contraceptives: pharmacokinetics, pharmacodynamics and risk assessment, Contraception, vol. 87, pp. 706-727, Elsevier 2013.
USPTO, Final Office Action dated Jul. 16, 2013 for U.S. Appl. No. 13/684,002.
USPTO, Non-Final Office Action dated Mar. 20, 2013 for U.S. Appl. No. 13/684,002.
USPTO, Notice of allowance dated Dec. 6, 2013 for U.S. Appl. No. 13/684,002.
USPTO, Non-Final Office Action dated Feb. 18, 2014 for U.S. Appl. No. 14/099,545.
USPTO, Restriction/Election Requirement dated Feb. 20, 2014 for U.S. Appl. No. 14/099,562.
USPTO, Restriction/Election Requirement dated Mar. 5, 2014 for U.S. Appl. No. 14/099,623.
Whitehead, M. I., et al., Absorption and Metabolism of Oral Progesterone, The British Medical Journal, vol. 280(6217), pp. 825-827, Mar. 22, 1980, BMJ Publishing Group, JSTOR.
Wood, Charles E., et al., Effects of estradiol with micronized progesterone or medroxyprogesterone acetate on risk markers for breast cancer in postmenopausal monkeys, Breast Cancer Res Treat,

(56) References Cited

OTHER PUBLICATIONS vol. 101, pp. 125-134, published online Jul. 14, 2006, Springer Science + Business Media B.V. 2006.
Acog, McKinlay, et al., Practice Bulletin, Clinical Management Guidelines for Obstetrician—Gynecologists, ACOG, No. 141, vol. 123, No. 1, Jan. 2014, Obstetrics & Gynecology.
Araya-Sibaja, Andrea Manela, et al., Chemical Properties of Progesterone Selected Refer., SciFinder, 2014, American Chemical Society & US Natl. Lib. of Med.
Araya-Sibaja, Andrea M.A., Morphology Study of Progesterone Polymorphs Prepared by Polymer-Induced Heteronucleation (PIHn), Scanning vol. 35 pp. 213-221, 2013, Wiley Period., Inc.
Araya-Sibaya, Andrea Manela, et al., Polymorphism in Progesterone, SciFinder, pp. 1-46, Feb. 24, 2014, American Chem. Society & Natl. Lib. of Med.
Araya-Sibaja, Andrea Manela, et al., Polymorphism in Progesterone Selected References, SciFinder, Feb. 24, 2014, pp. 1-12, American Chem. Society & Natl. Lib. of Med.
Bakhmutova-Albert, Ekaterina, et al., Enhancing Aqueous Dissolution Rates of Progesterone via Cocrystallization, SSCI, Division of Aptuit, Poster No. R6247, West Lafayette.
Banerjee, Sila, et al., On the Stability of Salivary Progesterone Under Various Conditions of Storage, Steroids, vol. 46(6), pp. 967-974, Dec. 1985.
Barnett, Steven M, Pressure-tuning infared and solution Raman spectroscopic studies of 17B-estradiol and several A-ring . . . , Vibrational Spectroscopy 8, Elsevier, pp. 263, 1995.
Bernabei, M.T., et al., Release of progesterone polymorphs from dimethylpolysiloxane polymeric matrixes, Bollettino Chimico Farmaceutico, vol. 122(1) pp. 20-26, 1983 SciFinder.
Bhavnani, B.R., Stanczyk, F.Z., Pharmacology of conjugated equine estrogens: Efficacy, safety and mechanism of action, J. Steroid Biochem. Mol. Biol. (2013), Elsevier.
Bhavnani, B.R., Stanczyk, F.Z., Use of medroxyprogesterone acetate for hormone therapy in postmenopausal women: Is it safe? J. Steroid Biochem. Mol. Biol. (2013), Elsevier.
BioMed Central,Solubility of Progesterone in Organic Solvents, Online PDF, http://www.biomedcentral.com/content/supplementary/1475-2859-11-106-S2.pdf.
Borka, Laszlo, Crystal Polymorphism of Pharmaceuticals, Acta Pharm. Jugosl., vol. 40 pp. 71-94, 1990.
Brandstatter-Kuhnert, M, Zur mikroskopischen Identitatsprufung and zur Polymorphie der Sexualhormone, Acta, vol. 6, pp. 847-853, 1959, Univ. Innsbruck.
Brinton, L.A., Felix, A.S., Menopausal hormone therapy and risk of endometrial cancer, J. Steroid Biochem. Mol. Biol. (2013), Elsevier.
Burry, Kenneth A, Percutaneous absorption of progesterone in postmenopausal women treated with transdermal estrogen, Am J Obstet Gynecol, vol. 180(6) part 1, pp. 1504-1511, 1999.
Busetta, Par Bernard, Structure Cristalline et Molecular de l'Oestradiol Hemihydrate, Acta Cryst., B28 pp. 560, 1972, Bis(dimethyl-o-thiolophenylarsine)palladium(II).
Busetta, Par Bernard, Structure Cristalline et Moleculaire du Complexe Oestradiol-Propanol, Acta Cryst., B28 pp. 1349, 1972, J.A. Kanters and J. Kroon.
Campsteyn, Par H, et al., Structure Cristalline et Molcculaire de la Progesterone C21H30O2, Acta Cryst., B28 pp. 3032-3042, 1972.
Cendejas-Santana, G, et al., Growth and characterization of progesterone crystallites, Revista Mexicana de Fisica, 50, Suplemento 1 pp. 1-3, 2004.
Cole, Wayne & Julian, Percy L, Sterols. I. A Study of the 22-Ketosteroids, Cont. of the Research Lab. of the Glidden Co., Soya Prod. Div., vol. 67 pp. 1369-1375, Aug. 1945, Chicago.
Commodari, Fernando, Comparison of 17B-estradiol structures from x-ray diffraction and solution NMR, Magn. Reson. Chem., vol. 43, pp. 444-450, 2005, Wiley InterScience.
Cooper, A, et al., Systemic absorption of progesterone from Progest cream in postmenopausal women, The Lancet, vol. 351, pp. 1255-1256, Research Letters, Apr. 25, 1998.

Dideberg, O, et al., Crystal data on progesterone (C21H30O2), desoxycorticosterone (C21H30O3), corticosterone (C21H30O4) and aldosterone . . . , J. Appl. Cryst. vol. 4 pp. 80, 1971.
Drakulic, Branko J, Role of complexes formation between drugs and penetration enhancers in transdermal . . . , Inter. Journal of Pharmaceutics, Elsevier, vol. 363, pp. 40-49, 2009.
Duax, William L, et al., Conformation of Progesterone Side Chain: Conflict between X-ray Data and Force-Field Calculations, J. Am. Chem. Soc., vol. 103 pp. 6705-6712, Jun. 1981.
Duclos, R, et al., Polymorphism of Progesterone: Influence of the carrier and of the solid dispersion manufacturing . . . , J. Thermal Anal., vol. 37 pp. 1869-1875, 1991, Wiley.
Ebian, A.R., Ebian Article: Polymorphism and solvation of ethinyl estradiol, SciFinder, Pharmaceutica Acta Helvetiae, vol. 54(4), pp. 111-114, 1979, Alexandria, Egypt.
Eisenberger, A., Westhoff, C., Hormone replacement therapy and venous thromboembolism, J. Steroid Biochem. Mol. Biol. (2013), Elsevier.
Faassen, Fried, Physicochemical Properties and Transport of Steroids across Caco-2 Cells, Pharmaceutical Research, vol. 20(2), 2003, Plenum Pub. Corp.
FDA, Draft Guidance on Progesterone, Recommended Apr. 2010, Revised Feb. 2011 http://www.fda.gov/downloads/Drugs/GuidanceComplianceRegulatoryInformation/Guidances/UCM209294.pdf.
Freedman, R.R., Menopausal hot flashes: Mechanisms, endocrinology, treatment, J. Steroid Biochem. Mol. Biol. (2013), Elsevier.
Fugh-Berman, Adriane, Bioidentical Hormones for Menopausal Hormone Therapy: Variation on a Theme, Journal of General Internal Medicine, vol. 22, pp. 1030-1034, 2007.
Giron, D, Thermal analysis and calorimetric methods in the characterisation of polymorphs and solvates, Thermochimica Acta, vol. 248 pp. 1-59, 1995, Elsevier.
Giron-Forest, D, et al., Thermal analyis methods for pharmacopoeial materials, J. Pharmaceutical & Biomedical Anal., vol. 7(12) pp. 1421-1433, 1989, Pergamon Press, Gr. Britain.
Gurney, E.P., et al., The Women's Health Initiative trial and related studies: 10 years later: A clinician's view, J. Steroid Biochem. Mol. Biol. (2013), Elsevier.
Haner, Barbara A., Crystal data (I) for some pregnenes and pregnadienes, Acta Cryst., vol. 17 pp. 1610, 1964.
Hapgood, J.P., et al., Potency of progestogens used in hormonal therapy: Toward understanding differential actions, J. Steroid Biochem. Mol. Biol. (2013), Elsevier.
Helbling, Ignacio M, et al., The Optimization of an Intravaginal Ring Releasing Progesterone Using a Mathematical Model, Pharm Res, vol. 31 pp. 795-808, 2014, Springer Science.
Henderson, V.W., Alzheimer's disease: Review of hormone therapy trials and implications for treatment and prevention after . . . , J. Steroid Biochem. Mol. Biol. (2013), Elsevier.
Henriksen, Thormod, et al., An ENDOR Sturdy of Radiation-Induced Molecular Damage to Progesterone, Jour. of Mag. Resonance, vol. 63, pp. 333-342, 1985, Acedemic Press, Inc.
Hodis, H.N., Mack, W.J., Hormone replacement therapy and the association with heart disease and overall mortality: Clinical . . . , J. Steroid Biochem. Mol. Biol. (2013), Elsevier.
Hospital, Michel, et al., X-ray Crystallography of Estrogens and Their Binding to Receptor Sites, Mol. Pharmacology, vol. 8 pp. 438-445, Acedemic Press, Inc., 1972.
Hulsmann, Stefan, Stability of Extruded 17B-Estradiol Solid Dispersions, Pharmaceutical Development and Tech., vol. 6(2) pp. 223-229, 2001, Marcel Dekker, Inc.
Idder, Salima, et al., Physicochemical properties of Progesterone, SciFinder, pp. 1-26, Feb. 24, 2014, American Chem. Society & US Natl. Lib. of Med.
Johnson, William S, et al., Racemic Progesterone, Tetrahedron Letters No. 4, pp. 193-196, 1963, Pergamon Press Ltd., Great Britain.
Khalil, Sah, Stability and Dissolution Rates of Corticosteroids in Polyethylene Glycol Solid Dispersions, Drug Dev. & Indus. Pharm., vol. 10(5) pp. 771-787, 1984, Marcel Dekker.

(56) References Cited

OTHER PUBLICATIONS

Korkmaz, Filiz, Byophysical Studies of Progesterone-Model Membrane Interactions, Thesis, Grad. School of Nat. and App. Sci. of the Middle East Tech. University, Sep. 2003.
Kotiyan, P.N., Stability indicating HPTLC method for the estimation of estradiol, Journal of Pharmaceutical and Biomedical Analysis, vol. 22 pp. 667-671, 2000, Elsevier.
Krzyminiewski, R, et al., EPR Study of the Stable Radical in a y-Irradiated Single Crystal of Progesterone, Jour. of Mag. Resonance, vol. 46 pp. 300-305, 1982, Acedemic Press.
Stanczyk, F.Z., Bhavnanib, B.R., Current views of hormone therapy for the management and treatment of postmenopausal women, J. Steroid Biochem. Mol. Biol. (2014), Elsevier.
Stein, Emily A, et al., Progesterone Physical Properties, SciFinder, pp. 1-46, Feb. 24, 2014, American Chem. Society & US Natl. Lib. of Med.
Stein, Emily A, et al., Progesterone Physical Properties, SciFinder, pp. 1-46, Mar. 3, 2014, American Chem. Society & US Natl. Lib. of Med.
Stein, Emily A, et al., Progesterone, SciFinder Scholar Search, pp. 1-46, Feb. 24, 2014, American Chem. Society & Natl. Lib. of Med.
Struhar, M, et al., Estradiol Benzoate: Preparation of an injection suspension . . . , SciFinder, Cesko-Slovenska Farmacie, vol. 27(6), pp. 245-249, 1978, Bratislava, Czech.
Tait, Alex D, Characterization of the Prod. from the Oxidation of Progesterone with Osmium Tetroxide, Dept of Investigative Med., Univ. Cambridge, Gt. Britain pp. 531-542, 1972.
Takacs M, et al., The light sensitivity of corticosteroids in crystalline form, Pharmaceutica acta Helvetiae, vol. 66 (5-6) pp. 137-140, 1991, Hardin Library.
Tan, Melvin S, et al., A Sensitive Method for the Determination of Progesterone in Human Plasma by LC-MS-MS, M1025, Cedra Corporation, Austin, Texas.
Tella, S.H., Gallagher, J.C., Prevention and treatment of postmenopausal osteoporosis, J. Steroid Biochem. Mol. Biol. (2013), Elsevier.
Thomas, Joshua, et al., The effect of water solubility of solutes on their flux through human skin in vitro: An . . . , Intl. J. of Pharmaceut., vol. 339 pp. 157-167, 2007, Elsevier.
Tripathi, R, et al., Study of Polymorphs of Progesterone by Novel Melt Sonocrystallization Technique: A Technical Note, AAPS PhamSciTech, vol. 11, No. 3, Sep. 2010.
USP Monographs: Progesterone, USP29, www.pharmacopeia.cn/v29240/usp29nf24s0_m69870.html, search done: Feb. 25, 2014.
Utian, Wulf H, et al., Relief of vasomotor symptoms and vaginal atrophy with lower doses of conjugated equine estrogens . . . Fertility and Sterility, vol. 75(6) pp. 1065, Jun. 2001.
Weber, M.T., et al., Cognition and mood in perimenopause: A systematic review and meta-analysis, J. SteroidBiochem. Mol. Biol. (2013), Elsevier.
Wiranidchapong, Chutima, Method of preparation does not affect the miscibility between steroid hormone and polymethacrylate, Thermochimica Acta 485, Elsevier, pp. 57, 2009.
Yalkowsky, Samuel H, & Valvani, Shri C, Solubility and Partitioning I: Solubility of Nonelectrolytes in Water, J. of Pharmaceutical Sciences, vol. 69(8) pp. 912-922, 1980.
Yalkowsky, Samuel H, Handbook of Acqueous Solubility Data, Solutions, pp. 1110-1111, CRC Press, Boca Raton, London, New York, Wash. D.C.
Yue, W.,Genotoxic metabolites of estradiol in breast: potential mechanism of estradiol induced carcinogenesis, Journal of Steroid Biochem & Mol Biology, vol. 86 pp. 477-486, 2003.
Kubli-Garfias, C, et al., Ab initio calculations of the electronic structure of glucocorticoids, Jour. of Mol. Structure, Theochem, vol. 454 pp. 267-275, 1998, Elsevier.
Kubli-Garfias, Carlos, Ab initio study of the electronic structure of progesterone and related progestins, Jour. of Mol. Structure, Theochem vol. 425, pp. 171-179, 1998, Elsevier.
Kuhnert-Brandstaetter, M & Kofler, A, Zur Unterscheidung von losungsmittelhaltigen pseudopolymorphen Kristallformen und polymorphen Modifikationen bei Steroidhormonen.II. vol. 1 pp. 127-139, 1968, Mikrochimica Acta.
Kuhnert-Brandstaetter, M & Lnder, R, Zur Hydratbildung bei Steroidhormonen, Sci. Pharm., vol. 41(2) pp. 109-116, 1973.
Kuhnert-Brandstatter, M, Thermo-microscopic and spectrophotometric: Determination of steroid hormones, Microchemical Journal 9, pp. 105-133, 1965.
Labrie, et al., Intravaginal prasterone (DHEA) provides local action without clinically significant changes in serum concentrations of estrogens or androgens, Journal of Steroid Biochemistry & Molecular Biology, vol. 138, pp. 359-367, 2013, Elsevier.
Lacey, J.V. Jr., The WHI ten year's later: An epidemiologist's view, J. Steroid Biochem. Mol. Biol. (2013), Elsevier.
Lahiani-Skiba, Malika, Solubility and Dissolution Rate of Progesterone-Cyclodextrin . . . , Drug Development and Industrial Pharmacy, Informa Healthcare vol. 32, pp. 1043-1058, 2006.
Lancaster, Robert W, et al., The Polymorphism of Progesterone: Stabilization of a 'Disappearing' Polymorph by . . . , Jour. of Pharm. Sci., vol. 96(12) pp. 3419-3431, 2007, Wiley-Liss.
Land, Laura M, The influence of water content of triglyceride oils on the solubility of steriods, Pharmaceutical Research, vol. 22(5) May 2005, Springer Science+Business Media.
Leonetti, Helene B, et al., Topical progesterone cream has an antiproliferative effect on estrogen-stimulated endometrium, Fertility and Sterility, vol. 79(1), Jan. 2003.
Lewis, John G., et al., Caution on the use of saliva measurements to monitor absorption of progesterone . . . , Maturitas, The European Menopaus Journal, vol. 41, pp. 1-6, 2002.
Li, Guo-Chian, Solid-state NMR analysis of steroidal conformation of 17a- and 17B-estradiol in the absence and presence of lipi . . . , Steroids, Elsevier, vol. 77, pp. 185-192, 2012.
Lobo, R.A., Foreword, J. Steroid Biochem. Mol. Biol. (2014), Elsevier.
Lvova, M. SH., et al., Thermal Analysis in the Quality Control and Standardization of Some Drugs, J Thermal Anal., vol. 40 pp. 405-411, 1993, Wiley.
Magness, R.R., et al., Estrone, Estradiol-17b and Progesterone Concentrations in Uterine Lymph and Systematic Blood . . . , Journal of Animal Science, vol. 57, pp. 449-455, ISU, 1983.
McGuffy, Irena, Softgel Technology as a Lipid-Based Delivery Tool for Bioavailability Enhancement, Catalent Pharma Solutions, Somerset, NJ, Mar. 2011.
Merck Index Online, Progesterone, Royal Society of Chemistry, 2013, search Feb. 17, 2014 https://www.rsc.org/Merck-Index/monograph/print/mono1500007889/progesterone?q=authorize.
Merck Index Online, Progesterone, Royal Society of Chemistry, 2013, search Feb. 24, 2014 https://www.rsc.org/Merck-Index/monograph/print/mono1500007889/progesterone?q=authorize.
Merck Index, Estradiol, The Merck Index Online, Royal Society of Chemistry 2014, MONO1500003758.
Mesley, R.J., Clathrate Formation from Steroids, Chemistry and Industry, vol. 37 pp. 1594-1595, Sep. 1965.
Miao, Wenbin, et al., Chemical Properties of Progesterone, SciFinder, 2014, American Chemical Society & US Natl. Lib. of Med.
Mueck, A.O., et al., Genomic and non-genomic actions of progestogens in the breast, J. Steroid Biochem. Mol.Biol. (2013), Elsevier.
Muramatsu, Mitsuo, Thermodynamic Relationship between a- and B-Forms of Crystalline Progesterone, J. Pharmaceutical Sciences, vol. 68(2) pp. 175-178, 1979, Amer. Pharm. Assoc.
Nicklas, Martina, Preparation and characterization of marine sponge collagen nanoparticles and employment for the trans . . . , Drug Devel. & Indust. Pharmacy,35(9) pp. 1035, 2009.
O'Leary, Peter, Salivary, but not serum or urinary levels of progesterone are elevated after topical . . . , Clinical Endocrinology, vol. 53 pp. 615-620, Blackwell Science 2000.
Open Notebook, Science Solubility Challenge, Jul. 16, 2013, Solubility of progesterone in organic solvents, http://lxsrv7.oru.edu/~alang/onsc/solubility/allsolvents.php?solute=progesterone.
Park, Jeong-Sook, Solvent effects on physicochemical behavior of estradiols recrystalized for transdermal delivery, Arch Pharm Res, vol. 31(1), pp. 111-116, 2008.

(56) References Cited

OTHER PUBLICATIONS

Park, Jeong-Sook, Use of CP/MAS solid-state NMR for the characterization of solvate . . . , European Journal of Pharmaceutics and Biopharmaceutics, vol. 60, pp. 407-412, 2005.
Parrish, Damon A., A new estra-1,3,5(10)-triene-3,17b-diol solvate: estradiol-methanol-water, Crystal Structure Comm., Intn'l Union of Crystallography, ISSN 0108-2701, 2003.
Payne, R.S., et al., Examples of successful crystal structure prediction: polymorphs of primidone and progesterone, Intl. Jour. of Pharma., vol. 177 pp. 231-245, 1999, Elsevier.
Persson, Linda C, et al., Physicochemical Properties of Progesterone Selecte, SciFinder, pp. 1-5, Feb. 24, 2014, American Chem. Society & US Natl. Lib. of Med.
Pheasant, Richard, Polymorphism of 17-Ethinylestradiol, Schering Corporation, Bloomfield, NJ, May 1950.
Pinkerton, J.V., Thomas, S., Use of SERMs for treatment in postmenopausal women, J. Steroid Biochem. Mol. Biol. (2014), Elsevier.
Pisegna, Gisia L, A High-pressure Vibrational Spectroscopic Study of Polymorphism in Steroids . . . , Thesis, McGill University, Dept. of Chem, Nov. 1999, Natl. Lib. of Canada.
Price, Sarah L, The computational prediction of pharmaceutical crystal structures and polymorphism, Adv. Drug Delivery Reviews, vol. 56 pp. 301-319, 2004, Elsevier.
Progynova TS 100, available online at file:///C:/Users/Call%20Family/Desktop/Progynova%20TS%20100%2012%20atches_Pack%20%28Estradiol%20Hemihydrate%29.html, 2010.
Rosilio, V, et al., Physical Aging of Progesterone-Loaded Poly(D,L,-lactide-co-glycolide) Microspheres, Pharmaceutical Research, vol. 15(5) pp. 794-99,1998, Plenum Pub. Corp.
Salole, Eugene G., Estradiol, Analytical Profiles of Drug Substances, vol. 15, pp. 283-318, 1986.
Santen, R.J., Menopausal hormone therapy and breast cancer, J. Steroid Biochem. Mol. Biol. (2013), Elsevier.
Sarkar, Basu, et al., Chemical Stability of Progesterone in Compounded Topical Preparations using PLO Transdermal Cream™ and HRT Cream™ Base . . . , J Steroids Horm Sci, 4:2, 2013.
Satyanarayana, D, et al., Aqueous Solubility Predictions of Aliphatic Alcohols, Alkyl Substituted Benzoates and Steroids, Asian J. Chem., vol. 9 (3) pp. 418-426, 1997.
Scavarelli, Rosa Maria, et al., Progesterone and Hydrate or Solvate, SciFinder, pp. 1-2, Feb. 24, 2014, American Chem. Society.
Schindler, A.E., The "newer" progestogens and postmenopausal hormone therapy (HRT), J. Steroid Biochem.Mol. Biol. (2013), Elsevier.
SciFinder Scholar Prednisone Chemical Properties, SciFinder, 2014, pp. 1-7, National Library of Medicine.
SciFinder Scholar Prednisone Physical Properties, SciFinder, 2014, pp. 1-10, Natioinal Library of Medicine.
SciFinder Scholar Progesterone Experimental Properties, SciFinder, pp. 1-9, Feb. 24, 2014, American Chem. Society.
Serantoni, Foresti, et al., 4-Pregnen-3,20-dione (progesterone, form II), Crystal Structure Comm., vol. 4(1) pp. 189-192, 1975, CAPLUS Database.
Sharma, H.C., et al., Physical Properties of Progesterone Selected Refer, SciFinder, pp. 1-5, Feb. 24, 2014, American Chem. Society & US Natl. Lib. of Med.
Sigma-Aldrich, Progesterone-Water Soluble: powder, BioReagent, suitable for cell culture), MSDS available online: http://www.sigmaaldrich.com/catalog/product/sigma/p7556.
Acarturk, "Mucoadhesive Vaginal Drug Delivery System," Recent Patents on Drug Delivery & Formulation, 3(3):193-205, 2009.
Fuchs et al., "The Effects of an Estrogen and Glycolic Acid Cream on the Facial Skin of Postmenopausal Women: A Randomized Histologic Study," Aesthetic Dermatology, 8(1):14-19, 2006.
Panay et al., "The 2013 British Menopause Society & Women's Health Concern recommendations on hormone replacement therapy," DOI: 0.1177/1754045313489645, min.sagepub.com. Menopause International: The Integrated Journal of Postreproductive Health 0(0):1-10, 2013.

Azeem et al., "Microemulsions as a Surrogate Carrier for Dermal Drug Delivery," Drug Development and Industrial Pharmacy, 35(5):525-547. 2009. Abstract Only.
Azure Pharma, Inc., "ELESTRIN™—Estradiol Gel" Drug Info, http://dailymed.nlm.nih.gov/dailymed/archives/fdaDrugInfo.cfm?archiveid=11885, 26 pages, 2009.
Chun et al., "Transdermal Delivery of Estradiol and Norethindrone Acetate: Effect of Vehicles and Pressure Sensitive Adhesive Matrix," J. Kor. Pharm. Sci., 35(3):173-177, 2005.
Committee of Obstetric Practice, Committee Opinion—No. 522, Obstetrics & Gynecology, 119(4):879-882, 2012.
Diramio, "Polyethylene Glycol Methacrylate/Dimetacrylate Hydrogels for Controlled Release of Hydrophobic Drugs," The University of Georgia—Masters of Science Thesis, 131 pages, 2004. http://athenaeum.libs.uga.edu/bitstream/handle/10724/7820/diramio_jackie_a_200412_ms.pdf?sequence=1.
Ganem-Quintanar et al., "Evaluation of the transepidermal permeation of diethylene glycol monoethyl ether and skin water loss," International Journal of Pharmaceutics, 147(2):165-171, 1997. Abstract Only.
Johanson, "Toxicity Review of Ethylene Glycol Monomethyl Ether and its Acetate Ester," Critical Reviews in Toxicology, 30(3):307-345, 2000. Abstract Only.
Knuth et al., "Hydrogel delivery systems for vaginal and oral applications: Formulation and biological considerations," Advanced Drug Delivery Reviews, 11(1-2):137-167, 1993. Abstract Only.
Lucy et al., "Gonadotropin-releasing hormone at estrus: luteinizing hormone, estradiol, and progesterone during the periestrual and postinsemination periods in dairy cattle," Biol Reprod., 35(2):300-11, 1986. Abstract Only.
NuGen, "What is NuGen HP Hair Growth System?" http://www.skinenergizer.com/Nugen-HP-Hair-Growth-System-p/senusystem.htm, 3 pages, undated.
NuGest 900™, http://www.thehormoneshop.net/nugest900.htm, 4 pages, undated.
Panchagnula et al., "Development and evaluation of an intracutaneous depot formulation of corticosteroids using Transcutol as a cosolvent: in-vitro, ex-vivo and in-vivo rat studies," J Pharm Pharmacol.;43(9):609-14, 1991. Abstract Only.
Salole, "The physiochemical properties of oestradiol," Journal of Pharmaceutical & Biomedical Analysis, 5(7):635-648, 1987.
Strickley, "Solubilizing Excipients in Oral and Injectable Formulations," Pharmaceutical Research, 21(2):201-230. 2004.
Tahition Noni, "Body Balance Cream," http://products.tni.com/dominican_republic/sa_spanish/nonistore/product/3438/3416/, 1 page, undated.
Trommer et al., "Overcoming the Stratum Corneum: The Modulation of Skin Penetration," Skin Pharmacol Physiol., 19:106-121, 2006. http://www.nanobiotec.iqm.unicamp.br/download/Trommer_skin%20penetration-2006rev.pdf.
International Search Report and Written Opinion for related International Application No. PCT/US13/023309 dated Apr. 9, 2013.
International Search report for corresponding International Application No. PCT/US12/66406, dated Jan. 24, 2013.
Abitec, CapmulMCM, EP, Technical Data Sheet, version 10, 2014, Columbus, OH.
Abitec, CapmulMCM, NF, Technical Data Sheet, version 6, 2014, Columbus, OH.
Abitec, CapmulMCM, Saftey Data Sheet, 2011, Janesville, WI.
Abitec, CapmulMCM, Technical Data Sheet, version 17, 2014, Columbus, OH.
Abitec, CapmulPG8, CAS No. 31565-12-5, version 11, 2006, Columbus, OH.
Alabi, K. A., et al., Analysis of Fatty Acid Composition of Thevetia peruviana and Hura crepitans Seed oils using GC-FID, Fountain Journal of Nat. and Appl. Sciences, vol. 2(2), pp. 32-37, 2013, Osogbo.
Alexander, KS, Corn Oil, CAS No. 8001-30-7, Jan. 2009.
British Pharmacopocia 2014 Online, Refined Maize Oil, Ph. Eur. Monograph 1342, vol. I & II, Monographs: Medicinal and Pharmaceutical Substances, http://www.pharmacopoeia.co.uk/bp2014/ixbin/bp.cgi?a=print&id=7400&tab=a-z%20index[Feb. 3, 2014 1:37:50 PM].

(56) References Cited

OTHER PUBLICATIONS

ChemPro, Top-Notch Technology in Production of Oils and Fats, Chempro-Edible-Oil-Refining-ISO-TUV-Austria.
Corn Refiners Assoc, Corn Oil, 5th Edition, Washington, D.C., 2006.
Dauqan, Eqbal M. A., et al., Fatty Acids Composition of Four Different Vegetable Oils (Red Palm Olein, Palm Olein, Corn Oil, IPCBEE, vol. 14, 2011, IACSIT Press, Singapore.
Ferrari, Roseli AP., et al., Oxidative Stability of Biodiesel From Soybean Oil Fatty Acid Ethyl Esters, Sci. Agric., vol. 62(3), pp. 291-295, 2005, Piracicaba, Braz.
Gunstone, Frank D, et al., Vegetable Oils in Food Technology: Composition, Properties and Uses, Blackwell Publishing, CRC Press, 2002.
Ng, Jo-Han, et al., Advances in biodiesel fuel for application in compression ignition engines, Clean Techn Environ Policy, vol. 12, pp. 459-493, 2010, Springer-Verlag.
Notelovitz, Morris, et al., Initial 17-b-Estradiol Dose for Treating Vasomotor Symptoms, Obstetrics & Gynecology, vol. 95(5), pp. 726-731, part 1, May 2000, Elsevier.
Prajapati, Hetal N, et al., A comparative Evaluation of Mono-, Di- and Triglyceride of Medium Chain Fatty Acids by Lipid/Surfactant/Water, Springerlink.com, pp. 1-21, Apr. 2011.
Strocchi, Antonino, Fatty Acid Composition, and Triglyceride Structure of Corn Oil, Hydrogenated Corn Oil, and Corn Oil Margarine, Journal of Food Science, vol. 47, pp. 36-39, 1981.
USP, 401 Fats and Fixed Oils, Chemical Tests, Second Suplement to USP36-NF 31, pp. 6141-6151, 2013.
USP, Lauroyl Polyoxylglycerides, Saftey Data Sheet, US, 5611 Version #02, pp. 1-9, 2013.
USP, Official Monographs, Corn Oil, NF 31, pp. 1970-1971, Dec. 2013.
USP, Official Monographs, Lauroyl Polyoxylglycerides, NF 31, pp. 2064-2066, Dec. 2013.
USP, Official Monographs, Medium Chain Triglycerides, NF 31, pp. 2271-2272, Dec. 2013.
USP, Official Monographs, Mono- and Di-glycerides, NF 31, pp. 2101, Dec. 2013.
USP, USP Certificate—Corn Oil, Lot G0L404, Jul. 2013.
Weber, E.J., Corn Lipids, Cereal Chem., vol. 55(5), pp. 572-584, The American Assoc of Cereal Chem, Sep.-Oct. 1978.
Araya-Sibaja, et al., Crystallization of progesterone polymorphs using polymer-induced heteronucleation (PIHn) method, Drug Development and Industrial Pharmacy, Early Online, pp. 1-8, 2014, Informa Healthcare.
PCCA, Apothogram, PCCA, May 2014, Houston, TX.
International Search Report and Written Opinion of International Application No. PCT/US2015/023041, Korean Intellectual Property Office, Republic of Korea, dated Jun. 30, 2015, 14 pages.
Sarpal, K., et al., "Self-Emulsifying Drug Delivery Systems: A Strategy to Improve Oral Bioavailability," *Current Research & Information on Pharmaceuticals Sciences* 11(3):42-49, Niper, India (Jul.-Sep. 2010).
Abdalla, A., et al., "A new self-emulsifying drug delivery system (SEDDS) for poorly soluble drugs: characterization, dissolution, in vitro digestion and incorporation into solid pellets," Eur J Pharm Sci 35(5):457-464, Elsevier, Netherlands (2008).
Falconer, J.R., et al., "The Effects of Supercritical Carbon Dioxide Processing on Progesterone Dispersion Systems: A Multivariate Study," AAPS Pharm. Sci. Tech. 13(4): 1255-1265, Springer, USA (2012).
Restriction Requirement, dated Feb. 6, 2013, in U.S. Appl. No. 13/684,002, Bernick, B.A., filed Nov. 21, 2012, 9 pages.
Office Action, dated Oct. 7, 2015, in U.S. Appl. No. 13/843,362, Bernick, B.A., filed Mar. 15, 2013, 12 pages.
Office Action, dated Jul. 15, 2016, in U.S. Appl. No. 13/843,362, Bernick, B.A., filed Mar. 15, 2013, 15 pages.
Office Action, dated Apr. 21, 2017, in U.S. Appl. No. 13/843,362, Bernick, B.A., filed Mar. 15, 2013, 13 pages.
Office Action, dated Jul. 2, 2015, in U.S. Appl. No. 13/843,428, Bernick, B.A., filed Mar. 15, 2013, 9 pages.
Notice of Allowance, dated Feb. 10, 2016, in U.S. Appl. No. 13/843,428, Bernick, B.A., filed Mar. 15, 2013, 10 pages.
Office Action, dated Oct. 26, 2015, in U.S. Appl. No. 14/106,655, Bernick, B.A., filed Dec. 13, 2013, 10 pages.
Office Action, dated Nov. 7, 2017, in U.S. Appl. No. 14/106,655, Bernick, B.A., filed Dec. 13, 2013, 12 pages.
Office Action, dated Mar. 30, 2016, in U.S. Appl. No. 14/106,655, Bernick, B.A., filed Dec. 13, 2013, 13 pages.
Office Action, dated Jun. 19, 2015, in U.S. Appl. No. 14/106,655, Bernick, B.A., filed Dec. 13, 2013, 11 pages.
Office Action, dated Mar. 23, 2017, in U.S. Appl. No. 14/106,655, Bernick, B.A., filed Dec. 13, 2013, 12 pages.
Notice of Allowance, dated Sep. 29, 2015, in U.S. Appl. No. 14/125,554, Bernick, B.A., filed Dec. 12, 2013, 9 pages.
Notice of Allowance, dated Aug. 4, 2015, in U.S. Appl. No. 14/136,048, Bernick, B.A., filed Dec. 20, 2013, 11 pages.
Notice of Allowance, dated Jun. 15, 2015, in U.S. Appl. No. 14/476,040, Bernick, B.A., filed Sep. 3, 2014, 9 pages.
Office Action, dated Jul. 20, 2016, in U.S. Appl. No. 14/521,230, Bernick, B.A., filed Oct. 22, 2014, 12 pages.
Office Action, dated Jun. 16, 2017, in U.S. Appl. No. 14/521,230, Bernick, B.A., filed Oct. 22, 2014, 13 pages.
Office Action, dated Oct. 8, 2015, in U.S. Appl. No. 14/624,051, Bernick B.A., filed Feb. 17, 2015, 7 pages.
Notice of Allowance, dated Feb. 1, 2016, in U.S. Appl. No. 14/624,051, Bernick B.A., filed Feb. 17, 2015, 6 pages.
Office Action, dated Sep. 28, 2017, in U.S. Appl. No. 15/454,898, Bernick, B.A., filed Mar. 9, 2017, 10 pages.

PROGESTERONE FORMULATIONS

CROSS-REFERENCE TO RELATED APPLICATIONS

This application is a National Stage application under 35 U.S.C. § 371 of International Application Ser. No. PCT/US2013/046442, entitled "PROGESTERONE FORMULATIONS" which was filed on Jun. 18, 2013, and claims priority to the following U.S. Patent Applications: U.S. Provisional Application Ser. No. 61/661,302, entitled "ESTRADIOL FORMULATIONS," which was filed on Jun. 18, 2012; U.S. Provisional Application Ser. No. 61/662,265, entitled "PROGESTERONE FORMULATIONS," which was filed on Jun. 20, 2012; U.S. patent application Ser. No. 13/684,002, entitled "NATURAL COMBINATION HORMONE REPLACEMENT FORMULATIONS AND THERAPIES," which was filed Nov. 21, 2012; U.S. Patent Application Ser. No. PCT/US2013/023309, entitled "TRANSDERMAL HORMONE REPLACEMENT THERAPIES," which was filed Jan. 25, 2013; U.S. patent application Ser. No. 13/843,362, entitled "TRANSDERMAL HORMONE REPLACEMENT THERAPIES," which was filed Mar. 15, 2013; and U.S. patent application Ser. No. 13/843,428, entitled "NATURAL COMBINATION HORMONE REPLACEMENT FORMULATIONS AND THERAPIES," which was filed Mar. 15, 2013. All aforementioned applications are hereby incorporated by reference herein in their entirety.

FIELD OF INVENTION

The disclosure relates to progesterone formulations. Various progesterone formulations may be used in hormone therapies for menopausal, peri-menopausal and post-menopausal females, for example, to mitigate side effects from estrogen replacement therapy. In addition, various progesterone formulations may be used to prevent preterm delivery in pregnant women having a shortened cervix.

BACKGROUND OF THE INVENTION

Hormone replacement therapy (HRT) is a medical treatment that involves the use of one or more of a group of medications designed to supplement hormone levels in women who lack adequate hormone production. It can mitigate and prevent symptoms caused by diminished circulating estrogen and progesterone hormones.

HRT is available in various forms. One therapy involves administration of low dosages of one or more estrogen(s) or one or more chemical analogues. Another involves administration of progesterone or one or more chemical analogues. Among other effects, progesterone administration acts to mitigate certain undesirable side effects from estradiol administration or naturally-occurring elevated blood levels including endometrial hyperplasia (thickening) and prevention or inhibition of endometrial cancer. Progesterone is a C-21 steroidal sex hormone involved in the female menstrual cycle, pregnancy (supports gestation) and embryogenesis of humans and other species. Progesterone belongs to a class of hormones called progestogens, and is the major naturally occurring human progestogen. Like other steroids, progesterone consists of four interconnected cyclic hydrocarbons. Progesterone is hydrophobic, having a reported aqueous solubility of 0.007±0.0 mg/ml. Progesterone is poorly absorbed when administered orally.

Conventional progesterone therapeutics include the administration of PROMETRIUM (progesterone, USP) (Abbott Laboratories, Chicago, Ill.). PROMETRIUM is an FDA-approved drug, formulated in a peanut oil-based medium, containing micronized progesterone, but with a relatively large particle size fraction.

The active ingredient is considered to be structurally identical to naturally occurring progesterone produced by a woman's body (also known as a "bioidentical).

Clinical trials involving PROMETRIUM have shown significant patient variability. For example, a clinical trial involving postmenopausal women who were administered PROMETRIUM once a day for five days resulted in the mean pharmacokinetic parameters listed in Table 1 (see Table 1, package insert for PROMETRIUM).

TABLE 1

Pharmacokinetic Parameters of PROMETRIUM Capsules

| Parameter | PROMETRIUM Capsules Daily Dose | | |
|---|---|---|---|
| | 100 mg | 200 mg | 300 mg |
| $C_{max}$ (ng/ml) | 17.3 ± 21.9 | 38.1 ± 37.8 | 60.6 ± 72.5 |
| $T_{max}$ (hr) | 1.5 ± 0.8 | 2.3 ± 1.4 | 1.7 ± 0.6 |
| AUC (0-10)(ngxhr/ml) | 43.3 ± 30.8 | 101.2 ± 66.0 | 175.7 ± 170.3 |

The unusually high variability in the Cmax and AUC, as evidenced by the large reported standard deviation, indicates that a significant percentage of patients are overdosed or receive a sub-optimal dose.

The presence of peanut oil in the formulation excludes patients who are allergic to peanut oil. Peanut oil, like other peanut products, may act as an allergen. Indeed, there is a portion of the population that has severe reactions to peanut oil. Peanut allergies are becoming a significant health concern. Food allergies are a leading cause of anaphylaxis, with approximately 200 deaths occurring annually in the United States. While incidence and prevalence are not entirely known, it is suspected that about 6% of children and 4% of adults in North America are affected by food allergies. Many food allergies experienced by children are generally outgrown in adulthood with the exception of peanut allergies.

Progesterone and its analogues can be used to treat a variety of medical conditions, including acute diseases or disorders, as well as chronic diseases and disorders associated with long-term declines of natural progesterone levels.

Accordingly, improved formulations of progesterone would be advantageous.

SUMMARY OF THE INVENTION

Various pharmaceutical formulations are disclosed herein. For example, pharmaceutical formulations are disclosed comprising ultra-micronized progesterone. Moreover, pharmaceutical formulations are disclosed comprising formulations of ultra-micronized progesterone, wherein the ultra-micronized progesterone is combined with a suitable excipient.

Thus, in various illustrative embodiments, the invention comprises an encapsulated liquid pharmaceutical formulation for orally administering progesterone to a mammal in need thereof, said formulation comprising: progesterone, as the sole active pharmaceutical ingredient, in micronized form, in solubilized form, or in micronized and partially soluble form in a carrier that comprises a medium chain fatty acid-glycol ester or mixtures thereof and a non-ionic surfactant comprising a polyethylene glycol fatty acid ester. In some such embodiments the progesterone is ultra-micronized. In some such embodiments, at least about 80 wt % of the total progesterone is micronized. The fatty acids can be predominantly (>50 wt %): C6 to C12 fatty acids, C6 to C10 fatty acids, C8 to C12 fatty acids, or C8 to C10 fatty acids, the esters can be mono-, di-, or triesters or mixtures thereof, and the glycols can be glycerol, polyethylene glycol or propylene glycol or mixtures thereof. Some embodiments comprise a non-ionic surfactant that comprises C8 to C18 fatty acid esters of glycerol and polyethylene glycol.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure.

DETAILED DESCRIPTION OF THE ILLUSTRATED EMBODIMENTS

Figure 1:
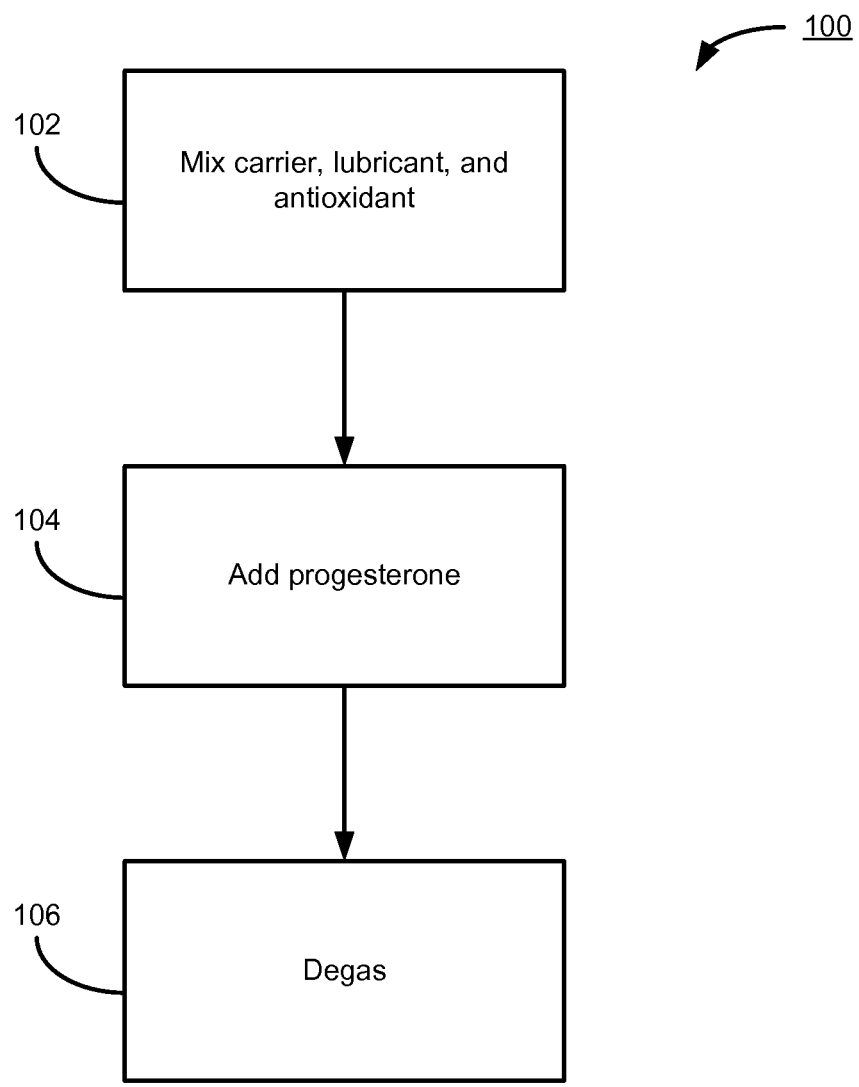
FIG. 1 illustrates a process to produce fill material in accordance with various embodiments.

According to various embodiments, a pharmaceutical formulation comprising ultra-micronized progesterone is provided. As described in detail here, various carriers, lubricants, and other excipients may be included. In further embodiments, ultra-micronized progesterone formulations provide improved bioavailability and other pharmacokinetic improvements.

Definitions

Unless otherwise specified, the following definitions apply.

The term "ultra-micronized progesterone," as used herein, includes micronized progesterone having an X50 value below about 20 microns and/or having an X90 value below about 25 microns.

A chemical structure of progesterone is depicted below:

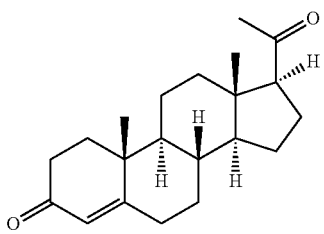

The term "administer," "administration," "deliver" or "delivery" (collectively "administration"), as used herein, means administration to the body via, without limitation, tablets, capsules, softgel capsules, injections, transdermal patches, creams, gels, vaginal suppositories including gelcaps or other mechanisms known in the art or hereinafter developed. The term "administration" may also mean direct application of softgel contents into the vagina, such as by accessing the softgel contents opening or rupturing the softgel capsule to liberate the contents therein.

The term "X50," as used herein, means that half of the particles in a sample are smaller in diameter than a given number. For example, ultra-micronized progesterone having an X50 of 5 microns means that, for a given sample of ultra-micronized progesterone, half of the particles have a diameter of less than 5 microns. In that regard, similar terms, in the form XYY mean that YY percent of the particles in the sample are smaller in diameter than a given number. For example, X90 means that ninety percent of the particles in a sample are smaller in diameter than a given number.

The term "medium chain," as used herein means any medium chain carbon-contain substance, including C4-C18, and including C6-C12 substances, fatty acid esters of glycerol, fatty acids, and mono-, di-, and tri-glycerides of such substances. For further illustration, C6-C14 fatty acids, C6-C12 fatty acids, and C8-C10 fatty acids are all medium chain fatty acids and may be used in instances in which this specification calls for use of medium chain fatty acids, e.g., medium chain fatty acid esters of glycerol or other glycols.

The term "uniform distribution" means at least one of uniform dispersion, solubility, or lack of agglomeration of progesterone in gastric juices compared to PROMETRIUM.

The term "gastric juices" means the watery, acidic digestive fluid that is secreted by various glands in the mucous membrane of the stomach and consists chiefly of hydrochloric acid, pepsin, rennin, and mucin.

The term, "API," as used herein, refers to active pharmaceutical ingredient. In formulations, the API is progesterone.

The term "excipients," as used herein, refers to non-API substances such as carriers, solvents, lubricants and others used in formulating pharmaceutical products. They are generally safe for administering to humans according to established governmental standards, including those promulgated by the United States Food and Drug Administration.

The term "carrier," as used herein, means any substance or mixture of substances that may be mixed with or contain an API (e.g., ultra-micronized progesterone).

The term "capsule," as used herein, refers to a generally safe, readily dissolvable enclosure for carrying certain pharmaceutical products, and includes hard or soft shell capsules.

The term "softgel," includes soft shell capsules, including soft-gelatin capsules and soft vegetable-based capsules, and soft capsules made from other materials providing the composition of such soft capsules are compatible with the formulations of the various embodiments described herein. A softgel may comprise two primary phases: a gel or vegetable-based capsule and a fill material of the pharmaceutical formulation as described herein.

The term "bioavailability," as used herein means the concentration of an active ingredient (e.g., progesterone) in the blood (serum or plasma). The relative bioavailability may be measured as the concentration in the blood (serum or plasma) versus time. Other pharmacokinetic (PK) indicators may be used to measure and assess bioavailability, determined by suitable metrics including AUC, $C_{max}$ and optionally $T_{max}$.

The terms "pharmacokinetics" and "pharmacokinetic measurements" include assessments and determinations to study absorption, distribution, metabolism, and excretion of a drug.

The term "AUC," as used herein, refers to the area under the curve that represents changes in blood concentration of progesterone over time.

The term, "$C_{max}$" as used herein, refers to the maximum value of blood concentration shown on the curve that represents changes in blood concentrations of progesterone over time.

The term, "$T_{max}$" as used herein, refers to the time that it takes for progesterone blood concentration to reach the maximum value.

Optionally, the term, "$T_{1/2}$" as used herein, refers to the time that it takes for progesterone blood concentration to decline to one-half of the maximum level.

Collectively AUC, $C_{max}$, and optionally $T_{max}$ and $T_{1/2}$, are the principle pharmacokinetic parameters that can characterize the pharmacokinetic responses of a particular drug product such as progesterone in an animal or human subject.

DESCRIPTION

Generally, the pharmaceutical formulations described herein are prepared and administered as filled capsules, typically soft capsules of one or more materials well known in the art including, for example and without limitation, soft gelatin capsules. Micronized progesterone, as described herein, may also be prepared for administration in tablets or other well-known orally administered dosage forms using standard techniques.

Another aspect of the present disclosure includes a pharmaceutical formulation of micronized progesterone, micronized progesterone with partially solubilized progesterone, and fully solubilized progesterone, wherein said formulation may provide increased progesterone bioavailability in a treated subject compared to the bioavailability provided by Prometrium® when administered at equal dosage strengths.

In illustrative embodiments, total progesterone, i.e., dissolved and micronized, is 20 to 50 wt %, e.g., 30 to 35 wt %, based on the weight of the entire fill, i.e., the liquid pharmaceutical formulation.

Other embodiments disclosed herein further provide: more uniform dissolution of progesterone, and reduced intra- and inter-patient blood level variability in formulations of progesterone of the present disclosure, when compared to equal dosages of PROMETRIUM. Blood level variability is also compared at equal sampling times following administration.

According to the PROMETRIUM prescribing information, clinical trials have shown significant patient variability. For example, a clinical trial involving postmenopausal women who were administered PROMETRIUM once a day for five days resulted in the mean PK parameters listed in the following table:

|  | PROMETRIUM Capsules Daily Dose | | |
| --- | --- | --- | --- |
| Parameter | 100 mg | 200 mg | 300 mg |
| $C_{max}$ (ng/ml) | 17.3 +/− 21.9 | 38.1 +/− 37.8 | 60.6 +/− 72.5 |
| $T_{max}$ (hr) | 1.5 +/− 0.8 | 2.3 +/− 1.4 | 1.7 +/− 0.6 |
| $AUC_{0-10}$ (ngxhr/ml) | 43.4 +/− 30.8 | 101.2 +/− 66.0 | 175.7 +/− 170.3 |

In particular illustrative aspects and embodiments of this invention, it is possible, though not necessary, to reduce the standard deviations in one or more of these PK parameters.

More uniform dissolution of progesterone in a formulation of the present disclosure compared to the dissolution of PROMETRIUM at equal dosage strengths and using the same USP apparatus can be determined using standard techniques established for API dissolution testing, including that which is described in the examples below.

Reduced intra- and inter-patient variability of progesterone formulated pursuant to the present disclosure compared to PROMETRIUM can be demonstrated via a fed bio-study such as that described below.

Other aspects of the present disclosure include the use of formulations as described herein wherein progesterone is at least one API in said formulation for the treatment of an animal, especially a mammal, including humans: for endometrial hyperplasia; for secondary amenorrhea; as a method of treatment for preterm birth, when said animal has a shortened cervix, and other disease states or conditions treated with supplemental progesterone (collectively, "Progesterone-deficient States") in a subject in need of treatment, and with a non-toxic effective amount of said formulations. As used herein, the term "treatment", or a derivative thereof, contemplates partial or complete inhibition of the stated disease state when a formulation as described herein is administered prophylactically or following the onset of the disease state for which such formulation is administered. For the purposes of the present disclosure, "prophylaxis" refers to administration of the active ingredient(s) to an animal especially a mammal, to protect the animal from any of the disorders set forth herein, as well as others.

Exemplary dosage strengths for progesterone for use in the formulations described herein include, without limitation, 25, 50, 75, 100, 125, 150, 175, 200 mg, 250 mg, 300 mg, 350 mg and 400 mg.

Progesterone active pharmaceutical ingredient may be micronized via any one of the multiple methods typically utilized by the ordinarily skilled artisan.

Particle size may be determined in any suitable manner. For example, a Beckman Coulter LS 13 320 Laser Diffraction Particle Size Analyzer (the "Beckman Device") may be used to determine particle size. Particle size may be represented by various metrics, for example, through an X50 particle size, and/or X90 particle size, or similar descriptions of particle size.

The Beckman Device may be used with various modules for introducing a sample for analysis. The Beckman Device may be used with the LS 13 320 Universal Liquid Module ("ULM"). The ULM is capable of suspending samples in the size range of 0.017 μm to 2000 nm. The ULM is a liquid based module that allows for delivery of the sample to the sensing zone. The ULM recirculates the sample through the Beckman Device. The ULM comprises two hoses, one for fluid delivery and another for waste. The total volume used may be 125 mL or less. A sample mass of from about 1 mg to about 10 g may be used. The ULM may interact with the Beckman Device via pins that fit into slots on the ULM. The ULM may use a variety of suspension fluids, for example, water, butonol, ethanol, chloroform, heptanes, toluene, propanol, COULTER Type 1B Dispersant ("Coulter 1B"), and a variety of other suspension fluids. Surfactants may also be used, though pump speed should be adjusted to prevent excessive bubbling. Coulter 1B may comprise one or more of acetaldehyde, ethylene oxide, and/or 1,4-dioxane. The Beckman Device may be configured to use a variety of optical theories, including the Fraunhofer optical model and the Mie Theory.

The Beckman Device may comprise software to control the Beckman Device while the ULM is in use. The software may control, for example, pump speed, use of de-bubble routine, rinse routine, sonicate routine, and fill routine, among others. Parameters regarding the sample run may also be configured. For example, run length may be set. Though any suitable run length may be used, in various embodiments, a time period of 30 seconds to 120 seconds, and preferably between 30 seconds and 90 seconds may be used.

The Beckman Device may be used with the LS 13 320 Micro Liquid Module ("MLM"). The MLM is capable of suspending samples in the size range of 0.4 µm to 2000 µm. The MLM is a liquid based module that allows for delivery of the sample to the sensing zone. The MLM includes a stirrer. The total volume used may be 12 mL or less. The MLM may use a variety of suspension fluids, both aqueous and non-aqueous.

In various embodiments, ultra-micronized progesterone has an X50 value of less than about 15 microns, less than about 10 microns, less than about 5 microns and/or less than about 3 microns; and an X90 value of less than about 25 microns, less than about 20 microns, and/or less than about 15 microns.

In various embodiments, ultra-micronized progesterone is formulated with peanut and peanut-oil free excipients.

In various embodiments, the carrier is selected to enhance dissolution and suspension properties of progesterone. In further various embodiments, the carrier is selected to enhance absorption of the API by cells of a mammal. For example, certain carriers may be selected to enhance absorption of the other formulation components, including the API. Absorption may comprise absorption into any cell and particularly absorption into digestive system cells, such as intestinal cells, and cells of the female reproductive system, such as the vagina and the cervix. Selected mono/di/triglycerides are particularly suited to aid in cellular absorption In various embodiments, the carrier may comprise medium chain fatty acids. Suitable carriers include caproic fatty acid; caprylic fatty acid; capric fatty acid; lauric acid; myristic acid; linoleic acid; succinic acid; glycerin; propylene glycol; caprylic/capric triglycerides; caproic/caprylic/capric/lauric triglycerides; caprylic/capric/linoleic triglycerides; caprylic/capric/succinic triglycerides; polyethylene glycol; propylene glycol dicaprylate/dicaprate; and combinations and derivatives thereof.

Suitable carriers further include esters of saturated coconut and palm kernel oil and derivatives thereof, including fractionated coconut oils and palm kernel oils thereof; and triglycerides of fractionated vegetable fatty acids, and derivatives thereof and combinations thereof. In further various embodiments, the carrier may comprise one or more monoglycerides, diglycerides, triglycerides, and combinations thereof such a suitable carrier is available commercially under the trademark MIGLYOL (caprylic/capric triglyceride) (Sasol Germany, GmbH). MIGLYOL products comprise esters of saturated coconut and palm kernel oil-derived caprylic and capric fatty acids, glycerin and/or propylene glycol. Suitable MIGLYOL products include MIGLYOL 810 (Caprylic/Capric Triglyceride) MIGLYOL 812 (Caprylic/Capric Triglyceride), MIGLYOL 818 (Caprylic/Capric/Linoleic Triglyceride) and MIGLYOL 829 (Caprylic/Capric/Succinic Triglyceride).

Additional examples include a polyethylene glycol glyceride (Gelucire®; GATTEFOSSE SAS, Saint-Priest, France); a propylene glycol; a caproic/caprylic/capric/lauric triglyceride; a caprylic/capric/linoleic triglyceride; a caprylic/capric/succinic triglyceride; propylene glycol monocaprylate; propylene glycol monocaprate; (Capmul® PG-8 and 10; the CAPMUL brands are owned by ABITEC, Columbus Ohio); propylene glycol dicaprylate; propylene glycol dicaprylate; medium chain mono- and di-glycerides (CAPMUL MCM); a diethylene glycol mono ester (including 2-(2-Ethoxyethoxy)ethanol:Transcutol); diethylene glycol monoethyl ether; esters of saturated coconut and palm kernel oil and derivatives thereof; triglycerides of fractionated vegetable fatty acids, and combinations and derivatives thereof. In other aspects and embodiments, progesterone is fully solubilized using, for example and without limitation, sufficient amounts of: TRANSCUTOL (Diethylene glycol monoethyl ether) and MIGLYOL; TRANSCUTOL, MIGLYOL and CAPMUL PG-8 (Propylene Glycol Monocaprylate) and/or CAPMUL PG-10 (Propylene Glycol Monocaprate); CAPMUL MCM (Medium Chain Mono- and Diglycerides); CAPMUL MCM and a non-ionic surfactant; and CAPMUL MCM and GELUCIRE (a polyethylene glycol glyceride).

Various ratios of these oils can be used for suspension and/or solubilization of progesterone. CAPMUL MCM and a non-ionic surfactant, e.g., GELUCIRE 44/14 (Lauroyl macrogol-32 glycerides EP Lauroyl polyoxyl-32 glycerides NF Lauroyl polyoxylglycerides (USA FDA IIG)), can be used at ratios of about 99:1 to 2:1, including, for example and without limitation: 60:40, 65:35, 70:30, 75:25, 80:10, 80:15, 85:20, 90:10, and 98:1. The ratios of oil (e.g., medium chain fatty acid esters of monoglycerides and diglycerides) to non-ionic surfactant can be significantly higher. For example, in certain examples, below, CAPMUL MCM and GELUCIRE were used in ratios of up to about 65:1, e.g., 8:1, 22:1, 49:1, 65:1 and 66:1. Thus, useful ratios can be, e.g., 8:1 or greater, e.g., 60 to 70:1.

Combinations of these oils can produce partially solubilized progesterone, depending upon the desired unit dosage amount of progesterone. The greater the amount of progesterone per unit dosage form, the less progesterone may be solubilized. The upward limit of dosage strength per unit dose it generally limited only by the practical size of the final dosage form.

In illustrative embodiments, oils used to suspend, partially solubilize, or fully solubilize progesterone include medium chain fatty acid esters, (e.g., esters of glycerol, polyethylene glycol, or propylene glycol) and mixtures thereof. In illustrative embodiments, the medium chain fatty acids are C6 to C14 or C6 to C12 fatty acids. In illustrative embodiments, the medium chain fatty acids are saturated, or predominantly saturated, e.g., greater than about 60% or greater than about 75% saturated. In illustrative embodiments, progesterone is soluble in the oils at room temperature, although it may be desirable to warm certain oils initially during manufacture to improve viscosity. In illustrative embodiments, the oil or oil/surfactant is liquid at between room temperature and about 50° C., e.g., at or below 50° C., at or below 40° C., or at or below 50° C. In illustrative embodiments, GELUCIRE 44/14 is heated to about 65° C. and CAPMUL MCM is heated to about 40° C. to facilitate mixing of the oil and non-ionic surfactant, although such heating is not necessary to dissolve the estradiol or progesterone.

In illustrative embodiments, the solubility of estradiol in the oil (or oil/surfactant) is at least about 0.5 wt %, e.g., 0.8 wt % or higher, or 1.0 wt % or higher. Illustrative examples of mono- and diglycerides of medium chain fatty acids include, among others, CAPMUL MCM, CAPMUL MCM C10 (Glyceryl Monocaprate), CAPMUL MCM C8 (Glyceryl Monocaprylate), and CAPMUL MCM C8 EP (Glyceryl Monocaprylate). These oils are C8 and C10 fatty acid mono- and diglycerides. Illustrative examples of oils that are triglycerides of medium chain fatty acids include, among others, MIGLYOL 810 and MIGLYOL 812.

Illustrative examples of oils that are medium chain fatty acid esters of propylene glycol include, among others, CAPMUL PG-8, CAPMUL PG-2L EP/NF (Propylene Glycol Dilaurate), CAPMUL PG-8 NF (Propylene Glycol Monocaprylate), CAPMUL PG-12 EP/NF (Propylene Glycol Monolaurate) and CAPRYOL (Propylene glycol monocaprylate (type II) NF). Other illustrative examples include MIGLYOL 840 (Propylene Glycol Dicaprylate/Dicaprate).

Illustrative examples of oils that are medium chain fatty acid esters of polyethylene glycol include, among others, GELUCIRE 44/14 (PEG-32 glyceryl laurate EP), which is polyethylene glycol glycerides composed of mono-, di- and triglycerides and mono- and diesters of polyethylene glycol. Without intending to be bound to any particular mechanism, it appears that at least in formulations comprising small amounts of GELUCIRE, e.g., 10 wt % or less, the primary function of this oil is as a non-ionic surfactant.

These illustrative examples comprise predominantly medium chain length, saturated, fatty acids, specifically predominantly C8 to C12 saturated fatty acids.

It will be understood that commercially available fatty acid esters of glycerol and other glycols are often prepared from natural oils and therefore may comprise components additional to the fatty acid esters that comprise the predominant (by weight) component(s) and that therefore are used to characterize the product. Such other components may be, e.g., other fatty acid triglycerides, mono- and diesters, free glycerol, or free fatty acids. So, for example, when an oil/solubilizing agent is described herein as a saturated C8 fatty acid mono- or diester of glycerol, it will be understood that the predominant component of the oil, i.e., >50 wt % (e.g., >75 wt %, >85 wt % or >90 wt %) are caprylic monoglycerides and caprylic diglycerides. For example, the Technical Data Sheet by ABITEC for CAPMUL MCM C8 describes CAPMUL MCM C8 as being composed of mono and diglycerides of medium chain fatty acids (mainly caprylic) and describes the alkyl content as <=1% C6, >=95% C8, <=5% C10, and <=1.5% C12 and higher.

By way of further example, MIGLYOL 812 is generally described as a C8-C10 triglyceride because the fatty acid composition is at least about 80% caprylic (C8) acid and capric (C10) acid. However, it can also comprise small amounts of other fatty acids, e.g., less than about 5% of caproic (C6) acid, lauric (C12) acid, and myristic (C14) acid.

Specifically, a product information sheet for MIGLYOL by SASOL provides the composition of fatty acids as follows:

| Tests | 810 | 812 | 818 | 829 | 840 |
|---|---|---|---|---|---|
| Caproic acid (C6:0) | max. 2.0 | max. 2.0 | max. 2 | max. 2 | max. 2 |
| Caprylic acid (C8:0) | 65.0-80.0 | 50.0-65.0 | 45-65 | 45-55 | 65-80 |
| Capric acid (C10:0) | 20.0-35.0 | 30.0-45.0 | 30-45 | 30-40 | 20-35 |
| Lauric acid (C12:0) | max. 2 | max. 2 | max. 3 | max. 3 | max. 2 |
| Myristic (C14:0) acid | max. 1.0 | max. 1.0 | max. 1 | max. 1 | max. 1 |
| Linoleic acid (C18:2) | — | — | 2 -5 | — | — |
| Succinic acid | — | — | — | 15-20 | — |

Where certain embodiment of this invention are described as comprising (or consisting essentially of) a capsule shell, estradiol solubilized in C8-C10 triglycerides, and a thickening agent, it will be understood that the fatty acid esters component of the formulation may be, e.g., MIGLYOL 812 or a similar product.

By way of further illustration, GELUCIRE 44/14 is generally described as lauroyl polyoxyl-32 glycerides, i.e., polyoxyethylene 32 lauric glycerides (which is a mixture of mono-, di-, and triesters of glycerol and mono- and diesters of PEGs) because the fatty acid composition is 30 to 50% lauric acid and smaller amounts of other fatty acids, e.g., up to 15% caprylic acid, up to 12% capric acid, up to 25% myristic acid, up to 25% palmitic acid, and up to 35% stearic acid. The product may also contain small amounts of non-esterified glycols. Where certain embodiment of this invention are described as comprising (or consisting essentially of) a capsule shell, estradiol solubilized in triglycerides, and a thickening agent that is a non-ionic surfactant comprising C8 to C18 fatty acid esters of glycerol and polyethylene glycol, it will be understood that the thickening agent component of the formulation may be, e.g., GELUCIRE 44/14 or a similar product.

Similarly, where certain embodiment of this invention are described as comprising (or consisting essentially of) a capsule shell, estradiol solubilized in triglycerides, and a thickening agent that is a non-ionic surfactant comprising PEG-6 stearate, ethylene glycol palmitostearate, and PEG-32 stearate, it will be understood that the thickening agent component of the formulation may be, e.g., TEFOSE 63 (PEG-6 palmitostearate and ethylene glycol palmitostearate) or a similar product.

In illustrative embodiments of the invention, the selected oil does not require excessive heating in order to solubilize progesterone. For example, when the formulation comprises medium chain fatty acid mono- and diglycerides (e.g., CAPMUL MCM) and polyethylene glycol glycerides (e.g., GELUCIRE) as a surfactant, the oil and/or the surfactant can be warmed up, e.g., to about 65 C in the case of the surfactant and less in the case of the oil, to facilitate mixing of the oil and surfactant. The progesterone can be added as the mixture cools, e.g., to below about 40 C or to below about 30 C, even down to room temperature.

In certain embodiments, an anionic and/or a non-ionic surfactant is used. Exemplary non-ionic surfactants may include one or more of glycerol and polyethylene glycol esters of fatty acids, for example, lauroyl macrogol-32 glycerides and/or lauroyl polyoxyl-32 glycerides, commercially available as GELUCIRE, including, for example, GELUCIRE 44/11 and GELUCIRE 44/14. These surfactants may be used at concentrations greater than about 0.01%, and typically in various amounts of about 0.01%-10.0%, 10.1%-20%, and 20.1%-30%. In certain examples, below, GELUCIRE 44/14 is used as a surfactant in amounts of 1 to 10 wt %. See, Tables below. Other non-ionic surfactants include, e.g., LABRASOL (Caprylocaproyl macrogol-8 glycerides EP Caprylocaproyl polyoxyl-8 glycerides NF PEG-8 Caprylic/Capric Glycerides (USA FDA IIG))(Gattefosse) and LABARAFIL (corn/apricot oil PEG-6 esters) (Gattefosse).

In various embodiments, a lubricant is used. Any suitable lubricant may be used, such as, for example and without limitation, lecithin, and in various embodiments, a mixture of polyethylene glycol ("PEG") esters, glycerides, and PEG, such as is commercially available under the trade name GELUCIRE (Gattefosse, FR) may also be used as a lubricant. Suitable lubricants may also comprise calcium stearate, ethyl oleate, ethyl laureate, glycerin, glyceryl palmitostearate, hydrogenated vegetable oil, magnesium, oxide, magnesium stearate, poloxamer, glycols, and phospholipid mixtures. In particular, a mixture of polyethylene glycol esters, glycerides, and PEG such as GELUCIRE 44/14, may be used as a lubricant. GELUCIRE 44/14 is a non-ionic water dispersible surfactant, also known as lauroyl macrogol-32 glycerides EP and lauroyl polyoxyl-32 glycerides NF. In various embodiments, GELUCIRE 44/14 acts as a suspension agent.

In various embodiments, an antioxidant is used. Any suitable antioxidant may be used, such as, for example and without limitation, butylated hydroxytoluene. Butylated hydroxytoluene, a derivative of phenol, is lipophilic and is thus suited to being intermixed with ultra-micronized progesterone and carriers disclosed or contemplated herein.

For example, in various embodiments, a pharmaceutical formulation comprises about 20% to about 80% carrier by weight, about 0.1% to about 5% lubricant by weight, and about 0.01% to about 0.1% antioxidant by weight.

The choice of excipient will, to a large extent, depend on factors such as the particular mode of administration, the effect of the excipient on solubility and stability, and the nature of the dosage form. Excipients used in various embodiments may include colorants, flavoring agents, preservatives and taste-masking agents. Colorants, for example, may comprise about 0.1% to about 2% by weight. Preservatives may comprise methyl and propyl paraben, for example, in a ratio of about 10:1, and at a proportion of about 0.005% and 0.05% by weight.

As is with all oils, solubilizers, excipients and any other additives used in the formulations described herein, each is to be non-toxic and pharmaceutically acceptable.

As referenced above, the formulations of the present disclosure are generally orally administered, typically via, for example, capsules such as soft capsules. The present formulations can also be used to form transdermal patches using standard technology known in the art. Solubilized formulations of the present invention can also be formulated for intraperitoneal administration using techniques well known in the art.

Thus, an illustrative embodiment of a pharmaceutical composition of the invention comprises progesterone, at least 75% of the progesterone being solubilized (the balance being micronized as discussed elsewhere herein), and an oil, wherein the oil is medium chain fatty acid mono- and diesters of one or more glycols, with or without surfactant. In certain embodiments, a specification for progesterone is set at >80% solubilized, <20% micronized or >85% solubilized, <15% micronized.

Pharmaceutical formulations in accordance with various embodiments comprise ultra-micronized progesterone. In further embodiments, a pharmaceutical formulation comprises ultra-micronized progesterone, a carrier, and a lubricant. In still further embodiments a pharmaceutical formulation comprises ultra-micronized progesterone, a carrier, a lubricant, and optionally an antioxidant. In still further embodiments, a pharmaceutical formulation comprises ultra-micronized progesterone, and a medium chain triglyceride as a carrier. In still further embodiments, a pharmaceutical formulation comprises ultra-micronized progesterone, and monoglycerides/diglycerides/triglycerides of caprylic/capric acid as a carrier. Various further embodiments also comprise lecithin and optionally butylated hydroxytoluene.

In additional embodiments, a pharmaceutical formulation comprises ultra-micronized progesterone and at least one carrier, a lubricant, optionally an antioxidant, and other pharmaceutically acceptable excipients. For example, in various embodiments, a pharmaceutical formulation comprises about 20% to about 80% carrier by weight, about 0.1% to about 5% lubricant by weight, and about 0.01% to about 0.1% antioxidant by weight.

The choice of excipient will, to a large extent, depend on factors such as the particular mode of administration, the effect of the excipient on solubility and stability, and the nature of the dosage form. Excipients used in various embodiments may include colorants, flavoring agents, preservatives and taste-masking agents. Colorants, for example, may comprise about 0.1% to about 2% by weight. Preservatives may comprise methyl and propyl paraben, for example, in a ratio of about 10:1, and at a proportion of about 0.005% and 0.05% by weight.

Formulations in accordance with various embodiments may be administered alone or combination with one or more other drugs (or as any combination thereof). For example, formulations in accordance with various embodiments may also comprise estradiol.

In various embodiments, ultra-micronized progesterone is administered in a capsule. Capsules may be prepared using one or more film forming polymers. Suitable film forming polymers include natural polymers, such as gelatin, and synthetic film forming polymers, such as modified celluloses. Suitable modified celluloses include, but are not limited to, hydroxypropyl methyl cellulose, methyl cellulose.

Hard or soft shell capsules can be used to administer the API. In certain embodiments, capsules may be prepared by forming the two capsule halves, filling one of the halves with the fill solution, and then sealing the capsule halves together to form the finished capsule.

Hard shell capsules may be prepared by combining the "Body" and the "Cap". The "Body" of the capsule is filled with the "fill mass" and then closed with the "Cap". The "Body"/"Cap" interface is then sealed/banded.

Soft gelatin capsules may be prepared using a rotary die encapsulation process, as further described below.

Suitable shell additives, for either a hard or soft shell capsules, may include plasticizers, opacifiers, colorants, humectants, preservatives, flavorings, and buffering salts and acids, and combinations thereof. The main ingredients of the capsule shell is primarily gelatin (or a gelatin substitute for non-gelatin capsules), plasticizer, and purified water. Hard shell and soft shell capsules differ primarily in the amount of plasticizer present that is used in the capsule shell.

Plasticizers are chemical agents added to gelatin to make the material softer and more flexible. Suitable plasticizers include, but are not limited to, glycerin, sorbitol solutions which are mixtures of sorbitol and sorbitan, and other polyhydric alcohols such as propylene glycol and maltitol or combinations thereof.

Opacifiers are used to opacify the capsule shell when the encapsulated active agents are light-sensitive. Suitable opacifiers include titanium dioxide, zinc oxide, calcium carbonate and combinations thereof.

Colorants can be used for marketing and product identification/differentiation purposes. Suitable colorants include synthetic and natural dyes and combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to minimize cross-linking of the gelatin.

In accordance with various embodiments, a softgel dosage form is used.

A softgel comprises two primary phases: a gel capsule and a fill material. The softgel may comprise a gelatin material in a relatively solid or stiff form. The softgel may define an inner volume that may contain the fill material. Dissolution of the softgel may commence at various points, such as along the digestive tract (mouth, esophagus, stomach and intestines), or other body cavities, such as the vaginal cavity.

As the softgel dissolves, the inner volume may come into fluid communication with the digestive system, allowing the fill material to leach outside the softgel. A softgel may also be punctured, cut, or otherwise opened outside a body. The fill material may then be poured or squeezed outside the gel capsule and applied on or in the body, such as within the vaginal cavity.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl esters (collectively known as "parabens") or combinations thereof.

The fill material may comprise a liquid, such as an oil, a solution, a suspension, or other acceptable forms. The active ingredient or active ingredient may be contained within the liquid.

Formulations in accordance with various embodiments may be administered orally. Oral administration may involve swallowing, so that the compound enters the gastrointestinal tract, or buccal or sublingual administration may be employed by which the compound enters the blood stream directly from the mouth.

Ultra-micronized progesterone in accordance with various embodiments may be formulated as a vaginal suppository or vaginal cream for administration onto the vulva or into the vagina, cervix, or uterus of a human. Capsules (e.g., softgels) containing ultra-micronized progesterone also may be administered vaginally, including insertion of a capsule directly into the vaginal cavity or delivery of such capsule contents into the vaginal cavity. Ultra-micronized progesterone, in accordance with various embodiments, may be formulated for intraperitoneal administration, and atomization, such as with nasal mist administration.

In accordance with various embodiments, enhanced bioavailability of progesterone is provided, such as over conventional progesterone formulations wherein it is well known that commercially available formulations of progesterone are poorly or inconsistently absorbed. While not bound by theory, the elements of the present formulation provide the enhanced performance characteristics as further described herein, including, for example and without limitation, improved bioavailability and the potential to be able to reduce the administered dosage strength compared to presently available progesterone formulations. Bioavailability comparisons to commercially available forms, such as tablet forms, may be determined by standard pharmacokinetic techniques In accordance with various embodiments, food effects are reduced, e.g., relative to comparative progesterone products.

In accordance with various embodiments, formulations do not include peanut oil. The lack of peanut oil obviates the risk posed to those having peanut-based allergies.

Capsules may be arranged in blisters or cartridges or bottles.

According to various embodiments, a 28-day or monthly regimen of capsules can be packaged in a single kit (e.g., a blister pack) having delivery days identified to improve compliance and reduce associated symptoms, among others. One or more of the capsules may contain no estradiol, for example, and/or no progesterone. Capsules that comprise no API or hormone (e.g., progesterone) may be referred to as placebos. A blister pack can have a plurality of scores or perforations separating blister pack into 28 days. Each day may further comprise a single blister or a plurality of blisters. In various embodiments, each dose (e.g., each softgel) may contain ultra-micronized progesterone in amounts of 100 mg, 150 mg, 200 mg, and 250 mg, though other dose ranges are contemplated herein. In addition, kits having other configurations are also contemplated herein. For example, without limitation, kits having such blister packs may contain any number of capsules.

Formulations in accordance with various embodiments may be used to treat or prevent preterm delivery in pregnant women, including in certain women having a shortened cervix. In various embodiments, a capsule, for example a softgel capsule, may be opened and the fill material applied in or around the vagina. However, in various embodiments the capsules are taken orally.

Formulations in accordance with various embodiments may be used to treat or prevent endometrial hyperplasia.

Formulations in accordance with various embodiments may be used to treat or prevent secondary amenorrhea.

Formulations in accordance with various embodiments may be used to mitigate or treat the effects of estradiol supplementation. In particular, formulations in accordance with various embodiments may be co-administered with estradiol and/or co-formulated with estradiol.

Formulations in accordance with various embodiments may be used to treat menopause-related symptoms, including vasomotor symptoms, for example, in relation to treatment of hypoestrogenism related symptoms including hot flashes and night sweats (vasomotor symptoms), sleep disturbances, mood changes, vulvo-vaginal atrophy; and osteoporosis and endometrial hyperplasia reduction.

Additional objects of the present disclosure include: providing increased patient compliance secondary to ease of use; providing increased physician adoption secondary to ease of use/instruction with less worry of side effects from inappropriate usage; providing decreased side-effects from erroneous use (decreased irregular bleeding); providing better efficacy/control of symptoms secondary to appropriate use; reducing the metabolic and vascular side effects of the commonly used synthetic progestins when administered alone or in combination with an estrogen (norethindrone acetate, medroxyprogesterone acetate, etc.) including, for example, stroke, heart attacks, blood clots and breast cancer.

Specific Embodiments

Through extensive trial-and-error testing of various fatty acid esters of glycerol and other glycols, embodiments of the invention have been invented that have one or more favorable characteristics for development as a human drug product. Such favorable characteristics include those described above, e.g., improved PK and reduced variability.

Such embodiments include an encapsulated liquid pharmaceutical formulation for orally administering progesterone to a mammal in need thereof, said formulation comprising: progesterone, as the sole active pharmaceutical ingredient, in micronized form suspended in a carrier that comprises a medium chain fatty acid-glycol ester or mixtures thereof and a non-ionic surfactant comprising a polyethylene glycol fatty acid ester.

A more specific such embodiment is such formulation wherein the progesterone is ultramicronized.

In certain such embodiments, the progesterone is suspended and/or solubilized in one or more C6 to C12 fatty acid mono-, di-, or triesters of glycerol, e.g., one or more C6 to C14 triglycerides, e.g., one or more C6 to C12 triglycerides, such as one or more C8-C10 triglycerides. An example of a carrier that provides beneficial properties is C8, C10, or C8 and C10 saturated triglycerides, such as but not limited to MIGLYOL, e.g., MIGLYOL 812.

In such general and more specific embodiments, the non-ionic surfactant is a polyethylene glycol saturated or unsaturated fatty acid ester or diester. In certain such embodiments, the non-ionic surfactant comprises C8 to C18 fatty acid esters of glycerol and polyethylene glycol. An example of a non-ionic surfactant that provides beneficial properties is GELUCIRE, e.g., GELUCIRE 44/14.

In certain such embodiments, the non-ionic surfactant has a HLB value of about 15. An illustrative example of such surfactant is GELUCIRE 44/14.

As noted above, such formulations are liquid at room temperature, not gels, hard fats, or any other solid form. The non-ionic surfactant serves to increase viscosity. In some such embodiments, the non-ionic surfactant, e.g., GELUCIRE or TEFOSE, may be solid at room temperature and require melting to effect mixing with the estradiol solubilized in fatty acid-glycol esters but the resultant formulation is advantageously liquid, not solid.

The formulation of such embodiments is typically encapsulated in a soft gelatin capsule or other soft capsule.

Typically, such formulations do not comprise a bioadhesive (i.e., muco-adhesive) agent, a gelling agent, or a dispersing agent, or, at least, do not comprise one or two of such components.

In more specific such formulations, the capsule shell, the active pharmaceutical ingredient, the fatty acid esters and the non-ionic surfactant are the only essential ingredients. Non-essential ingredients, e.g., colorants, antioxidants or other preservatives, etc., may, of course, be included but other ingredients in amounts that would materially change the solubility of the progesterone, the PK of the encapsulated formulation, or other clinically relevant properties, e.g., other oils or fatty acid esters, lecithin, muco-adherent agents, gelling agents, dispersing agents, or the like would not be included. Such embodiments of the invention may be described as consisting essentially of the capsule shell, the active pharmaceutical ingredient, the fatty acid esters and the non-ionic surfactant, as described in the immediately preceding paragraphs describing illustrative embodiments discovered to have favorable characteristics.

As an example of such embodiments discovered to have such favorable characteristics is mentioned the product identified in Example 2, Table 3, below.

EXAMPLES

Example 1

In an exemplary embodiment, a capsule is provided containing a fill material comprising:

TABLE 2

| Ingredient | mg/Capsule | % | Function |
|---|---|---|---|
| Ultra-micronized Progesterone | 200.00 | 30.77 | Active |
| Medium Chain Triglyceride (MIGLYOL 812 or equivalent) | qs | qs | Carrier |
| Lecithin Liquid | 1.63 | 0.25 | Lubricant/Emulsifier |
| Butylated Hydroxytoluene (also referred to as "BHT") | 0.13 | 0.02 | Antioxidant |

The above formulation is prepared as follows: MIGLYOL is heated to about 45° C. GELUCIRE 44/14 is added and mixed until dissolved. BHT is added and mixed until dissolved. Progesterone is suspended and passed through a colloid mill. The resultant fill mass can be used for encapsulation.

Example 2

In an exemplary embodiment, a capsule is provided containing a fill material comprising:

TABLE 3

| Ingredient | % | mg/Capsule | Function |
|---|---|---|---|
| 1. Ultra-micronized Progesterone | 30.77 | 200.00 | Active |
| 2. Medium Chain Triglyceride (MIGLYOL 812 or equivalent) | 65.93 | 428.55 | Carrier |
| 3. Lauroyl polyoxyl-32-glycerides (GELUCIRE 44/14 or equivalent) | 3.00 | 19.50 | Suspending Agent |
| 4. Butylated Hydroxytoluene | 0.03 | 1.95 | Antioxidant |
| Total | 100 | 650 | |

In various embodiments, amounts of MIGLYOL may be present in a range from about 35-95% by weight; GELUCIRE 44/14 from about 0.5-30% by weight; and BHT from about 0.01-0.1% by weight.

Example 3

Progesterone Solubility

In various embodiments, both estradiol and progesterone may be dissolved in a solvent. In various embodiments, the solubility of both estradiol and progesterone will be such that a therapeutically effective dose may be obtained in a reasonably sized mass, generally considered to be between 1 mg and 1200 mg, preferably suitable for encapsulation in a size 3 to 22 oval or oblong capsule. For example, in various embodiments, 50 mg to 100 mg of progesterone may be dissolved in a volume of solvent; i.e., the solubility would be 50 mg to 100 mg per capsule. MIGLYOL was attempted, and while it can be considered a good carrier for progesterone, it alone did not provide a desirable level of solubilization of estradiol (e.g., solubility of 12 mg/g may be desirable in various embodiments). Thus, MIGLYOL, including without limitation MIGLYOL 812, may be used in embodiments comprising a suspension of progesterone.

As can be seen in Table 9, the solubility of progesterone in CAPMUL MCM is ~73 mg/g. Therefore, by suspending 200 mg progesterone in 400 mg of solvent, part of the dose (~14%) is already dissolved and the remaining is still a suspension. In some aspects and embodiments, it is desired to minimize the partial solubility of progesterone in the formulation in order to minimize the possibility of recrystallization.

Based on 73 mg/g solubility, the capsule size required to make a capsule of 50 mg solubilized progesterone would be 685 mg.

TABLE 4

| Ingredient | Progesterone Solubility (mg/g) |
|---|---|
| CAPMUL MCM | 73.4 |
| CAPMUL PG8 | 95 |
| MIGLYOL 812 | 27.8 |
| CAPMUL MCM: GELUCIRE 44/14 (9:1) | 86.4 |
| CAPMUL MCM: GELUCIRE 44/14 (7:3) | 70.5 |
| CAPMUL MCM: GELUCIRE 44/14 (6:3) | 57.4 |

In addition, it has been found that the solubility of progesterone in a solvent of CAPMUL MCM in combination with GELUCIRE 44/14 in a 9:1 ratio increases the solubility to approximately 86 mg/g. Therefore, in various embodiments, progesterone and/or estradiol may be dissolved in a CAPMUL MCM and GELUCIRE 44/14 system, wherein the ratio of CAPMUL MCM to GELUCIRE 44/14 is 9:1.

TABLE 5

| Ingredient | Progesterone Solubility (mg/g) |
|---|---|
| CAPMUL MCM:GELUCIRE 44/14 (9:1) | 86.4 |
| CAPMUL MCM:GELUCIRE 44/14 (7:3) | 70.5 |
| CAPMUL MCM:GELUCIRE 44/14 (6:4) | 57.4 |

Example 4

In an exemplary embodiment, a capsule is provided containing a fill material having suspended progesterone comprising:

TABLE 6

| Ingredient | mg/Capsule | % | Function |
|---|---|---|---|
| Micronized Progesterone | 200.00 | 30.77 | Active |
| Medium Chain Triglyceride (MIGLYOL 812 or equivalent) | qs | qs | Carrier |
| Lecithin Liquid | 1.63 | 0.25 | Lubricant/Emulsifier |
| Butylated Hydroxytoluene (also referred to as "BHT") | 0.13 | 0.02 | Antioxidant |

The above formulation is prepared as follows: MIGLYOL is heated to about 45° C. GELUCIRE 44/14 is added and mixed until dissolved. BHT is added and mixed until dissolved. Progesterone is suspended and passed through a colloid mill. The resultant fill mass can be used for encapsulation.

In an exemplary embodiment, a capsule is provided containing a fill material having partially solubilized progesterone comprising:

TABLE 7

| Ingredient | Qty/Capsule (mg) | % w/w | Qty/Capsule (mg) | Amount/Batch (kg) |
|---|---|---|---|---|
| Micronized Progesterone, USP | 200.00 | 33.33 | Active | 2.0 |
| Monoglycerides/diglycerides/triglycerides of caprylic/capric acid (CAPMUL MCM) | 394.0 | 65.67 | Carrier | 3.94 |
| Lauroyl polyoxyl-32-glycerides (GELUCIRE 44/14 or equivalent) | 6.0 | 1 | Lubricant/Emulsifier | 0.06 |
| Total | 600.00 mg | 100 | | 6.0 kg |

For suspensions of progesterone and partially solubilized progesterone, GELUCIRE 44/14 may be added at 1% to 2% w/w to increase viscosity. The above formulation is prepared as follows: CAPMUL MCM is heated to about 65° C. GELUCIRE 44/14 is added and mixed until dissolved. Heat is removed. Progesterone is added and the mixture is passed through a colloid mill. The resultant fill mass can be used for encapsulation.

Example 5

In an exemplary embodiment, a capsule is provided containing a fill material having suspended progesterone comprising:

TABLE 8

| Ingredient | % | mg/Capsule | Function |
|---|---|---|---|
| Micronized Progesterone | 30.77 | 200.00 | Active |
| Medium Chain Triglyceride (MIGLYOL 812 or equivalent) | 65.93 | 428.55 | Carrier |
| Lauroyl polyoxyl-32-glycerides (GELUCIRE 44/14 or equivalent) | 3.00 | 19.50 | Suspending Agent |
| Butylated Hydroxytoluene | 0.03 | 1.95 | Antioxidant |
| Total | 100 | 650 | |

In various embodiments, amounts of MIGLYOL may be present in a range from about 35-95% by weight; GELUCIRE 44/14 from about 0.5-30% by weight; and BHT from about 0.01-0.1% by weight.

Example 6

Bioavailability Assessment—Fasted

A randomized single-dose oral bioequivalence study comparing 200 mg ultra-micronized progesterone capsule test product (T) and 200 mg PROMETRIUM® (progesterone) capsules (Abbott Laboratories, Abbott Park, Ill.) reference product (R) is conducted. Subjects are administered a single 200 mg dose of either test product (T) or the reference product (R) under fasting conditions, for example, subjects fasted at least 10.0 hours prior to dosing. Blood is collected pre-dose and post-dose. Pre-dose samples are collected at approximately −01.00, −00.50, and 00.00 hours. Post-dose samples are collected at approximately 01.00, 02.00, 03.00, 04.00, 05.00, 06.00, 07.00, 08.00, 09.00, 10.00, 12.00, 18.00, 24.00, 36.00 and 48.00 hours. Standard meals are provided at 04.00, 09.00, 13.00, 25.00, 29.00, 33.00 and 37.00 hours post-dose.

Pharmacokinetic measurements are assessed including $C_{max}$, AUC and optionally $T_{max}$. Comparative bioavailability of the test product (T) and reference product are assessed.

Example 7

Bioavailability Assessment—Fed

The procedures for determining bioavailability under fasted conditions are repeated except that subjects are administered a single 200 mg dose of either test product (T) or reference product (R) immediately following a high fat meal, for example, within 30 minutes of dosing. Blood is collected pre-dose and post-dose. Pre-dose samples are collected at approximately −01.00, −00.50, and 00.00 hours. Post-dose samples are collected at approximately 01.00, 02.00, 03.00, 04.00, 05.00, 06.00, 07.00, 08.00, 09.00, 10.00, 12.00, 18.00, 24.00, 36.00 and 48.00 hours. Standard meals are provided at 04.00, 09.00, 13.00, 25.00, 29.00, 33.00 and 37.00 hours post-dose. Pharmacokinetic measurements are assessed including $C_{max}$, AUC and optionally $T_{max}$. Bioavailability of the test product (T) in reference to the reference product is assessed. The effect of food on the comparative bioavailability of the test product (T) and the reference product (R) are also assessed.

Example 8

Figure 2:
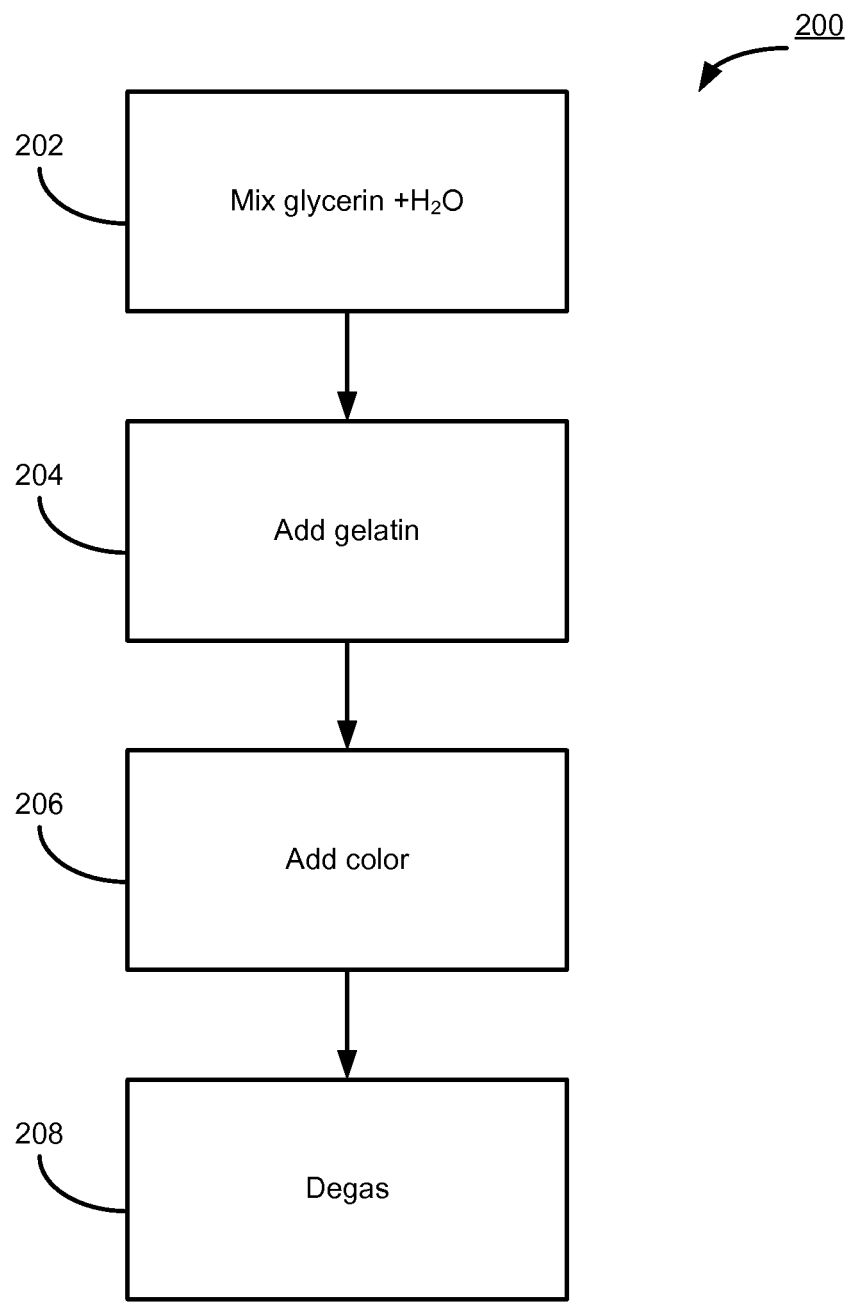
FIG. 2 illustrates a process to produce softgel capsules in accordance with various embodiments.
Figure 3:
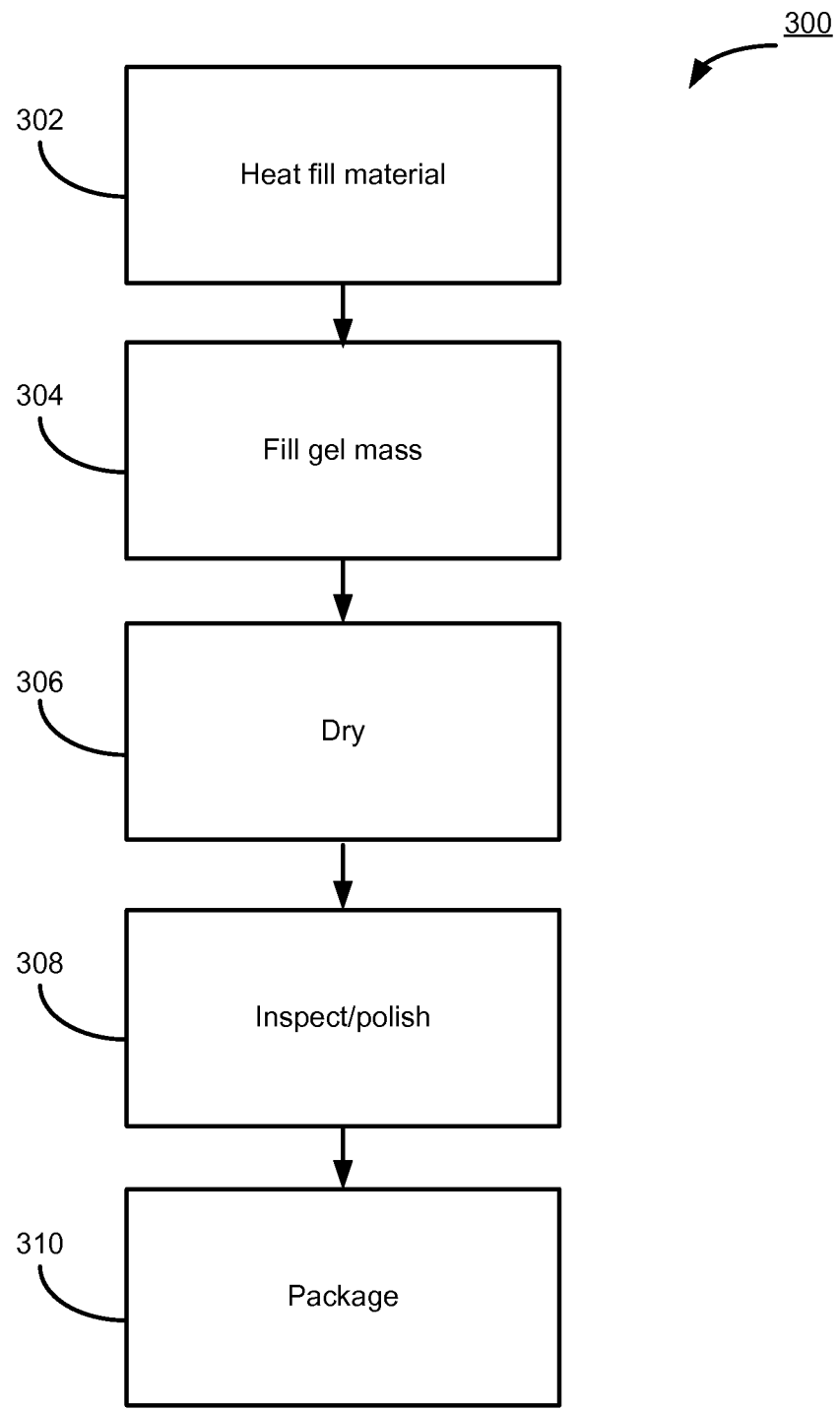
FIG. 3 illustrates a process to produce softgel capsules in accordance with various embodiments.

Method of manufacture in accordance with various embodiments are shown in FIGS. 1-3. With reference to FIG. 1, method of fill material, i.e. fill mass, preparation 100 is shown. Step 102 comprises mixing a carrier, a lubricant, and an antioxidant as described herein. For example, lecithin and butylated hydroxytoluene may be mixed with one or more medium chain mono-, di- or triglycerides, or combinations thereof mixing may be facilitated by an impellor, agitator, or other suitable means. Step 102 may be performed under an inert or relatively inert gas atmosphere, such as nitrogen gas $N_2$. Mixing may be performed in any suitable vessel, such as a stainless steel vessel.

Step 104 may comprise mixing ultra-micronized progesterone into the mixture of the carrier, the lubricant, and the antioxidant. A pasty substance is thus formed. Mixing may occur in a steel tank or vat. Mixing may be facilitated by an impellor, agitator, or other suitable means. Step 104 may be performed under an inert or relatively inert gas atmosphere, such as nitrogen gas $N_2$. Step 106 comprises degasing. The resulting mixture from step 106 may comprise a fill material suitable for production into a softgel capsule.

With reference to FIG. 2, softgel capsule, i.e. gel mass, production 200 is shown. Step 202 comprises mixing glycerin with water. The water used in step 202 may be purified by any suitable means, such as reverse osmosis, ozonation, filtration (e.g., through a carbon column) or the like. Mixing may be facilitated by an impellor, agitator, or other suitable means. Step 202 may be performed under an inert or relatively inert gas atmosphere, such as nitrogen gas $N_2$. Heating may be performed until the temperature reaches 80°±5° C.

Step 204 comprises the addition of gelatin to the glycerin water mixture. Mixing may be facilitated by an impellor, agitator, or other suitable means. Step 204 may be performed under an inert or relatively inert gas atmosphere, such as nitrogen gas $N_2$. A vacuum may be drawn in step 204 to de-aerate.

Step 206 comprises addition of a coloring agent such as a dye. A coloring agent may comprise products sold under the trademark OPATINT or other suitable agent. Step 206 may be performed under an inert or relatively inert gas atmosphere, such as nitrogen gas $N_2$. Step 208 comprises degasing. The resulting mixture from step 208 may comprise a gel capsule material suitable for use as a gel capsule in production of a softgel capsule.

With reference to FIG. 3, softgel capsule assembly process 300 is shown. Step 302 comprises heating the fill material. The fill material may be heated to any suitable temperature. In various embodiments, the fill material is heated to 30° C.+/−3° C. Fill material maybe heated in a fill hopper. A fill hopper may comprise a device configured to hold a volume of the fill material and/or to dispense the fill material in controlled volumes.

Step 304 comprises filling a gel mass. A gel mass may be taken from the gel capsule material produced in step 208 of FIG. 2. Filling may be performed by injecting, placing, or otherwise disposing the fill material within a volume defined by the gel capsule material. The filling may occur in an encapsulator. The spreader boxes may be a temperature of 55° C.+/−10° C. The wedge temperature may be 38° C.+/−3° C. The drum cooling temperature may be 4° C.+/−2° C. The encapsulator may be lubricated using MIGLYOL 812. Step 304 thus produces one or more softgel capsules. Filling may comprise producing a ribbon of thickness 0.85±0.05 mm using spreader box knobs. The fill material may be injected into the gel to produce a fill weight having target weight ±5% (i.e., 650±33 mg and 325±16.3 mg).

Step 306 comprises drying the softgel capsules. Drying may be performed in a tumble dryer, tray dryer, or combinations thereof. For example, drying may be performed in a tumble drying basket for between about 10 minutes and about 120 minutes. Drying may continue in a drying room for about 24 hours to about 72 hours. Polishing may be performed with isopropyl alcohol.

Example 9

Stability Study

In accordance with various embodiments, formulations in accordance with various embodiments have an exemplary shelf life of 3 months with storage at 25±2° C./60±5% RH in 75 cc HDPE white, opaque bottles with a 38/400 mm white child resistant cap.

Packaging during testing comprises a 75 cc round HDPE bottle and 33 mm cap. A Brasken FPT 300F resin is associated with the cap. Testing criteria include visual appearance, assay of progesterone, dissolution, content uniformity and microbial limits testing.

Three test groups are created. Test group 1 comprises a test at 40° C./75% RH. Test group 2 comprises a test at 30° C./65% RH. Test group 3 comprises a test at 25° C./60% RH. Test group 1 is tested for visual appearance, assay of ultra-micronized progesterone, and dissolution at months 1, 2, 3, and 6. Test group 2 is tested for visual appearance, assay of ultra-micronized progesterone, and dissolution at months 0, 1, 2, 3, 6, and 12. Test group 3 is tested for visual appearance, assay of ultra-micronized progesterone, and dissolution at months 0, 1, 2, 3, 6, 12 and 24.

Example 10

A particle size analysis is conducted by using a Beckman Coulter LS 13 320 Laser Diffraction Particle Size Analyzer (the "Beckman Device"). The Beckman Device uses laser diffraction to determine particle size. A sample of a formulation in accordance with various embodiments is provided. The Beckman Device particle sensor yields that the sample has an X50 of 6.67 µm, an X75 of 14.78 µm, and an X25 of 2.193 µm.

Example 11

A dissolution study was performed using a formulation in accordance with various embodiments. The results of the dissolution study are shown in FIG. 4.

The dissolution study was performed using a United States Pharmacopoeia dissolution apparatus 3 (reciprocating cylinder) ("USP Apparatus 3"). The USP Apparatus 3 was set to 30 dips per minute. Two hundred fifty mL (250 mL) of a solution of 1N HCL with 3% sodium lauryl sulfate was used at 37° C.

Figure 4:
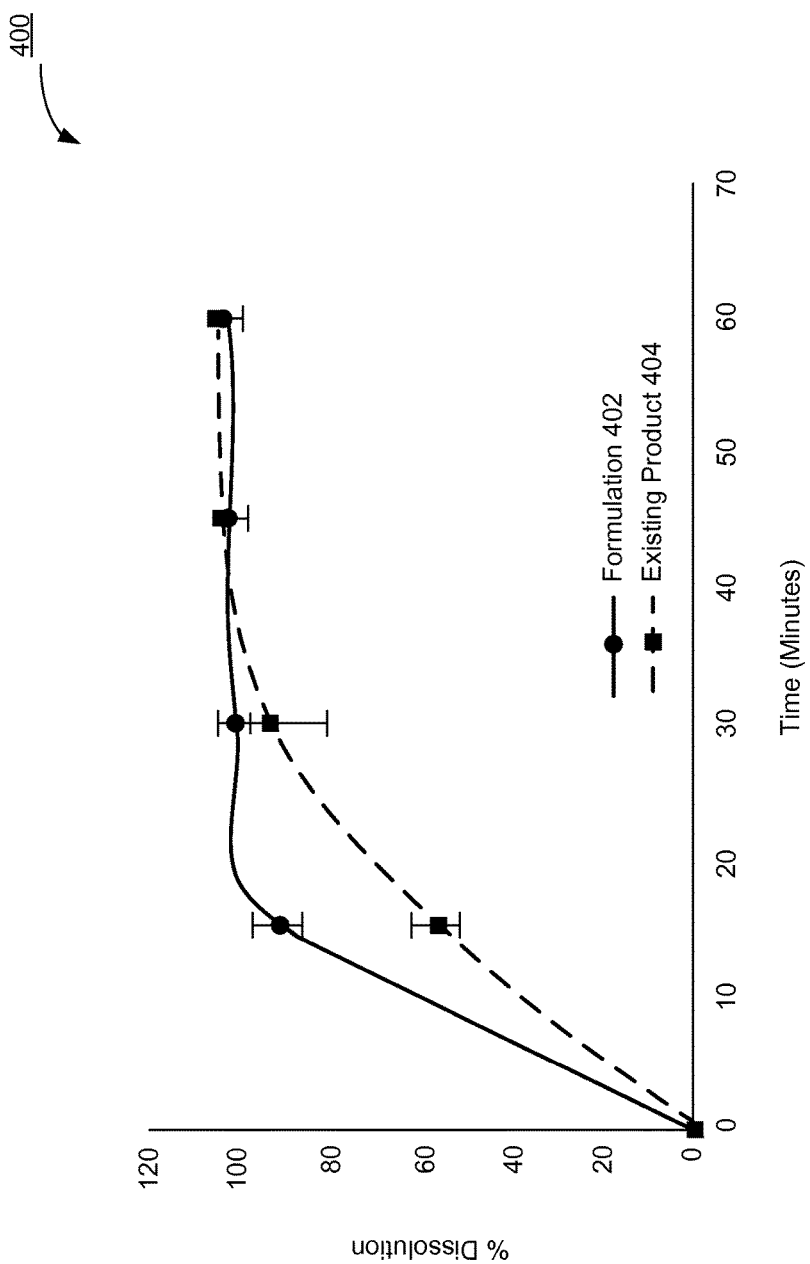
FIG. 4 illustrates a dissolution study of a formulation in accordance with various embodiments.

FIG. 4 shows dissolution percentage in the y axis over time in minutes on the x axis. A formulation in accordance with various embodiments is shown having circular dots, and is labeled formulation 402. An existing commercial pharmaceutical product containing progesterone is shown having square dots and is labeled existing product 404. As shown in FIG. 4, formulation 402 reaches a higher level of dissolution in a shorter time than existing product 404.

Example 12

For the purposes of this Example, a particle size analysis is conducted by using the Beckman Device. A sample API comprising micronized progesterone in accordance with various embodiments is provided for analysis.

Figure 5:
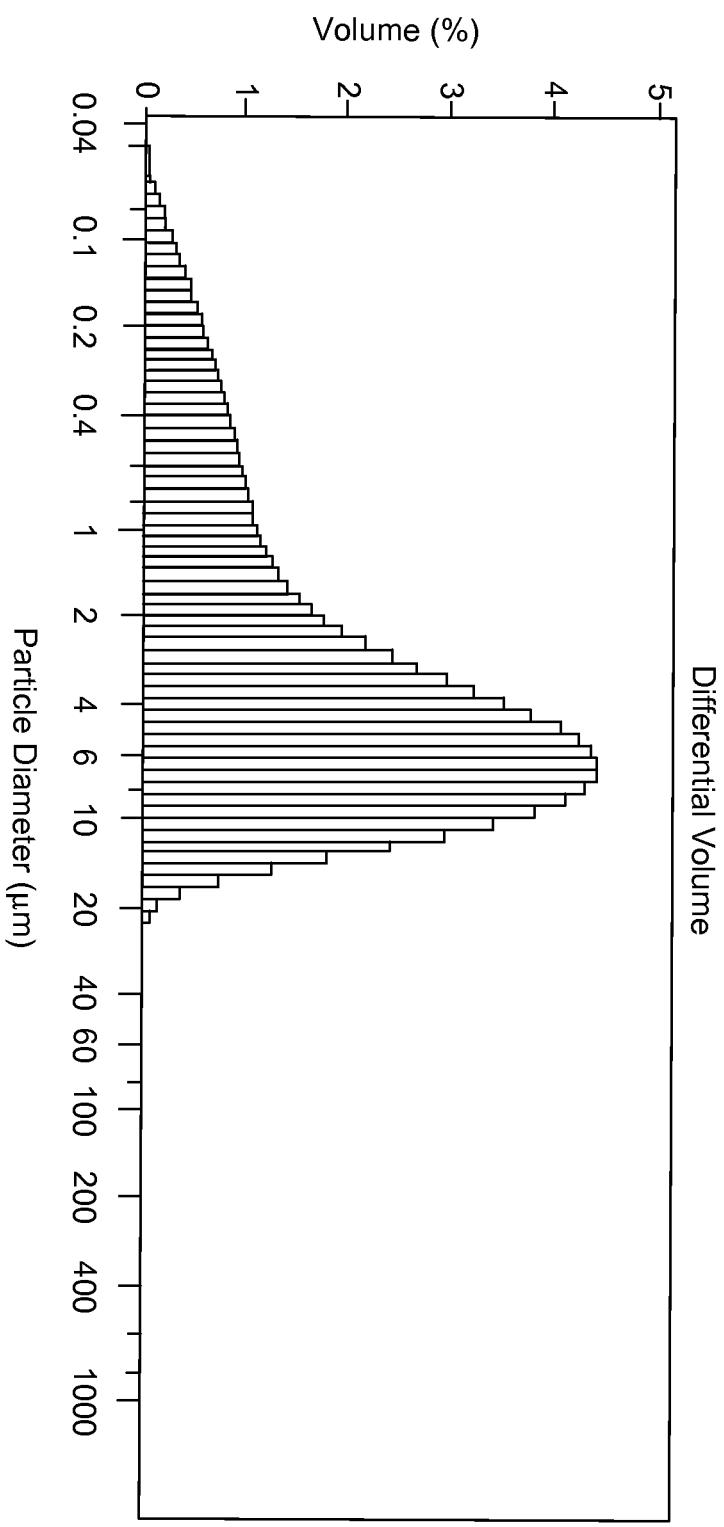
FIG. 5 illustrates a graph of the particle distribution obtained in Example 10.

Approximately 0.01 g of a sample API in accordance with various embodiments was combined with Coulter 1B and 10 mL of deionized water. Sonication was performed for 15 seconds. The Beckman Device, equipped with a ULM, performed analysis for 90 seconds. The Beckman Device was configured to use the Fraunhofer optical model. The Beckman Device yielded that the sample has an X50 of 4.279 μm, an X75 of 7.442 μm, and an X25 of 1.590 μm. The Beckman Device also yielded that the mean particle size is 4.975 μm, the median particle size is 4.279 μm, the mode particle size is 6.453 μm, and the standard deviation is 3.956 μm. A graph of the particle distribution obtained is shown in FIG. 5.

Example 13

Study 352—Progesterone and Estradiol Combination Study under Fed Conditions. This following study protocol was used to establish bio-availability and bio-equivalence parameters for a combination product of the present disclosure comprising progesterone (200 mg) and estradiol (2.0 mg) as prepared via the process described in Example 14 and compared to 200 mg of PROMETRIUM® (Catalent Pharmaceuticals, St. Petersburg, Fla. (and 2.0 mg of ESTRACE (estradiol vaginal cream, USP, 0.01%) (Bristol-Myers Squibb Co. Princeton, N.J.), administered to twenty-four (24) normal healthy, adult human post-menopausal female subjects under fed conditions.

The pharmaceutical formulation of the invention used in these PK studies had substantially the following formula:

| Ingredient(s) | Amount (% w/w) | Qty/Capsule (mg) |
|---|---|---|
| Progesterone, USP, micronized | 7.14 | 50.00 |
| Estradiol Hemihydrate, USP Micronized | 0.30 | 2.07 |
| CAPMUL MCM, NF, USP | 83.27 | 582.93 |
| GELUCIRE 44/14, NF | 9.29 | 650 |
| Total | 100.00 | 700 |

The Study Design: An open-label, balanced, randomized, two-treatment, two-period, two-sequence, single-dose, two-way crossover study.

The subjects were housed in the clinical facility from at least 11.00 hours pre-dose to at least 48.00 hours post-dose in each period, with a washout period of at least 14 days between the successive dosing days.

Subjects were fasted for at least about 10.00 hours before being served a high-fat, high-calorie breakfast, followed by dosing, then followed by a 04.00 hour, post-dose additional period of fasting.

Standard meals were provided at about 04.00, 09.00, 13.00, 25.00, 29.00, 34.00 and 38.00 hours post-dose, respectively.

Water was restricted at least about 01 hour prior to dosing until about 01 hour post-dose (except for water given during dosing). At other times, drinking water was provided ad libitum.

Subjects were instructed to abstain from consuming caffeine and/or xanthine containing products (i.e. coffee, tea, chocolate, and caffeine-containing sodas, colas, etc.) for at least about 24.00 hours prior to dosing and throughout the study, grapefruit and\or its juice and poppy containing foods for at least about 48.00 hours prior to dosing and throughout the study.

Subjects remained seated upright for about the first 04.00 hours post-dose and only necessary movements were allowed during this period. Thereafter subjects were allowed to ambulate freely during the remaining part of the study. Subjects were not allowed to lie down (except as directed by the physician secondary to adverse events) during restriction period.

Subjects were instructed not to take any prescription medications within 14 days prior to study check in and throughout the study. Subjects were instructed not to take any over the counter medicinal products, herbal medications, etc. within 7 days prior to study check-in and throughout the study.

After overnight fasting of at least about 10.00 hours, a high-fat high-calorie breakfast was served about 30 minutes prior to administration of investigational product(s). All subjects were required to consume their entire breakfast within about 30 minutes of it being served, a single dose of either test product (T) of Progesterone 200 mg & Estradiol 2 mg tablets or the reference product (R) PROMETRIUM® (Progesterone) soft gel Capsule 200 mg and ESTRACE® (Estradiol) Tablets 2 mg (according to the randomization schedule) were administered with about 240 mL of water under fed condition, at ambient temperature in each period in sitting posture. A thorough mouth check was done to assess the compliance to dosing.

All dosed study subjects were assessed for laboratory tests at the end of the study or as applicable.

In each period, twenty-three (23) blood samples were collected. The pre-dose (10 mL) blood samples at −01.00, −00.50, 00.00 hours and the post-dose blood samples (08 mL each) were collected at 00.25, 00.50, 00.67, 00.83, 01.00, 01.33, 01.67, 02.00, 02.50, 03.00, 04.00, 05.00, 06.00, 07.00, 08.00, 10.00, 12.00, 18.00, 24.00 and 48.00 hours in labeled K2EDTA—vacutainers via an indwelling cannula placed in one of the forearm veins of the subjects. Each intravenous indwelling cannula was kept in situ as long as possible by injecting about 0.5 mL of 10 IU/mL of heparin in normal saline solution to maintain the cannula for collection of the post-dose samples. In such cases blood samples were collected after discarding the first 0.5 mL of heparin containing blood. Each cannula was removed after the 24.00 hour sample was drawn or earlier or if blocked.

At the end of the study, the samples were transferred to the bio-analytical facility in a box containing sufficient dry ice to maintain the integrity of the samples. These samples were stored at a temperature of −70° C.±20° C. in the bio-analytical facility until analysis.

Progesterone (Corrected and Uncorrected) and Estradiol (unconjugated) and estrone (total) in plasma samples is assayed using a validated LC-MS/MS method.

The pharmacokinetic parameters Cmax, AUC0-t & AUC0-∞ were calculated on data obtained from 24 subjects for the test product and reference product. In general, bioavailability of progesterone and estradiol were similar but bioequivalence was not established.

Corrected pharmacokinetic profile summaries are presented in Table 9, below, for progesterone.

TABLE 9

Summary of Primary Pharmacokinetic Profile of Test Product (T) versus Reference Product (R) for Progesterone (Corrected)

| Pharmacokinetic Parameter | Geometric Mean* | | Arithmetic Mean ± Standard Deviation | |
|---|---|---|---|---|
| | Test Product (T) | Reference Product (R) | Test Product (T) | Reference Product (R) |
| $C_{max}$ | 47.0 | 43.0 | 81.0 ± 82.8 | 117.7 ± 173.7 |
| $AUC_{0-t}$ | 107.6 | 97.8 | 163.9 ± 136.5 | 191.1 ± 241.7 |
| $AUC_{0-\infty}$ | 110.7 | 110.0 | 173.5 ± 143.0 | 207.1 ± 250.3 |

*Estimate of Least Square Mean used to calculate Geometric Mean

Study 351—Progesterone and Estradiol Combination Study under Fasting Conditions.

Fasted studies using the above protocol and test and reference products were also conducted. However, rather than the high-fat meal prior to administration of the test and reference drug, each subject fasted for a period of at least twelve (12) hours prior to dose administration.

The pharmacokinetic parameters Cmax, AUC0-t & AUC0-∞ were calculated on data obtained from 23 subjects under fasting conditions for the test product and reference product. In general, bioavailability of progesterone and estradiol were similar but bioequivalence was not established.

Corrected pharmacokinetic profile summaries are presented in Table 10, below for progesterone.

TABLE 10

Summary of Primary Pharmacokinetic Profile of Test Product (T) versus Reference Product (R) for Progesterone (Corrected)

| Pharmacokinetic Parameter | Geometric Mean* | | Arithmetic Mean ± Standard Deviation | |
|---|---|---|---|---|
| | Test Product (T) | Reference Product (R) | Test Product (T) | Reference Product (R) |
| $C_{max}$ | 2.3 | 3.0 | 2.9 ± 2.3 | 3.9 ± 3.4 |
| $AUC_{0-t}$ | 8.4 | 10.9 | 11.2 ± 8.7 | 14.5 ± 11.0 |
| $AUC_{0-\infty}$ | 12.9 | 17.2 | 15.1 ± 9.0 | 19.6 ± 10.2 |

*Estimate of Least Square Mean used to calculate Geometric Mean

The data indicate good (i.e., low) inter-patient and intra-patient variability relative to PROMETRIUM.

Example 14

Dissolution

Dissolution studies were performed using a formulation of this invention comparing the dissolution of progesterone to the dissolution of PROMETRIUM and comparing the dissolution of estradiol to the dissolution of Estrace. In one study, a formulation of the invention in capsules comprising 200 mg of progesterone and 2 mg estradiol was used. In a second study, a formulation of the invention in capsules comprising 50 mg of progesterone and 2 mg estradiol was used. The two formulations comprised:

The dissolution study was performed using a USP dissolution apparatus (reciprocating cylinder) ("USP Apparatus 3"). The apparatus was set to 30 dips per minute. 250 mL of a solution of 0.1N HCl with 3% sodium lauryl sulfate was used at 37 C.

Figure 6:
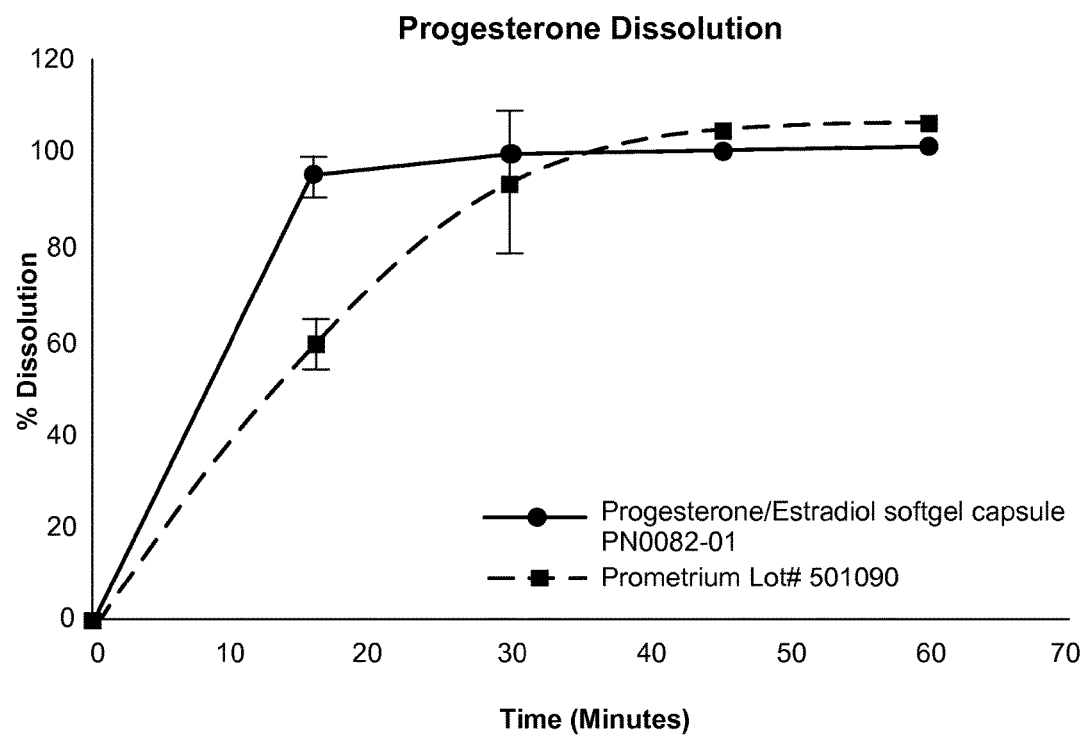
FIG. 6 illustrates a dissolution study of a formulation in accordance with various embodiments of the invention.

In both studies, progesterone was dissolved faster, and with smaller standard deviations, from the capsules of the invention than from PROMETRIUM. Dissolution of estradiol was comparable but marginally slower from the capsules of the invention than from Estrace. For illustrative purposes, a graph showing progestrone dissolution from the 200 mg progesterone capsule of the invention and from PROMETRIUM is attached as FIG. 6.

Both capsules of the invention were stable on storage in white HDPE bottles. Positive stability data were obtained with the 200 mg progesterone formulation over 6 months (>6 months data unavailable) and with the 50 mg progesterone formulation over 3 months (>3 months data unavailable).

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A pharmaceutical composition comprising:
    progesterone;
    a medium chain oil; and a non-ionic surfactant;
    wherein the progesterone is present from about 20 to about 50 weight percent of the composition.

2. The pharmaceutical composition of claim 1, wherein the progesterone is ultra-micronized and has an X50 less than or equal to 15 microns.

3. The pharmaceutical composition of claim 2, wherein the ultra-micronized progesterone has an X90 of less than about 25 microns.

4. The pharmaceutical composition of claim 1, wherein a portion of the progesterone is solubilized and a portion of the progesterone is suspended.

5. The pharmaceutical composition of claim 1, wherein the non-ionic surfactant is selected from the group consisting of lauroyl macrogol-32 glycerides EP, lauroyl polyoxyl-32 glycerides, and caprylocaproyl macrogol-8 glycerides EP.

6. The pharmaceutical composition of claim 1, wherein the composition is provided in a gelatin capsule.

7. The pharmaceutical composition of claim 1, wherein the composition provides increased bioavailability compared to a micronized progesterone suspended in peanut oil.

8. The pharmaceutical composition of claim 1, wherein progesterone is the sole active ingredient.

9. The pharmaceutical composition of claim 1, wherein the medium chain oil comprises at least one $C_6$-$C_{14}$ fatty acid mono-, di-, or tri-ester of glycerol or mono- or di-ester of a glycol.

10. The pharmaceutical composition of claim 9, wherein the at least one $C_6$-$C_{14}$ fatty acid mono-, di-, or tri-ester of glycerol is a $C_8$ fatty acid mono-, di-, or tri-ester of glycerol.

11. The pharmaceutical composition of claim 10, further comprising a second $C_6$-$C_{14}$ fatty acid mono-, di-, or tri-ester of glycerol.

12. The pharmaceutical composition of claim 11, wherein the second $C_6$-$C_{14}$ fatty acid mono-, di-, or tri-ester of glycerol is a $C_{10}$ fatty acid mono-, di-, or tri-ester of glycerol.

13. The pharmaceutical composition of claim 12, wherein the medium chain oil is MIGLYOL 812.

14. A pharmaceutical composition comprising:
75 mg of progesterone;
a medium chain oil; and
a non-ionic surfactant;
wherein the progesterone is present at from about 20 to about 50 weight percent of the composition.

15. The pharmaceutical composition of claim 14, wherein the progesterone is ultra-micronized and has an X50 less than or equal to 15 microns.

16. The pharmaceutical composition of claim 15, wherein the ultra-micronized progesterone has an X90 of less than about 25 microns.

17. The pharmaceutical composition of claim 14, wherein a portion of the progesterone is solubilized and a portion of the progesterone is suspended.

18. The pharmaceutical composition of claim 14, wherein the non-ionic surfactant is selected from the group consisting of lauroyl macrogol-32 glycerides EP, lauroyl polyoxyl-32 glycerides, and caprylocaproyl macrogol-8 glycerides EP.

19. The pharmaceutical composition of claim 14, wherein the composition is provided in a gelatin capsule.

20. The pharmaceutical composition of claim 14, wherein the composition provides increased bioavailability compared to a micronized progesterone suspended in peanut oil.

21. The pharmaceutical composition of claim 14, wherein progesterone is the sole active ingredient.

22. The pharmaceutical composition of claim 14, wherein the medium chain oil comprises at least one $C_6$-$C_{14}$ fatty acid mono-, di-, or tri-ester of glycerol or mono- or di-ester of a glycol.

23. The pharmaceutical composition of claim 22, wherein the at least one $C_6$-$C_{14}$ fatty acid mono-, di-, or tri-ester of glycerol is a $C_8$ fatty acid mono-, di-, or tri-ester of glycerol.

24. The pharmaceutical composition of claim 23, further comprising a second $C_6$-$C_{14}$ fatty acid mono-, di-, or tri-ester of glycerol.

25. The pharmaceutical composition of claim 24, wherein the second $C_6$-$C_{14}$ fatty acid mono-, di-, or tri-ester of glycerol is a $C_{10}$ fatty acid mono-, di-, or tri-ester of glycerol.

26. The pharmaceutical composition of claim 25, wherein the medium chain oil is MIGLYOL 812.

27. A pharmaceutical composition comprising:
150 mg progesterone;
a medium chain oil; and
a non-ionic surfactant;
wherein the progesterone is present at from about 20 to about 50 weight percent of the composition.

28. The pharmaceutical composition of claim 27, wherein the progesterone is ultra-micronized and has an X50 less than or equal to 15 microns.

29. The pharmaceutical composition of claim 28, wherein the ultra-micronized progesterone has an X90 of less than about 25 microns.

30. The pharmaceutical composition of claim 27, wherein a portion of the progesterone is solubilized and a portion of the progesterone is suspended.

31. The pharmaceutical composition of claim 27, wherein the non-ionic surfactant is selected from the group consisting of lauroyl macrogol-32 glycerides EP, lauroyl polyoxyl-32 glycerides, and caprylocaproyl macrogol-8 glycerides EP.

32. The pharmaceutical composition of claim 27, wherein the composition is provided in a gelatin capsule.

33. The pharmaceutical composition of claim 27, wherein the composition provides increased bioavailability compared to a micronized progesterone suspended in peanut oil.

34. The pharmaceutical composition of claim 27, wherein progesterone is the sole active ingredient.

35. The pharmaceutical composition of claim 27, wherein the medium chain oil comprises at least one $C_6$-$C_{14}$ fatty acid mono-, di-, or tri-ester of glycerol or mono- or di-ester of a glycol.

36. The pharmaceutical composition of claim 35, wherein the at least one $C_6$-$C_{14}$ fatty acid mono-, di-, or tri-ester of glycerol is a $C_8$ fatty acid mono-, di-, or tri-ester of glycerol.

37. The pharmaceutical composition of claim 36, further comprising a second $C_6$-$C_{14}$ fatty acid mono-, di-, or tri-ester of glycerol.

38. The pharmaceutical composition of claim 37, wherein the second $C_6$-$C_{14}$ fatty acid mono-, di-, or tri-ester of glycerol is a $C_{10}$ fatty acid mono-, di-, or tri-ester of glycerol.

39. The pharmaceutical composition of claim 38, wherein the medium chain oil is MIGLYOL 812.

40. The pharmaceutical composition of claim 27, wherein the medium chain oil is MIGLYOL 812, the non-ionic surfactant is lauroyl polyoxyl-32-glycerides, and wherein the pharmaceutical formulation provides increased progesterone bioavailability compared to a formulation comprising an equivalent amount of micronized progesterone suspended in peanut oil.

* * * * *

UNITED STATES PATENT AND TRADEMARK OFFICE
CERTIFICATE OF CORRECTION

PATENT NO. : 10,052,386 B2
APPLICATION NO. : 14/125547
DATED : August 21, 2018
INVENTOR(S) : Bernick et al.

Page 1 of 1

It is certified that error appears in the above-identified patent and that said Letters Patent is hereby corrected as shown below:

In the Specification

In Column 10, Line 31, replace "PEG-6-palmitostearate" with -- PEG-6 stearate --.

Signed and Sealed this
Twenty-third Day of July, 2019

Andrei Iancu
*Director of the United States Patent and Trademark Office*